(12) United States Patent
Bansal et al.

(10) Patent No.: US 12,090,201 B2
(45) Date of Patent: Sep. 17, 2024

(54) METHODS FOR TREATING ATOPIC DERMATITIS BY ADMINISTERING AN IL-4R ANTAGONIST ANTIBODY

(71) Applicant: Regeneron Pharmaceuticals, Inc., Tarrytown, NY (US)

(72) Inventors: Ashish Bansal, White Plains, NY (US); Neil Graham, Croton-on-Hudson, NY (US); Paola Mina-Osorio, Guttenberg, NJ (US); John Davis, Scarsdale, NY (US); Mohamed Kamal, Demarest, NJ (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 912 days.

(21) Appl. No.: 16/985,708

(22) Filed: Aug. 5, 2020

(65) Prior Publication Data
US 2021/0040222 A1 Feb. 11, 2021

Related U.S. Application Data

(60) Provisional application No. 63/032,408, filed on May 29, 2020, provisional application No. 63/024,467, filed on May 13, 2020, provisional application No. 62/985,715, filed on Mar. 5, 2020, provisional application No. 62/940,108, filed on Nov. 25, 2019, provisional application No. 62/882,946, filed on Aug. 5, 2019.

(51) Int. Cl.
| | | |
|---|---|---|
| A61K 39/395 | (2006.01) | |
| A61P 17/00 | (2006.01) | |
| A61K 39/00 | (2006.01) | |
| A61K 45/06 | (2006.01) | |
| C07K 16/28 | (2006.01) | |

(52) U.S. Cl.
CPC .......... *A61K 39/3955* (2013.01); *A61P 17/00* (2018.01); *A61K 2039/505* (2013.01); *A61K 2039/545* (2013.01); *A61K 45/06* (2013.01); *C07K 16/2866* (2013.01); *C07K 2317/21* (2013.01); *C07K 2317/56* (2013.01); *C07K 2317/76* (2013.01)

(58) Field of Classification Search
CPC .. A61K 39/3995; C07K 16/2866; A61P 17/00
See application file for complete search history.

(56) References Cited

U.S. PATENT DOCUMENTS

| | | |
|---|---|---|
| 5,599,905 A | 2/1997 | Mosley |
| 5,714,146 A | 2/1998 | Lewis |
| 5,717,072 A | 2/1998 | Mosley |
| 5,856,296 A | 1/1999 | Mosley |
| 5,985,280 A | 11/1999 | Ritter |
| 6,156,877 A | 12/2000 | Ritter |
| 6,391,581 B1 | 5/2002 | Mosley |
| 6,548,655 B1 | 4/2003 | Mosley |
| 6,716,587 B2 | 4/2004 | Mosley |
| 7,141,653 B2 | 11/2006 | Greenfeder |
| 7,186,809 B2 | 3/2007 | Pluenneke |
| 7,317,090 B2 | 1/2008 | Mosley |
| 7,422,742 B2 | 9/2008 | Greenfeder |
| 7,531,169 B2 | 5/2009 | Singh |
| 7,605,237 B2 | 10/2009 | Stevens |
| 7,608,693 B2 | 10/2009 | Martin |
| 7,794,717 B2 | 9/2010 | Stevens |
| 8,030,003 B2 | 10/2011 | Rothenberg |
| 8,075,887 B2 | 12/2011 | Martin |
| 8,075,897 B2 | 12/2011 | Spertini |
| 8,092,802 B2 | 1/2012 | Stevens |
| 8,092,804 B2 | 1/2012 | Eriksson |
| 8,252,284 B2 | 8/2012 | Singh |
| 8,324,192 B2 | 12/2012 | Dohil |
| 8,337,839 B2 | 12/2012 | Martin |
| 8,338,135 B2 | 12/2012 | Stevens |
| 8,497,528 B2 | 7/2013 | Lee |
| 8,604,171 B2 | 12/2013 | Singh |
| 8,637,239 B2 | 1/2014 | Furuta |
| 8,735,095 B2 | 5/2014 | Martin et al. |
| 8,945,559 B2 | 2/2015 | Dix |
| 9,238,692 B2 | 1/2016 | Dix |
| 9,290,574 B2 | 3/2016 | Kostic |
| 9,415,015 B2 | 8/2016 | Jacobi et al. |
| 9,574,004 B2 | 2/2017 | Ardeleanu |

(Continued)

FOREIGN PATENT DOCUMENTS

| | | |
|---|---|---|
| EP | 0604693 | 7/1994 |
| EP | 0367566 | 5/1997 |

(Continued)

OTHER PUBLICATIONS

Yang, Eun-Seok et al., "Anti-IL-4 Receptor mAb Attenuates Allergic Airway Hyperresponsiveness (AHR) and Inflammation in Allergic Mice", J. Allergy Clin. Immunol., Poster 168, Abstracts S69, vol. 109, No. 1 (2002), 1 page.

Russian Office Action and Search Report in Application 2020140639, mailed Aug. 17, 2022, with English translation, 26 pages.

Blakely, Kim et al., "Dupilumab, a monoclonal antibody for atopic dermatitis: a review of current literature", Skin Therapy Letter, Mar.-Apr. 2016, vol. 21, No. 2, Dupilumab Clinical Trials in AD, 13 pages.

(Continued)

*Primary Examiner* — Zachary C Howard

(74) *Attorney, Agent, or Firm* — Merchant & Gould P.C.

(57) ABSTRACT

Methods for treating moderate-to-severe or severe atopic dermatitis in a pediatric subject are provided. In one aspect, the methods comprise administering to the subject one or more doses of an interleukin-4 receptor (IL-4R) antagonist, such as an anti-IL-4R antibody or antigen-binding fragment thereof.

24 Claims, 10 Drawing Sheets

Specification includes a Sequence Listing.

(56) References Cited

U.S. PATENT DOCUMENTS

| Patent/Publication No. | Date | Inventor |
|---|---|---|
| 10,059,771 B2 | 8/2018 | Mannent |
| 10,066,017 B2 | 9/2018 | Mannent |
| 10,137,193 B2 | 11/2018 | Pirozzi |
| 10,370,449 B2 | 8/2019 | Graham |
| 10,392,439 B2 | 8/2019 | Stahl |
| 10,435,473 B2 | 10/2019 | Dix |
| 10,485,844 B2 | 11/2019 | Radin |
| 10,669,341 B2 | 6/2020 | Stahl |
| 10,676,530 B2 | 6/2020 | Stahl |
| 10,730,948 B2 | 8/2020 | Kostic |
| 11,034,768 B2 | 6/2021 | Amin |
| 11,053,309 B2 | 7/2021 | Radin |
| 11,292,847 B2 * | 4/2022 | Bansal ............... A61K 39/3955 |
| 2003/0103938 A1 | 6/2003 | Jinquan |
| 2003/0113387 A1 | 6/2003 | Tsuchida |
| 2003/0124121 A1 | 7/2003 | Pluenneke |
| 2005/0031609 A1 | 2/2005 | Hultsch |
| 2005/0074462 A1 | 4/2005 | Holmgren |
| 2005/0118176 A1 | 6/2005 | Mosley |
| 2005/0255532 A1 | 11/2005 | Ruben |
| 2005/0282181 A1 | 12/2005 | Yan |
| 2006/0013811 A1 | 1/2006 | Dina |
| 2007/0041976 A1 | 2/2007 | Pluenneke |
| 2007/0274996 A1 | 11/2007 | Carter |
| 2008/0054606 A1 | 5/2008 | Eriksson |
| 2008/0160035 A1 | 7/2008 | Stevens et al. |
| 2009/0074793 A1 | 3/2009 | Martin |
| 2009/0098142 A1 | 4/2009 | Kasaian |
| 2009/0264392 A1 | 10/2009 | Warndahl |
| 2010/0021476 A1 | 1/2010 | Stevens et al. |
| 2010/0047254 A1 | 2/2010 | Martin |
| 2010/0291107 A1 | 11/2010 | Stevens et al. |
| 2011/0195500 A1 | 8/2011 | Rothenberg |
| 2012/0004205 A1 | 1/2012 | Rothenberg |
| 2012/0052072 A1 | 3/2012 | Martin |
| 2012/0097565 A1 | 4/2012 | Dix |
| 2012/0135010 A1 | 5/2012 | Stevens et al. |
| 2012/0164080 A1 | 6/2012 | Hill |
| 2012/0207815 A1 | 8/2012 | Benhamou |
| 2013/0052190 A1 | 2/2013 | Collins |
| 2013/0078675 A1 | 3/2013 | Martin |
| 2013/0324435 A1 | 12/2013 | Rothenberg |
| 2014/0072583 A1 | 3/2014 | Ardeleanu |
| 2014/0187523 A1 | 7/2014 | Dohil |
| 2014/0271681 A1 | 9/2014 | Martin |
| 2014/0356372 A1 | 12/2014 | Stahl |
| 2015/0017176 A1 | 1/2015 | Kostic |
| 2015/0185228 A1 | 7/2015 | Reisacher |
| 2015/0246973 A1 | 9/2015 | Graham |
| 2016/0152718 A1 | 6/2016 | Kostic |
| 2016/0185866 A1 | 6/2016 | Mannent |
| 2017/0333557 A1 | 11/2017 | Ardeleanu |
| 2018/0078603 A1 | 3/2018 | Radin |
| 2018/0094069 A1 | 4/2018 | Stahl |
| 2018/0094070 A1 | 4/2018 | Stahl |
| 2018/0179288 A1 | 6/2018 | Martin et al. |
| 2019/0040126 A1 | 2/2019 | Radin |
| 2019/0169299 A1 | 6/2019 | Amin |
| 2019/0183973 A1 | 6/2019 | Hamilton |
| 2019/0345253 A1 | 11/2019 | Bansal |
| 2019/0367622 A1 | 12/2019 | Graham |
| 2020/0246416 A1 | 8/2020 | Radin |
| 2020/0299393 A1 | 9/2020 | Stahl |
| 2020/0332014 A1 | 10/2020 | Kostic |
| 2020/0345843 A1 | 11/2020 | Asrat |
| 2021/0038715 A1 | 2/2021 | Hamilton |
| 2021/0163611 A1 | 6/2021 | Martin |
| 2021/0220470 A1 | 7/2021 | Bryce et al. |
| 2021/0363237 A1 | 11/2021 | Radin |
| 2021/0363264 A1 | 11/2021 | Hamilton |
| 2022/0110999 A1 | 4/2022 | Radin |
| 2022/0220211 A1 | 7/2022 | Orengo |
| 2022/0298250 A1 | 9/2022 | Bansal |
| 2023/0058395 A1 | 2/2023 | Ardeleanu |
| 2023/0102151 A1 | 3/2023 | Bansal et al. |
| 2023/0167171 A1 | 6/2023 | Bansal |
| 2023/0220089 A1 | 7/2023 | Geba |
| 2023/0357416 A1 | 11/2023 | Graham |
| 2024/0141051 A1 | 5/2024 | Bansal |

FOREIGN PATENT DOCUMENTS

| | | |
|---|---|---|
| EP | 1113818 B1 | 5/2006 |
| EP | 2022507 A1 | 2/2009 |
| EP | 1527100 | 7/2009 |
| JP | 05-246874 | 9/1993 |
| JP | 2006-131623 | 5/2006 |
| JP | 2016521713 | 7/2016 |
| JP | 2018-511322 | 4/2018 |
| RU | 2162711 | 2/2001 |
| RU | 2283665 C2 | 9/2006 |
| RU | 2453303 C1 | 6/2012 |
| RU | 2552929 C1 | 6/2015 |
| RU | 2758092 C1 | 10/2021 |
| WO | WO 1992/19259 | 11/1992 |
| WO | WO 1994/14975 | 7/1994 |
| WO | WO 2001/092340 | 12/2001 |
| WO | WO 2003/048083 | 6/2003 |
| WO | WO 2005/047331 | 5/2005 |
| WO | WO 2005/085284 | 9/2005 |
| WO | WO 2006/003407 | 1/2006 |
| WO | WO 2006/072564 | 7/2006 |
| WO | WO 2006/083390 | 8/2006 |
| WO | WO 2008/054606 | 5/2008 |
| WO | WO 2008/116149 | 9/2008 |
| WO | WO 2009/124954 | 10/2009 |
| WO | WO 2010/053751 | 5/2010 |
| WO | WO 2010/065557 | 6/2010 |
| WO | WO 2010/120524 | 10/2010 |
| WO | WO 2011/026966 | 3/2011 |
| WO | WO 2012/047954 | 4/2012 |
| WO | WO 2012/094643 | 7/2012 |
| WO | WO 2012/177945 | 12/2012 |
| WO | WO 2013/051928 | 4/2013 |
| WO | WO 2013/088109 | 6/2013 |
| WO | WO 2013/116287 | 8/2013 |
| WO | WO 2013/155010 | 10/2013 |
| WO | WO 2014/031610 | 2/2014 |
| WO | WO 2014/039461 | 3/2014 |
| WO | WO 2014/059178 | 4/2014 |
| WO | WO 2014/122144 | 8/2014 |
| WO | WO 2014/197470 | 12/2014 |
| WO | WO 2014/205365 | 12/2014 |
| WO | WO 2015/006571 | 1/2015 |
| WO | 2015/127229 | 8/2015 |
| WO | WO 2016/077675 | 5/2016 |
| WO | WO 2017/143270 | 8/2017 |
| WO | 2018/035393 | 2/2018 |
| WO | WO 2018/045130 | 3/2018 |
| WO | WO 2018/057776 | 3/2018 |
| WO | WO 2018/151836 | 8/2018 |
| WO | WO 2018/201051 | 11/2018 |
| WO | 2019/089473 | 5/2019 |
| WO | 2021/195530 | 9/2021 |

OTHER PUBLICATIONS

Clinical Trials, Study NCT01859988, phase 2b, "Study of Dupilumab Administered to Adult Patients With Moderate-to-Severe Atopic Dermatitis", study completion date—Sep. 2014, 10 pages.

D'Erme, Angelo et al., "Spotlight on dupilumab in the treatment of atopic dermatitis: design, development, and potential place in therapy", Drug Des Devel Ther, 2017, vol. 11, p. 1473-1480, DOI:10.2147/DDDT.S113192, Abstract, c.1475-1478, 8 pages.

Grechkina, L.I. et al., "Characteristics for the physical development indices demonstrated by adolescents born in Magadan", Siberian Medical Journal, 2013, No. 3, Results and discussion, Table 1, obtained from: https://cyberleninka.ru/article/n/harakteristika-pokazateley-fizicheskogo-razvitiya-podrostkov-urozhentsev-magadana/viewer, with English translation, 9 pages.

Yamashita, Shuya et al., "Flavones suppress type I IL-4 receptor signaling by down-regulating the expression of common gamma

(56) References Cited

OTHER PUBLICATIONS chain", FEBS Letters, 2010, vol. 584, issue 4, p. 775-779, Abstract, Introduction, located at: https://febs.onlinelibrary.wiley.com/doi/full/10.1016/j.febslet.2009.12.044, 13 pages.
Balabolkin, I. et al., "Modern concepts of pathogenesis and therapy of atopic dermatitis in children", Pharmateka, 2017, No. 1, p. 53-60, with English translation, 14 pages.
Gong, J.Q. et al., "Skin Colonization by *Staphylococcus aureus* in patients with eczema and atopic dermatitis and relevant combined topical therapy: a double-blind multicentre randomized controlled trial", British Journal of Dermatology, No. 155, pp. 680-687 (2006), Mar. 28, 2006.
Van Assche, Gert, et al., "Management of loss of response to anti-TNF drugs: Change the dose or change the drug?", Journal of Crohn's and Colitis, vol. 2, No. 4, Dec. 1, 2008, pp. 348-351.
Clinical Trials, Study NCT03682770—"Study in Pediatric Subjects With Peanut Allergy to Evaluate Efficacy and Safety of Dupilumab as Adjunct to AR10 Immunotherapy" Aug. 20, 2020, located at: URL:https://clinicaltrials.gov/ct2/history/NCT03682770?V_8=View#StudyPageTop, (retrieved on Mar. 10, 2022), 7 pages.
Corren, Jonathan et al., "Short-term subcutaneous allergy immunotherapy and dupilumab are well-tolerated in allergic rhinitis: A randomized trial", Journal of Asthma and Allergy, vol. 14, Aug. 16, 2021, pp. 1045-1063.
Bruton, Kelly et al., "Interrupting reactivation of immunologic memory diverts the allergic response and prevents anaphylaxis", Journal of Allergy and Clinical Immunology, vol. 147, No. 4, Dec. 15, 2020, pp. 1381-1392.
Wambre, ER, "Baseline characteristics of peanut-allergic individuals during the dupilumab as adjunct to AR101 clinical trial", Abstract, retrieved at: https://onlinelibrary.wiley.com/doi/10.1111/all.14506, Sep. 7, 2020, 1 page.
Chaker, Adam et al., "Short-term subcutaneous grass pollen immunotherapy under the umbrella of anti-IL-4: A randomized controlled trial", Journal of Allergy and Clinical Immunology, vol. 137, No. 2, Oct. 31, 2015, 19 pages.
Ayars, Andrew G. et al., "Pharmacologic Therapies in Pulmonology and Allergy", 2016 Med Clin N Am 100(4):851-868.
Mashkovsky, M.D., Moscow, 2001 Medicines, 14th edition, v1:8-9. (Cited in RU Application 2019109062.
Russian Office Action and Search Report in Application 2019109062, with English translation, 32 pages.
Prokofieva, L.V. et al., "A course of lectures on general pharmacology: a teaching aid", Ulyanovsk: UlGU, 2017, p. 155, p. 15, paragraph 7, with English translation of specified paragraph, 156 pgs. total.
Russian Office Action in Application 2020140639 mailed Jan. 12, 2023, with English translation, 9 pages.
Mulder, DJ et al., "Understanding eosinophilic esophagitis: the cellular and molecular mechanisms of an emerging disease", Mucosal Immunology, Mar. 2011, vol. 4, No. 2, pp. 139-147.
Linden, Carey et al., "Analysis of allergen specific IgE cut points to cat and dog in the Childhood Allergy Study", Annals of Allergy, Asthma & Immunology, 2011, 106.2: 153-158. e2.
Silverberg et al., "Atopic Dermatitis: Update on Pathogenesis and Comorbidities", Curr Derm Rep (2012) 1:168-178.
Wikipedia, "Mycosis fungoides", retrieved from: https://en.wikipedia.org/w/index.php?title=Mycosis_fungoides&oldid=1156079659, obtained on May 31, 2023, 9 pages.
Callewaert, Chris et al., "IL-4Ra Blockade by Dupilumab Decreases *Staphylococcus aureus* Colonization and Increases Microbial Diversity in Atopic Dermatitis", Journal of Investigative Dermatology (2020) 140, 191-202.
Kwiatek, Monika et al., "Mechanical properties of the esophagus in eosinophilic esophagitis" Gastroenterology, 2011, vol. 140, No. 1, pp. 82-90.
Abe, Yasuhiko, et al., "The Diagnosis of Eosinophilic Esophagitis", (English abstract), Gastroenterological Endoscopy, Sep. 2014, vol. 56, Issue 9, pp. 3378-3393.

Garraud, Olivier, et al., "Regulation of immunoglobulin production in hyper-IgE (Job's) syndrome", J. Allergy Clin. Immunol., Feb. 1999. (2 Pt. 1): 333-340.
Finkelman, Fred, et al., "Regulation of murine in vivo IgG and IgE responses by a monoclonal anti-IL-4 receptor antibody", Jun. 1991;3(6); 599-607.
"Dupilumab therapy in moderate-to-severe atopic dermatitis provides positive results in the first two phase III clinical trials", J Int Pharm Res, vol. 43, No. 4, Aug. 31, 2016, p. 785 (with English translation).
Igelman, Sean et al., "Off-label use of dupilumab for pediatric patients with atopic dermatitis: A multicenter retrospective review", Journal of the American Academy of Dermatology, Mosby, Inc., US, vol. 82, No. 2, Oct. 10, 2019, pp. 407-411.
Abonia et al. (2013) Journal of Allergy Clin Immunol "High prevalence of eosinophilic esophagitis in patients with inherited connective tissue disorders".
Abstracts, "Human Clinical Research and Therapeutics", Journal of Investigative Dermatology vol. 133, Supplement 1, (2013), pp. S159-S190, Abstracts 1042, and 1048 to 1050, http://apps.webofknowledge.com/full_record.do?product=WOS&search_mode=GeneralSearch&qid=2& SID=E6MDFsiCnXC9MfROx21&page=1&doc=1, 32 pages.
Aceves et al. (2009) Immunol Allergy Clin N Am 29:197-211 "Relationships Between Eosinophilic Inflammation, Tissue Remodeling, and Fibrosis in Eosinophilic Esophagitis".
Akiyama, et al., A Study on Indoor Allergens Measured in Home Environments of Adult-Asthmatic Patients, Housing Research Foundation, Research Annual Report, 1997, No. 24, Study No. 9620, 1-10.
Almagro et al., "Humanization of antibodies", (2008) Frontiers in Bioscience 13:1619-1633.
Antoniu, Sabina, "Pitrakinra, a Dual IL-4R/IL-13 Antagonist for the Potential Treatment of Asthma and Eczema", Current Opinion in Investigational Drugs 2010 11 (11): 1286-1294.
Arron et al. (2009) Am. J. Respir. Crit. Care Med. Online Abstracts Issue. 2009, B21 Airway Inflammation: New Information about Mediators and Biomarkers/Poster Discussion/Monday, May 18, 2009 "Peripheral Biomarkers of an IL-13 Induced Bronchial Epithelial Gene Signature in Asthma".
Assa'ad et al. (2011) Gastroenterology 141:1593-1604 "An Antibody Against IL-5 Reduces Numbers of Esophageal Intraepithelial Eosinophils in Children with Eosinophilic Esophagitis".
Assa'ad, Amal, What is new in the Treatment of Eosinophilic Eosophagitis? Clinical and Translational Allergy 2011 (Suppl 1):S69, doi: 10.1186/2045-7022-1-S 1-S69.
Bachert et al. (2005) Drugs 65(11):1537-1552 "Pharmacological management of nasal polyposis".
Bagnasco, Diego et al., "A critical evaluation of Anti-IL-13 and Anti-IL-4 Strategies in Severe Asthma", Int. Arch Allergy Immunol 2016; 170: 122-131.
Balint and Larrick (1993) Gene 137:109-118 "Antibody engineering by parsimonious mutagenesis".
Bankhead, Charles, "IL-4 Antibody Tames Atopic Dermatitis", Medpage Today Article, https://www.medpagetoday.com/meetingcoverage/aad/37636, Mar. 3, 2013, 3 pages.
Barnes (2008) The Journal of Clinical Investigation 118(11):3546-3556 "The cytokine network in asthma and chronic obstructive pulmonary disease".
Bateman et al. (2004) Am. J. Respir. Crit. Care Med. 170:836-844 "Can guideline-defined asthma control be achieved?".
Beck et al. (Jul. 10, 2014) New England Journal of Medicine 371(2): 130-139 "Dupilumab treatment in adults with moderate-to-severe atopic dermatitis".
Beyer et al. (2002) Journal of Allergy Clin Immunol 109(4):707-713 "Human milk-specific mucosal lymphocytes of the gastrointestinal tract display a $T_H2$ cytokine profile".
Bhardwaj and Ghaffari (2012) Ann Allergy Asthma Immunol 109:155-159 "Biomarkers for eosinophilic esophagitis: a review".
Bieber, T., et al., "Atopic dermatitis: a candidate for disease-modifying strategy," Allergy 67 (2012) 969-975.

(56) References Cited

OTHER PUBLICATIONS

Blanchard and Rothenberg (2009) Immunol Allergy Clin N Am 29:141-148 "Chemotactic Factors Associated with Eosinophilic Gastrointestinal Diseases".
Blanchard et al. (2005) Clin Exp Allergy 35:1096-1103 "Inhibition of human interleukin-13-induced respiratory and oesophageal inflammation by anti-human-interleukin-13 antibody (CAT-354)".
Blanchard et al. (2006) The Journal of Clinical Investigation 116(2) "Eotaxin-3 and a uniquely conserved gene-expression profile in eosinophilic esophagitis".
Blanchard et al. (2007) Journal of Allergy Clin Immunol 120(6) "IL-13 involvement in eosinophilic esophagitis: Transcriptome analysis and reversibility with glucocorticoids".
Blanchard et al. (2010) The Journal of Immunology "Coordinate Interaction between IL-13 and Epithelial Differentiation Cluster Genes in Eosinophilic Esophagitis".
Blanchard et al. (2011) J Allergy Clin Immunol 127(1):208-217 "A striking local esophageal cytokine expression profile in eosinophilic esophagitis".
Blauvelt, Andrew, et al., "Long-term management of moderate-to-severe atopic dermatitis with dupilumab and concomitant topical corticosteroids (Liberty Ad Chronos): a 1-year, randomised, double-blinded, placebo-controlled, phase 3 trial," www.thelancet.com, published online May 4, 2016, http://dx.doi.org/10.1016/S0140-6736(17)31191-1.
British Society for Allergy and Clinical Immunology (BSACI) Abstracts of the 2013 Annual Meeting (dated Jul. 8-10, 2013), Clinical & Experimental Allergy, 43, 1428-1472, Nov. 22, 2013, https://onlinelibrary.wiley.com/toc/13652222/2013/43/12, 45 pages.
Brown-Whitehorn and Spergel (2010) Expert Rev Clin Immunol. 6:1:101-115 "The link between allergies and eosinophilic esophagitis: implications for management strategies".
BSACI News Report confirming BSACI conference date of Jul. 8-10, 2013, 2 pages.
Burmeister-Getz et al. (2009) J. Clin. Pharmacol. 49:1025-1036 "Human pharmacokinetics/pharmacodynamics of an interleukin-4 and interleukin-13 dual antagonist in asthma".
Burton, et al., "Direct effects of IL-4 on mast cells drive their intestinal expansion and increase susceptibility to anaphylaxis in a murine model of food allergy," Mucosal Immunology, Nov. 14, 2012, doi:10.1038/mi.2012.112.
Caldas et al. (2003) Molecular Immunology 39:941-952 "Humanization of the anti-CD18 antibody 6.7: an unexpected effect of a framework residue in binding to antigen".
Carter (2006) The Journal of Immunology 6:343-357 "Potent Antibody Therapeutics by Design".
Casset et al. (2003) Biochemical and Biophysical Research Communication 307:198-205 "A peptide mimetic of an anti-CD4 monoclonal antibody by rational design".
Chehade and Sampson (2009) Immunol Allergy Clin N Am 29:149-158 "The Role of Lymphocytes in Eosinophilic Gastrointestinal Disorders".
Cheng et al. (2012) Am J Physiol Gastrointest Liver Physiol 303:G1175-G1187 "Tissue remodeling in eosinophilic esophagitis".
Chien et al. (1989) Proc. Natl. Acad. Sci. 86:5532-5536 "Significant structural and functional change of an antigen-binding site by a distant amino acid substitution: Proposal of a structural mechanism".
Collins, Margaret H. et al., "Sa1151—Baseline Characteristics and Correlation Between Dysphagia and Disease Activity in Patients with Eosinophilic Esophagitis in a Randomized, Placebo-Controlled, Phase 2 Dupilumab Trial", abstract, Gastroenterology, vol. 154, No. 6, May 1, 2016, 1 page.
Corren et al. (2010) American Journal of Respiratory and Critical Care Medicine 181(8):788-796 "A Randomized, Controlled, Phase 2 Study of AMG 317, an IL-4R Antagonist, in Patients with Asthma".
Cortes, J.R., et al., Proton pump inhibitors inhibit IL-4 and IL-13 signaling stat6 activation, European Journal of Immunology, (Sep. 2009) vol. 39, Supp.

Davies et al. (1996) Immunotechnol. 2(3): 169-179 "Affinity improvement of single antibody VH domains: residues in all three hypervariable regions affect antigen binding".
Davis (2004) Seminars in Immunology 16:239-243 "The evolutionary and structural 'logic' of antigen receptor diversity".
De Pascalis et al. (2002) Journal of Immunology 169(6):3076-3084 "Grafting of "Abbreviated" Complementarity-Determining Regions Containing Specificity-Determining Residues Essential for Ligand Contact to Engineer a Less Immunogenic Humanized Monoclonal Antibody".
Dellon (2013) Dig Dis Sci "The Pathogenesis of Eosinophilic Esophagitis: Beyond the Eosinophil".
Dellon, Evan S. et al., "A Randomized, Double-Blind, Placebo-Controlled Trial of a Novel Recombinant, Humanized, Anti-Interleukin-13 Monoclonal Antibody (RPC4046) in Patients with Active Eosinophilic Esophagitis: Results of the HEROES Study", Oct. 14, 2016, retrieved from the Internet on Sep. 20, 2018 at: https://www.eventscribe.com/2016/ACG/QRcode.asp?Pres=178380, 3 pages.
Desreumaux et al. (1996) Gastroenterology 110:768-774 "Interleukin 3, Granulocyte-Macrophage Colony-Stimulating Factor, and Interleukin 5 in Eosinophilic Gastroenteritis".
Durham, Andrew L. et al., "Targeted anti-inflammatory therapeutics in asthma and chronic obstructive lung disease", Airway Disease Section, Nat'l. Heart and Lung Institute, Imperial College London, UK, published Aug. 12, 2015, 12 pages.
European Notice of Opposition in Application 13765844.9, mailed Feb. 22, 2019, 34 pages.
Fillon et al. (2009) Immunol Allergy Clin N Am 29:171-178 "Epithelial Function in Eosinophilic Gastrointestinal Diseases".
Foote and Winter (1992) J. Mol. Biol. 224:487-499 "Antibody Framework Residues Affecting the Conformation of the Hypervariable Loops".
Foroughi et al. (2007) J Allergy Clin Immunol 120(3):594-601 "Anti-IgE Treatment of Eosinophil Associated Gastrointestinal Disorders".
Franciosi and Liacouras (2009) Immunol Allergy Clin N Am 29:19-27 "Eosinophilic Esophagitis".
Garriga, A., "71st Annual Meeting of the American Academy of Dermatology (AAAD) . . . Miami Beach, FL, Mar. 1-5, 2013", Drugs of the Future 2013, 38(4): 275-279, Apr. 2013, https://journals.prous.com/journals/servlet/xmlxls/pk_journals.xml_toc_pr?p_JournalID=2&p_IssueID=1186, 5 pages.
Gavett et al. (1997) The American Physiological Society 272(16): L253-L261 "Interleukin-4 receptor blockade prevents airway responses induced by antigen challenge in mice".
Gevaert et al. (2006) Journal of Allergy and Clinical Immunology 118(5):1133-1141 "Nasal IL-5 levels determine the response to anti-IL-5 treatment in patients with nasal polyps".
Giusti et al. (1987) Proc. Natl. Acad. Sci. 84:2926-2930 "Somatic diversification of S107 from an antiphosphocholine to anti-DNA autoantibody is due to a single base change in its heavy chain variable region".
Groves et al. (2007) Aeroderm in AD Poster at St. John's Institute of Dermatology "Inhibition of IL-4 and IL-13 with an IL-4 mutein (Aeroderm) protects against flares in atopic eczema".
Grunewald et al. (1998) The Journal of Immunology 160(8):4004-4009 "An Antagonistic IL-4 Mutant Prevents Type I Allergy in the Mouse: Inhibition of the IL-4/IL-13 Receptor System completely Abrogates Humoral Immune Response to Allergen and Development of Allergic Symptoms in Vivo".
Gussow and Seemann (1991) Methods in Enzymology 203:99-121 "Humanization of Monoclonal Antibodies".
Hamilton, Jennifer D., et al., "Drug evaluation review: Dupilumab in atopic dermatitis," Immunotherapy (Oct. 1, 2015) 7(10), 1043-1058.
Hijnen et al. (2004) J. Allergy Clin. Immunology 113(2): 334-340 "Serum thymus and activation-regulated chemokine (TARC) and cutaneous T Cell-attracting chemokine (CTACK) levels in allergic diseases: TARC and CTACK are disease-specific markers for atopic dermatitis".
Hirano, Ikuo et al., "Dupilumab Efficacy and Safety in Adult Patients With Active Eosinophilic Esophagitis: a Randomized Double-

(56) References Cited

OTHER PUBLICATIONS

Blind Placebo-Controlled Phase 2 Trial", Oct. 13, 2017, retrieved from the internet on Sep. 20, 2018 at: http://files.shareholder.com/downloads/REGN/6138593856x0x959724/16AF93AE-DAF8-480A-8301-311C91E8FA41/Presentation.pdf, 20 pages.
Hirano, Ikuo et al., "Sa1113—Correlation Between Esophageal Distensibility and Objective Measures of Disease in Patients with Active Eosinophilic Esophagitis: A Post HOC Analysis of a Randomized, Placebo-Controlled, Phase 2 Dupilumab Trial", abstract, Gastroenterology, vol. 154, No. 6, May 1, 2018, 1 page.
Holm et al. (2007) Molecular Immunology 44:1075-1084 "Functional mapping and single chain construction of the anti-cytokeratin 8 monoclonal antibody TS1".
Holt et al. (2003) Trends in Biotechnology 21(11):484-490 "Domain antibodies: proteins for therapy".
Hong, Judith, et al., "Management of Itch in Atopic Dermatitis," Seminars in cutaneous Medicine and Surgery, vol. 30, No. 2, May 14, 2011, pp. 71-86, XP028240445.
Hopkins (2009) Clinical Otolaryngology 34(5):447-454 "Psychometric validity of the 22-item Sinonasal Outcome Test".
Hopkins et al. (2007) Otolaryngology-Head and Neck Surgery 137(4):555-561 "The Lund-Mackay staging system for chronic rhinosinusitis: How is it used and what does it predict?".
International Investigative Dermatology, Edinburgh, Conference Posters, May 8-11, 2013, 4 pages.
Ivashkiin, V. T., et al., "Eosinophillic esophagitis," a textbook for physicians, Moscow, "AISPI RAS" JSC, Feb. 14, 2013, pp. 13-21, 57-62 No English translation. (Cited in Russian Office Action for RU Appl. No. 2016104400).
Ivashkin, V. T., et al., "Eosinophilic esophagitis: literature review and description of own survey," RJGHC, 2012, vol. 22, 1, pp. 71-81.
Jahnz-Rozyk et al. (2005) Allergy 60:685-688 "Serum thymus and activation-regulated chemokine, macrophage-derived chemokine and eotaxin as marker of severity of atopic dermatitis".
Joost, T.H. Van, "Cyclosporin in atopical dermatitis: a multicentre placebo-controlled study", Journal of the American Academy of Dermatology, (1992), vol. 27, Issue 6, Part 1, pp. 922-928.
Journal of Allergy & Clinical Immunology: Abstracts at conference; https://www.jacionline.org/issue/S0091-6749(13)X0013-2, Feb. 2013, 1 page.
Junttila et al. (2008) J. Exp. Med. 205(11):2595-2608 "Tuning sensitivity to IL-4 and IL-13: differential expression of IL-4Rα, IL-13Rα1, and Yc regulates relative cytokine sensitivity".
Jyonouchi et al. (2013) Basic Mechanisms in Allergic Disease "Invariant Natural Killer T cells in children with Eosinophilic Esophagitis".
Kagami et al. (2003) Clin. Exp. Immunology 134:309-313 "Significant elevation of serum levels of eotaxin-3/CCL26, but not of eotaxin-2/CCL24, in patients with atopic dermatitis: serum eotaxin-3/CCL26 levels reflect the disease activity of atopic dermatitis".
Kakinuma et al. (2002) Clin. Exp. Immunol 127:270-273 "Serum macrophage-derived chemokine (MDC) levels are closely related with the disease activity of atopic dermatitis".
Kakinuma, Takashi et al. (2001) J. Allergy Clin. Immunol. 107(3):535-541 "Thymus and activation-regulated chemokine in atopic dermatitis: Serum thymus and activation-regulated chemokine level is closely related with disease activity".
Kakkar, Tarundeep et al. (2011) Pharmaceutical Research 28(10):2530-2542 "Population PK and IgE Pharmacodynamic Analysis of a Fully Human Monoclonal Antibody Against IL4 Receptor".
Katial (2009) Immunol Allergy Clin N Am 29:119-127 "Biomarkers for Nononcologic Gastrointestinal Disease".
Kelly and Liu (2014) World Allergy Organization Journal 7(S1):P8 "Poster 1013: IL-4R alpha antibody inhibits IgE production and airway remodeling in mouse model of house dust mite-induced eosinophilic asthma".
Kim et al. (2004) J Allergy Clin Immunol 114(6):1449-1455 "Rebound eosinophilia after treatment of hypereosinophilic syndrome and eosinophilic gastroenteritis with monoclonal anti-IL-5 antibody SCH55700".
Konikoff et al. (2006) Gastroenterology 131:1381-1391 "A Randomized, Double-Blind, Placebo-Controlled Trial of Fluticasone Propionate for Pediatric Eosinophilic Esophagitis".
Kopf et al. (1993) Letters to Nature 362:245-248 "Disruption of the murine IL-4 gene blocks Th2 cytokine responses".
Kostic et al. (2010) Clinical Immunology 135:S105-S106 "A Fully Human IL4Rα Antibody for Inhibition of IL-4/IL-13-driven TH2 Responses in Allergic Disease".
Kottyan et al. (2014) Nature Genetics "Genome-wide association analysis of eosinophilic esophagitis provides insight into the tissue specificity of this allergic disease".
Kulis et al. (2011) J. Allergy Clin Immunol 127:81-88 "Single-tree nut immunotherapy attenuates allergic reactions in mice with hypersensitivity to multiple tree nuts".
Leung et al. (2003) The New England Journal of Medicine 348:986-993 "Effect of Anti-IgE Therapy in Patients with Peanut Allergy".
Leung et al. (2004) The Journal of Clinical Investigation 113(5):651-657 "New insights into atopic dermatitis".
Lezcano-Meza et al. (2003) Allergy 58(10):1011-1017 "Interleukin (IL)-4 and to a lesser extent either IL-13 or interferon-gamma regulate the production of eotaxin-2/CCL24 in nasal polyps".
Liacouras et al. (2011) J Allergy Clin Immunol 128(1) "Eosinophilic esophagitis: Updated consensus recommendations for children and adults".
Lin et al (2007) Clinical Reviews in Allergy & Immunology 33(3):167-177 "Role of Bacterial Pathogens in Atopic Dermatitis".
Liu et al. (1999) Gene Therapy 6:1258-1266 "Hydrodynamics-based transfection in animals by systemic administration of plasmid DNA".
Lucendo and Sanchez-Cazalilla (2012) Expert Rev. Clin. Immunol. 8(8):733-745 "Adult versus pediatric eosinophilic esophagitis: important differences and similarities for the clinician to understand".
Ludmila and Xia (2014) World Allergy Organization Journal 7(1):P8 "Poster 1013: IL-4R alpha antibody inhibits IgE production and airway remodeling in mouse model of house dust mite-induced eosinophilic asthma".
Lwin et al. (2011) Modern Pathology 24:556-563 "Eosinophilic gastritis: histopathological characterization and quantification of the normal gastric eosinophil content".
MacCallum et al. (1996) J. Mol. Biol. 262:732-745 "Antibody-antigen Interactions: Contact Analysis and Binding Site Topography".
Maliszewski et al. (1994) Proc. Soc. Exp. Biol. Med. 206(3):233-237 "In vivo biological effects of recombinant soluble interleukin-4 receptor".
Mannon et al. (2012) GUT 61(12):1765-1773 "Interleukin 13 and its role in gut defence and inflammation".
Mariuzza et al. (1987) Ann. Rev. Biophys. Biophys. Che. 16:139-159 "The Structural Basis of Antigen-Antibody Recognition".
Martel, Britta C., et al., "Translational animal Models of Atopic Dermatitis for Preclinical Studies," Yale Journal of Biology and Medicine 90 (2017), pp. 389-402.
Masterson et al. (2011) Curr Opin Gastroenterol. 27(6):515-522 "Update on clinical and immunological features of eosinophilic gastrointestinal diseases".
Mathias, et al., "IgE-mediated systemic anaphylaxis and impaired tolerance to food antigens in mice with enhanced IL-4 receptor signaling," Journal of Allergy and Clinical Immunology, 2011, vol. 127, No. 3, 795-805, e1-e6.
Mishra and Rothenberg (2003) Gastroenterology 125:1419-1427 "Intratracheal IL-13 Induces Eosinophilic Esophagitis by an IL-5, Eotaxin-1, and STAT6-Dependent Mechanism".
Mishra et al. (2001) J Clin. Invest. 107:83-90 "An etiological role for aeroallergens and eosinophils in experimental esophagitis".
Mishra et al. (2002) The Journal of Immunology 168:2464-2469 "IL-5 Promotes Eosinophil Trafficking to the Esophagus".
Moldoveanu et al. (2009) Journal of Inflammation Research 2:1-11 "Inflammatory mechanisms in the lung".
Molfino et al. (2012) Clinical & Experimental Allergy 42(5):712-737 "Molecular and clinical rationale for therapeutic targeting of interleukin-5 and its receptor".

(56) References Cited

OTHER PUBLICATIONS

Morioka et al. (2009) British Journal of Dermatology 160(6):1172-1179 "IL-4/IL-13 antagonist DNA vaccination successfully suppresses Th2 type chronic dermatitis".
Mueller, Thomas D. et al., "Structure, binding, and antagonists in the IL-4/IL-13 receptor system", Biochimica et Biophysica Acta (2002) 237-250.
Müller et al. (1993) Journal of Immunology 150:5576-5584 "Th2 cells mediate IL-4-dependent local tissue inflammation".
Nadeau et al. (2011) J. Allergy Clin. Immunol 127(6) Letters to the Editor "Rapid oral desensitization in combination with omalizumab therapy in patients with cow's milk allergy".
Nadeau, et al., "Oral Immunotherapy and Anti-IgE Antibody-Adjunctive Treatment for Food Allergy," Immunology and Allergy clinics of North America, 2012, vol. 32, No. 1, 111-133.
Nguyen et al. (2011) Immunological Reviews 242(1):258-271 "Immune modulation for treatment of allergic disease".
Nguyen, Tran Hoai et al., "FutureForms of Immunotherapy and Immunomodulators in Allergic Disease", Immunol Allergy Clin N Am 31 (2011); 343-365.
Niederberger (2009) Immunology Letters 122:131-133 "Allergen-specific immunotherapy".
Niranjan et al. (2013) Immunology and Cell Biology pp. 1-8 "Pathogenesis of allergen-induced eosinophilic esophagitis is independent of interleukin (IL)-13".
Noel et al. (2004) The New England Journal of Medicine 351:940-941 "Eosinophilic Esophagitis".
Novartis (2013) QAX576 "A double blinded, randomized, placebo-controlled trial of intravenous QAX576 in the treatment of eosinophilic esophagitis".
Oetjen, Landon K., et al., "Sensory Neurons Co-opt Classical Immune Signaling Pathways to Mediate Chronic Itch," Sep. 21, 2017, Cell 171, 217-228.
Oh et al. (2010) Eur Respir Rev 19(115):46-54 "Investigational therapeutics targeting the IL-4/IL-13/STAT-6 pathway for the treatment of asthma".
Ohno et al. (1985) Proc. Natl. Acad. Sci. USA 82:2945-2949 "Antigen-binding specificities of antibodies are primarily determined by seven residues of $V_H$".
Ong (2012) Expert Opinion on Emerging Drugs 17(2):129-133 "Editorial update on emerging treatments of atopic dermatitis".
Otani et al. (2013) Journal of Allergy and Clinical Immunology 131(6): 1576-1582 "Anti-IL-5 therapy reduces mast cell and IL-9 cell numbers in pediatric patients with eosinophilic esophagitis".
Otulana et al. (2011) Am. J. Respir. Crit. Care Med. 183:A6179 "A Phase 2b Study of Inhaled Pitrakinra, An IL-4R/IL-13 Antagonist, Successfully Identified Responder Subpopulations of Patients with Uncontrolled Asthma".
Oyoshi et al. (2009) Advances in Immunology 102:135-226 "Cellular and Molecular Mechanisms in Atopic Dermatitis".
Paton, D. M., "Dupilumab: human monoclonal antibody against IL-4Ralpha for moderate to severe atopic dermatitis," Drugs Today, vol. 53, No. 9, Sep. 1, 2017, pp. 477-487, XP055465888.
Pesek, Robert D. et al., "Emerging drugs for eosinophilic esophagitis", Expert Opinion on Emerging Drugs, vol. 23, No. 2, Apr. 3, 2018, 12 pages.
Peserico et al. (2008) British Journal of Dermatology 158:801-807 "Reduction of relapses of atopic dermatitis with methylprednisolone aceponate cream twice weekly in addition to maintenance treatment with emollient: a multicentre, randomized, double-blind, controlled study".
Petry et al. (2012) Anais Brasileiro De Dermatologia 87(5):732-733 "Bacterial skin colonization and infections in patients with atopic dermatitis".
Prieto and Richter (2013) Curr Gastroenterol Rep 15:324 "Eosinophilic Esophagitis in Adults: an Update on Medical Management".
Prussin et al. (2009) J Allergy Clin Immunol. 124(6):1326-1332 "Eosinophilic gastrointestinal disease and peanut allergy are alternatively associated with IL-5+ and IL-5-TH2 responses".
Rafi et al. (2010) Allergy and Asthma Proceedings 31(1):76-83 "Effects of omalizumab in patients with food allergy".
Rayapudi et al. (2010) Journal of Leukocyte Biology 88 "Indoor insect allergens are potent inducers of experimental eosinophilic esophagitis in mice".
Receptos, Inc. 2013 Annual Report.
Ring et al. (2012) J. Eur. Acad. Dermatol. Venereol. 26(8): 1045-1060 "Guidelines for treatment of atopic eczema (atopic dermatitis) Part 1".
Roitt et al. (2001) Mosby—Harcourt Publishers Limited, Immunology—Sixth Edition "Antigen Presentation" pp. 110-111.
Roll et al. (2006) J. Investig Allergol Clin Immunol 16(2):79-85 "Safety of specific immunotherapy using a four-hour ultra-rush induction scheme in bee and wasp allergy".
Romaniuk, L.I., "Allergen-specific immunotherapy: mechanisms, methods and efficacy", Clinical Immunology, Allergology and Infectology, 2012, special issue, pp. 44-47. (with English translation of the cited portion).
Rothenberg (2004) J Allergy Clin Immunol 113(1):11-28 "Eosinophilic gastrointestinal disorders (EGID)".
Rothenberg (2009) Gastroenterology 137:1238-1249 "Biology and Treatment of Eosinophilic Esophagitis".
Rothenberg, Marc E. et al., "Intravenous anti-IL-13 mAb QAX576 for the Treatment of eosinophilic esophagitis", Journal of Allergy and Clinical Immunology, vol. 135, No. 2, Feb. 1, 2015, pp. 500-507.
Rudikoff et al. (1982) Proc. Natl. Acad. Sci. 79:1979-1983 "Single amino acid substitution altering antigen-binding specificity".
Russian Official Action from Russian Federation for RU Application 2016104400, mailed Oct. 6, 2017, with translation, 4 pages.
Saeki, Hidehisa, "Guidelines for Management of Atopic Dermatitis", (Advances in Medicine, Special Issue, 2009, vol. 228(1):75-79 in part), cited in the Japanese Patent Application No. 2015-531149.
Sampson et al. (2011) J. Allergy Clin Immunol. 127(5) Letters to the Editor, "A phase II, randomized, double-blind, parallel-group, placebo-controlled oral food challenge trial of Xolair (omalizumab) in peanut allergy", p. 1309-1310.
Sanofi and Regeneron Report Positive Proof-of-Concept Data for Dupilumab, an IL-4R alpha Antibody, in Atopic Dermatitis, 71st Annual Meeting of the American Academy of Dermatology (2013) http://files.shareholder.com/downloads/REGN/2689212012x0x640531/794a7e54-6904-416b-ba38-a4ccc1726852/REGN_News_2013_3_2_General_Releases.pdf.
Sanofi with Regeneron Pharmaceuticals "An Evaluation of Dupilumab in Patients with Nasal Polyposis and Chronic Symptoms of Sinusitis" Trial in Progress, Jun. 2014. ClinicalTrials.gov Identifier: NCT01920893. Retrieved from the Internet URL: http://clinicaltrials.govishow/NCT01920893 Accessed on Sep. 29, 2014.
Sanofi, "Positive Phase 2a Results of Dupilumab in Asthma in the New England Journal of Medicine," May 21, 2013, Regeneron Pharmaceuticals, Inc.
Sanofi/Regeneron Press Release, "Sanofi and Regeneron Report Positive Results with Sarilumab in First Phase 3 Rheumatoid Arthritis Registration Trial", Paris, France and Tarrytown, NY, Nov. 22, 2013, 3 pages.
Sato et al. (1993) J. Immunol. 150(7):2717-2723 "Recombinant soluble murine IL-4 receptor can inhibit or enhance IgE responses in vivo".
Scavuzzo et al. (2005) Biomedicine & Pharmacotherapy 59(6):323-9 "Inflammatory mediators and eosinophilia in atopic and non-atopic patients with nasal polyposis".
Schmidt-Weber (2012) Chem Immunol Allergy 96:120-125 "Anti-IL-4 as a New Strategy in Allergy".
Schmitt et al. (2007) J. of Allergy and Clinical Immunology 120(6):1389-1398 "What are the best outcome measurements for atopic eczema? A systematic review".
Schneider et al. (2013) J. Allergy Clin Immunol 132(6):1368-1374 "A pilot study of omalizumab to facilitate rapid oral desensitization in high-risk peanut-allergic patients".
Sekiya et al. (2002) Allergy 57:173-177 "Increased levels of a TH2-type CC chemokine thymus and activation-regulated chemokine (TARC) in serum and induced sputum of asthmatics".

(56) References Cited

OTHER PUBLICATIONS

Silverberg J.I., et al., "Dupilumab treatment induces rapid clinical improvement of itch in patients with moderate-to-severe atopic dermatitis" Paper presented at: American Academy of Dermatology—76th Annual Meeting; Feb. 16-20, 2018; San Diego, CA, USA.
Silverberg J.I., et al., P481, "Dupilumab treatment rapidly improves itch in patients with moderate-to-severe atopic dermatitis" An Allergy Asthma Immunol. 2017;119 (suppl 5):S95.
Simpson, E.L., et al., "Two Phase 3 Trials of Dupilumab versus Placebo in Atopic Dermatitis," The New England Journal of Medicine, Oct. 1, 2016, DOI: 10.1056/NEJMoa1610020.
Simpson, Eric L. et al., "Dupilumab therapy provides clinically meaningful improvement in patient-reported outcomes (PROs): A phase IIb, randomized, placebo-controlled, clinical trial in adult patients with moderate to severe atopic dermatitis (AD)", Journal of the American Academy of Dermatology, Mosby, Inc., US, vol. 75, No. 3, Jun. 4, 2016.
Simpson, Eric L. et al., "Patient burden of moderate to severe atopic dermatitis (AD): Insights from a phase 2b clinical trial of dupilumab in adults," Journal of the American Academy of Dermatology, Mosby, Inc., US, vol. 74, No. 3, Jan. 14, 2016.
Slager et al. (2012) Journal of Allergy, Asthma and Immunology 130(2):516-522.e4 "IL-4 Receptor Polymorphisms Predict Reduction in Asthma Exacerbations During Response to an Anti IL-4 Receptor Antagonist".
Spirin (1986) Vysshaya shkola, Moscow, pp. 17-23 "Molecular Biology Ribosome structure and protein biosynthesis", original Russian article and English language translation of same provided by foreign associate handling local prosecution of Russian application No. 2011120194.
Stein et al. (2006) J Allergy Clin Immunol 118(6):1312-1319 "Anti-IL-5 (mepolizumab) therapy for eosinophilic esophagitis".
Steinke and Borish (2001) Respiratory Research 2(2):1-5 "Th2 cytokines and asthma Interleukin-4: its role in the pathogenesis of asthma, and targeting it for asthma treatment with interleukin-4 receptor antagonists".
Stone et al. (2008) Clinical & Experimental Allergy 38(12):1858-1865 "Immunomodulatory therapy of eosinophil-associated gastrointestinal diseases".
Strauman (2009) Immunol Allergy Clin N Am 29:11-18 "Clinical Evaluation of the Adult who has Eosinophilic Esophagitis".
Straumann (2005) J Allergy Clin Immunol 115(2):418-419 "Eosinophilic esophagitis: Escalating epidemiology?".
Straumann et al. (2001) J Allergy Clin Immunol 108(6):954-961 "Idiopathic eosinophilic esophagitis is associated with a $T_H2$-type allergic inflammatory response".
Straumann et al. (2009) Gut "Anti-interleukin-5 antibody treatment (mepolizumab) in active eosinophilic oesophagitis: a randomized, placebo-controlled, double-blind trial".
Tazawa et al. (2004) Arch Dermatol Res 295:459-464 "Relative importance of IL-4 and IL-13 in lesional skin of atopic dermatitis".
Tepper et al. (1990) Cell 52:457-467 "IL-4 Induces Allergic-like Inflammatory Disease and Alters T Cell Development in Transgenic Mice".
Terui, et al., "Learning from Fungus Allergy in Atopic Dermatitis Patients," Japan J. Med. Mycol, 2000, vol. 41, No. 3, 157-160.
Thaci, Diamant et al.: "Efficacy and Safety of Dupilumab in Adults with Moderate-to-Severe Atopic Dermatitis Inadequately Controlled by Topical Treatments: A Randomised, placebo-controlled, dose-ranging phase 2b trial," The Lancet, The Lancet Publishing Group, GB, vol. 387, No. 10013, Oct. 8, 2015, pp. 40-52.
Tomkinson et al. (2001) J. Immunol 166:5792-5800 "A Murine IL-4 Receptor Antagonist that Inhibits IL-4- and IL-13—induced Responses Prevents Antigen-Induced Airway Eosinophilia and Airway Hyperresponsiveness".
Tsianakas, Athanasios et al., "Dupilumab: A Milestone in the Treatment of Atopic Dermatitis," The Lancet, The Lancet Publishing Group, GB vol. 387, No. 10013, Oct. 8, 2015.

Ul-Haq, Zaheer et al., "Interleukin-4 receptor signaling and its binding mechanism: A therapeutic insight from inhibitors tool box", Cytokine & Growth Factor Review 32 (2016) 3-15.
Vajdos et al. (2002) Journal of Molecular Biology 320(2):415-428 "Comprehensive functional maps of the antigen-binding site of an anti-ErbB2 antibody obtained with shotgun scanning mutagenesis".
Vakharia, Paras P. et al., "Monoclonal Antibodies for Atopic Dermatitis: Progress and Potential" BioDrugs (2017) 31:409-422.
Veerappan et al. (2009) Clinical Gastroenterology and Hepatology 7:420-426 "Prevalence of Eosinophilic Esophagitis in an Adult Population Undergoing Upper Endoscopy: A Prospective Study".
Vestergaard et al. (2000) The Journal of Investigative Dermatology 115(4):640-646 "A $Th_2$ Chemokine, TARC, Produced by Keratinocytes May Recruit CLA+CCR4+ Lymphocytes into Lesional Atopic Dermatitis Skin".
Virchow et al. (1994) Lung 172:313-334 "Cellular and immunological markers of allergic and intrinsic bronchial asthma".
Walker et al. (1993) Clinical and Experimental Allergy 23:145-153 "Atopic dermatitis: correlation of peripheral blood T cell activation, eosinophilia and serum factors with clinical severity".
Wang and Liu (2008) Current Opinion in Immunology 20:697-702 "The IL-17 cytokine family and their role in allergic inflammation".
Wang, et al., "Peanut-induced intestinal allergy is mediated through a mast cell-IgE-FceRI-IL-13 Pathway," Journal of Allergy and Clinical Immunology, 2010, vol. 126, No. 2, 306-316, e1-e12.
Wark et al. (2006) Advanced Drug Delivery Reviews 58:657-670 "Latest technologies for the enhancement of antibody affinity".
Watson et al. (2011) Allergy, Asthma & Clinical Immunology 7:S4 "Atopic dermatitis".
Weihrauch et al. (2005) Cancer Research 65:5516-5519 "Elevated Serum Levels of CC Thymus and Activation-Related Chemokine (TARC) in Primary Hodgkin's Disease: Potential for a Prognostic Factor".
Weinbrand-Goichberg et al. (2013) Immunol Res "Eosinophilic esophagitis: an immune-mediated esophageal disease".
Wenzel et al. (2007) Lancet 370:1422-1431 "Effect of an interleukin-4 variant on late phase asthmatic response to allergen challenge in asthmatic patients: results of two phase 2a studies".
Wenzel et al. (2010) European Respiratory Society, Annual Congress 2010, "ERS—Programme" pp. 3980.
Wenzel et al. (2013) New England Journal of Medicine 368(26):2455-2466 "Dupilumab in Persistent Asthma with Elevated Eosinophil Levels".
Wershil (2009) Immunol Allergy Clin N Am 29:189-195 "Exploring the Role of Mast Cells in Eosinophilic Esophagitis".
Whalley et al. (2004) British Journal of Dermatology 150:274-283 "A new instrument for assessing quality of life in atopic dermatitis: international development of the Quality of Life Index for Atopic Dermatitis (QoLIAD)".
Wilhelm and Stockinger (2011) Frontiers in Immunology 2(68) "Innate lymphoid cells and type 2 (Th2) mediated immune responses-pathogenic or beneficial?".
Wills-Karp and Finkelman (2008) Science Signaling 1(51) "Untangling the Complex Web of IL-4 and IL-13 Mediated Signaling Pathways".
Winkler et al. (2000) J. Immunol. 165(8):4505-4514 "Changing the Antigen Binding Specificity by Single Point Mutations of an Anti-p24 (HIV-1) Antibody".
Winter and Harris (1993) Immunology Today 14(6):243-246 "Humanized Antibodies".
Wong, et al., "Guidelines for the management of atopic dermatitis (eczema) for pharmacists," CPJ/RPC, Sep./Oct. 2017, vol. 150, No. 5.
Wu et al. (1999) Journal of Molecular Biology 294:151-162 "Humanization of a murine monoclonal antibody by simultaneous optimization of framework and CDR residues".
Yamanaka et al. (2011) Curr Probl Dermatol 41:80-92 "The Role of Cytokines/Chemokines in the Pathogenesis of Atopic Dermatitis".
Yan and Shaffer (2006) World J Gastroenterol 12(15):2328-2334 "Eosinophilic esophagitis: A newly established cause of dysphagia".
Zuo et al. (2010) Journal of Immunology 185:660-669 "IL-13 Induces Esophageal Remodeling and Gene Expression by an Eosinophil-Independent, IL-13R{alpha}2-Inhibited Pathway".

(56) References Cited

OTHER PUBLICATIONS

Zurawski et al. (1995) J. Biol. Chem. Am. Society of Biolochemical Biologists 270(23):13869-13878 "The primary binding subunit of the human Interleukin-4 receptor is also a component of the Interleukin-13 receptor".
Kopp, M.V. et al., "Combination of omalizumab and specific immunotherapy is superior to immunotherapy in patients with seasonal allergic rhinoconjunctivitis and co-morbid seasonal allergic asthma", Clinical and Experimental Allergy, vol. 39, No. 2, pp. 271-279, published on Jan. 22, 2009.
Huang, Evie et al: "Severe Atopic Dermatitis in Children", Current Allergy and Asthma Reports, Current Science, US, vol. 18, No. 6, May 10, 2018, pp. 1-8.
Akinlade, B. et al: "Conjunctivitis in dupilumab clinical trials", British Journal of Dermatology, (Mar. 9, 2019), pp. 1-15.
Paller et al.: "Early and sustained, clinically meaningful responses with dupilumab treatment in a phase 3 trial in adolescents with moderate-to-severe atopic dermatitis", Pediatric Dermatology, vol. 36, No. Suppl. 1, (Apr. 29, 2019), p. S4.
Database Embase [Online], Elsevier Science Publishers, Amsterdam, NL; (May 1, 2019), Cork M. J: "605 Efficacy and safety of dupilumab in adolescent patients with moderate-to-severe atopic dermatitis", XP002793331, Database accession No. EMB-002001809007 abstract.
Database Embase [Online], Elsevier Science Publishers, Amsterdam, NL; (May 1, 2019), Paller, A.S.: "621 Dupilumab in adolescents with moderate-to-severe atopic dermatitis and a history of inadequate response, or intolerance to cyclosporine: subgroup analysis from a pivotal 16-week trial", XP002793332, Database accession No. EMB-002001808313, Abstract.
Regeneron 2011 Annual Report (Apr. 2011), 12 pages.
ClinicalTrials.gov archive, History of Changes for Study: NCT01548404, "Study of Dupilumab in Adult Patients with Extrinsic Moderate-to-Severe Atopic Dermatitis", (Apr. 19, 2012), 7 pages.
ClinicalTrials.gov archive, History of Changes for Study: NCT01259323, "Sequential Ascending Dose Study to Assess the Safety and Tolerability of REGN668 (SAR231893) in Patients With Atopic Dermatitis", (May 31, 2012), 6 pages.
Clinical Trials, Study NCT00676884—"A Phase Study to Investigate the Effects of Repeated Administration of AeroDerm in Subjects with Atopic Dermatitis", Aeroderm first publication of clinical study protocol in TCS resistant moderate-to-severe AD, May 13, 2008, 6 pages.
Clinical Trials, Study NCT01548404—"Study of Dupilumab in Adult Patients with Extrinsic Moderate-to-severe Atopic Dermatitis", final publication of clinical study protocol, Aug. 27, 2015, 8 pages.
Clinical Trials, Study NCT01548404—"Study of REGN668 in Adult Patients With Extrinsic Moderate-to-Severe Atopic Dermatitis", first publication of clinical study protocol, Mar. 7, 2012, 7 pages.
Clinical Trials, Study NCT01639040—"Study to Assess the Safety of REGN668 (SAR231893) Administered Concomitantly with Topical Corticosteroids (TCS) in Patients with Moderate-to-severe Atopic Dermatitis (AD)", Concomitant treatment with TCS, Jul. 11, 2012, 6 pages.
Clinical Trials Study No. NCT01312961—"Efficacy, Safety, and Tolerability of Dupilumab in Patients with Persistent Moderate to Severe Eosinophilic Asthma", In: ClinicalTrials.gov, A service of the U.S. National Institutes of Health, 10 pages, Available from: https://clinicaltrials.gov/ct2/show/NCT01312961.
Chan, L.S. et al., "Expression of Interleukin-4 in the epidermis of transgenic mice results in pruritic inflammatory skin disease: an experimental animal model to study atopic dermatitis", J. Invest. Dermatol., 2001, 117: 977-983.
Phan, N.Q. et al., "Assessment of pruritus intensity: prospective study on validity and reliability of the visual analogue scale, numeric rating scale, and verbal rating scale in 471 patients with chronic pruritis", Acta. Derm. Venereol., 2012, 92: 502-507.

Marone et al., "The Intriguing Role of Interleukin 13 in the Pathophysiology of Asthma", Frontiers in Pharmacology, 2019, pp. 1-3.
Wegmann et al., "Targeting Cytokines in Asthma therapy: could IL-37 be a Solution?", Expert Review of Respiratory Medicine, 2017, vol. 11, No. 9, pp. 675-677.
Nicodeme et al., "Esophageal Distensibility as a Measure of Disease Severity in Patients with Eosinophilic Esophagitis", Clinical Gastroenterology and Hepatology, 2013, vol. 11, No. 9, pp. 1101-1107.
De Genst, Erwin et al., "Antibody repertoire development in camelids", Developmental and Comparative Immunology, 30 (2006); 187-198.
Ward, E. Sally et al., "Blinding activities of a repertoire of single immunoglobin variable domains secreted from *Escherichia coli*", Nature, 1989, 341:544-546.
Barthelemy, Pierre et al., "Comprehensive analysis of the factors contributing to the stability and solubility of autonomous human VH domains", Journal of Biological Chemistry, 2008, 283:3639-3654.
Choi, Yoonjoo et al., "Predicting antibody complementarity determining region structures without classification", Molecular Biosystems, 2011, 7:3327-334.
Griffiths, Andrew et al., "Human anti-self antibodies with high specificity from phage display libraries", The EMBO Journal, 1993, 12:725-734.
Klimka et al., "Human anti-CD30 recombinant antibodies by guided phage antibody selection using cell planning", British Journal of Cancer, 2000, 83:252-260.
Beiboer, Sigrid et al., "Guided selection of a pan carcinoma specific antibody reveals similar binding characteristics yet structural divergence between the original murine antibody and its human equivalent", Journal of Molecular Biology, 2000, 296:833-849.
Darsow, Ulf et al., "Pruritus and Atopic Dermatitis", Clinic Rev Allerg Immunol (2011) 41:237-244.
Buddenkotte, J. et al., "Pathophysiology and therapy of pruritis in allergic and atopic diseases", Allergy 65 (2010), 805-821.
Highlights of Prescribing Information, Dupixent (dupilumab) injection, for subcutaneous use Initial U.S. Approval: 2017, U.S. Food and Drug Administration (FDA), Revised Mar. 2017.
Regeneron: "Dupixent: Highlights of Prescribing Information", (Mar. 1, 2019), pp. 1-8, XP55610296, Retrieved from the Internet: URL: https://dlegnxy4jxlq3f.cloudfront.net/Regeneron/Dupixent_FPI.pdf, 8 pgs.
Regeneron: "Highlights of Prescribing Information See 17 for Patient Counseling Information and FDA-approved patient labeling. Revised: Mar. 2017 Full Prescribing Information: Contents 1 Indications and Usage 2 Dosage and Administration 2.1 Dosage 2.2 Important Administration Instructions 2.3 Preparation for Use", (Apr. 7, 2017), XP055534130, Retrieved from the Internet: URL: https://web.archive.org/web/20170407151633if_/https://www.regeneron.com/sites/default/files/Dupixent_FPI.pdf, 4 pages.
Blankestijn, Mark et al., "Could Duratumumab be used to treat severe allergy?", Journal of Allergy and Clinical Immunology, vol. 139, No. 5, Jan. 19, 2017, p. 1677-1678.e3.
Nagaraju et al., "Bortezomib treatment diminishes hazelnut-induced intestinal anaphylaxis in mice: Immunomodulation", European Journal of Immunology, vol. 46, No. 7, May 11, 2016, pp. 1727-1736.
Winter, Oliver et al., "Pathogenic Long-Lived Plasma Cells and Their Survival Niches in Autoimmunity, Malignancy, and Allergy", The Journal of Immunology, vol. 189, No. 11, Nov. 19, 2012, pp. 5105-5111.
Cork et al., "An open-label phase IIa trial assessing the pharmacokinetics, safety and efficacy of dupilumab in a paediatric population with moderate-to-severe atopic dermatitis", p. 94, British Association of Dermatologists, Jul. 2017, 177 (Suppl. 1), pp. 25-77.
ClinicalTrials.gov Identifier: NTC02407756; Last Update posted Aug. 22, 2016, A Study to Determine the Safety and Tolerability of Dupilumab (REGN668/SAR231893) in Patients Aged >6 to <18 Years With Atopic Dermatitis (Eczema), 11 pages.
Dupixent (dupilumab) Injection, for Subcutaneous Use, Patient Information, Issued Mar. 2017, 34 pages.
Carr, Warner, "Topical Calcineurin Inhibitors for Atopic Dermatitis: Review and Treatment Recommendations", Pediatric Drugs, 2013, vol. 15, pp. 303-310.

(56) References Cited

OTHER PUBLICATIONS

Siegfried et al., "Use of dupilimab in pediatric atopic dermatitis: Access, dosing, and implications for managing severe atopic dermatitis", Pediatric Dermatology, vol. 36, No. 1, Jan. 2019, pp. 172-176.
Paller et al., Abstract, "LB941, Dupilumab for atopic dermatitis in children aged ≥6 to <12 years in phase 3 Liberty Ad Peds trial: Analysis by baseline weight", Journal of Investigative Dermatology (2020) 140: 7 Supplement (B9), Jul. 1, 2020, 1 page.
Paller et al., "Efficacy and safety of dupilumab with concomitant topical corticosteroids in children 6 to 11 years old with severe atopic dermatitis: A randomized, double-blinded, placebo-controlled phase 3 trial", J Am Acad Dermatol, vol. 85, No. 5, Nov. 2020, pp. 1282-1293.
Wenzel et al. (Jul. 2, 2016) "Dupilumab efficacy and safety in adults with uncontrolled persistent asthma despite use of medium-to-high-dose inhaled corticosteroids plus a long-acting beta2 agonist: a randomised double-blind placebo-controlled pivotal phase 2b dose-ranging trial," Lancet. 388:31-44.
Waccholz et al., "Detection of Allergen-Specific IgE Antibody Responses", 2005, Journal of Immunotoxicology, 1:3-4, 189-199.
Janeway, Jr. et al., Immunobiology, 3rd Edition, 1997, Garland Publishing Inc., pp. 11:1-11:22.
Kharkevich, D.A., Pharmacology (Farmakologiya: A Scholarly Manual), 10th Ed., Moscow: GEOTAR-Media, 2010, pp. 73-74 and pp. 846-847, with English translation of cited pages, 12 pages total.
Krasnyuk et al., "Pharmaceutical Technology: Technology of Dosage Forms: A Textbook for College and University Students", 2nd standard edition, Moscow: Akademiya Publishing Center, 2006, p. 8-9, with English translation of cited pages, 7 pages total.
Kim et al., "Engineering of anti-human interleukin-4 receptor alpha antibodies with potent antagonistic activity", Scientific Reports, 2019, vol. 9, Article No. 7772, pp. 1-12.
Radin et al., "First-in-Human Study of REGN668/SAR231893 (IL-4RαmAb): Safety, Tolerability and Biomarker Results of a Randomized, Double-Blind, Placebo-Controlled, Single Ascending Dose Study in Healthy Volunteers", J. Allergy Clin. Immunol., 2013, vol. 131(2), Suppl., p. AB158, (made available on Jan. 26, 2013), 2 pgs.
Celakovska, J. et al., "Sensitization to aeroallergens in atopic dermatitis patients: association with concomitant allergic diseases", JEADV 2015; 29, 1500-1505.
Lucae, S. et al., "IgE responses to exogenous and endogenous allergens in atopic dermatitis patients under long-term systemic cyclosporine A treatment", Allergy 71 (2016); 115-118.
Takashi Yoshike, "Treatment for Atopic Dermatitis", Juntendo Medical Journal, 1999, vol. 45, No. 3, pp. 352-360, 33 pages with English translation.
Manabu Fujimoto, "Oral cyclosporin therapy for atopic dermatitis", Igaku no Ayumi, Journal of Clinical and Experimental Medicine, 2009, vol. 228, No. 1, pp. 98-102, 18 pages with English translation.
Nomura, Ichiro et al., "Staphylococcus aureus and Atopic Dermatitis", (2000), IRYO vol. 54, No. 2, pp. 62-66, 18 pages with English translation.
Hamilton, Jennifer et al., "Dupilumab Normalizes the Eosinophilic Esophagitis Disease Transcriptome in Adult Patients With Eosinophilic Esophagitis", May 1, 2020, Abstract, retrieved from internet on Aug. 5, 2021 at: https://www.sciencedirect.com/science/article/pii/S0016508520327669?via%3Dihub, 1 page.
Reed, Craig, et al., "Patient-reported outcomes in esophageal diseases", Clinical Gastroenterology and Hepatology, Elsevier, Amsterdam, NL, vol. 16. No. 3, pp. 305-310.
Zhang, Yi et al., "Challenges and Considerations for Development of Therapeutic Proteins in Pediatric Patients", Journal of Clinical Pharmacology, 2015, 55 (S3), S103-S115.
Cole, Patrick et al., "Dupilumab. Anti-IL-4Ralpha monoclonal antibody, treatment of atopic dermatitis, treatment of asthma", Drugs of the Future, vol. 40, No. 1, Jan. 1, 2015, pp. 7-13.
Brancaccio, R. et al., "0606: Dupilumab efficacy in different atopic dermatitis phenotypes", Allergy, vol. 75, No. S109, Aug. 1, 2020, p. 442, retrieved from the internet: https://onlinelibrary.wiley/com/doi/10.1111/all.14508.
Tokura et al., "Extrinsic and intrinsic types of atopic dermatitis", Journal of Dermatological Science, Elsevier, vol. 58, No. 1, Apr. 1, 2010, pp. 1-7.
Nettis et al., "Efficacy of dupilumab in atopic comorbidities associated with moderate-to-severe adult atopic dermatitis", Allergy, Wiley-Blackwell Publishing Ltd., UK, vol. 75, No. 10, May 18, 2020, pp. 2653-2661.
Ichiyama, Susumu et al., Letters to the Editor: "Severe atopic dermatitis effectively treated with dupilumab changed from interleukin-5 inhibitors for concomitant severe bronchial asthma", Journal of Dermatology, vol. 48, No. 2, Nov. 8, 2020, pp. e76-e77.
D'Adamio et al., "A life with atopic dermatitis: the patient's point of view after the new hope with dupilumab", Clinical and Experimental Dermatology, Blackwell Scientific Publications, GB, vol. 45, No. 6, May 30, 2020, pp. 809-810.
Boguniewicz, Mark et al., 27406 Abstract: "Dupilumab improves signs and symptoms of severe atopic dermatitis in children aged 6-11 years with or without comorbid asthma", Journal of the American Academy of Dermatology, Mosby, Inc., vol. 85, No. 3, Aug. 7, 2021, 1 page.
Agache, Ioana et al., "EAACI Biologicals Guidelines-dupilumab for children and adults with moderate-to-severe atopic dermatitis", Allergy, Wiley-Blackwell, UK, vol. 76, No. 4, Dec. 27, 2020, pp. 988-1009.
Regeneron: "Dupixent: Highlights of Prescribing Information", Mar. 1, 2019, retrieved from the internet on Aug. 1, 2019 at: https://dlegnxy4jx1q3f.cloudfront.net/Regeneron/Dupixent_FPI.pdf, 13 pages total.
Paller, Amy et al., "The atopic march and atopic multimorbidity: Many trajectories, many pathways", Journal of Allergy and Clinical Immunology, vol. 143, No. 1, Nov. 17, 2018, pp. 46-55.
Czarnowicki, Tali et al., "Novel concepts of prevention and treatment of atopic dermatitis through barrier and immune manipulations with implications for the atopic march", Journal of Allergy and Clinical Immunology, vol. 39, No. 6, Jun. 2, 2017, pp. 1723-1734.
Czarnowicki, Tali et al., "Circulating CLA+ T cells in atopic dermatitis and their possible role as peripheral biomarkers", Allergy, vol. 72, No. 3, Dec. 15, 2016, pp. 366-372.
Clinical Trials, Study NCT00436670, "Phase II Study to Evaluate the Efficacy of AMG 317", first posted Feb. 19, 2007, Amgen actual study completion date—Feb. 2009, 7 pages.
Vincent, M. et al., "Single-Dose, First-in-Human Study of AMG 317: Pharmacokinetics and Safety in Healthy and Asthmatic Adults", the Journal of Allergy and Clinical Immunology, vol. 121, Issue 2, Supplement 1, S10, Abstract, Feb. 1, 2008, 1 page.
Chen, Ching, et al., "Enhancement and destruction of antibody function by somatic mutation: unequal occurrence is controlled by V gene combinatorial associations", The EMBO Journal vol. 15, No. 12, pp. 2784-2794, 1995.
Kussie, Paul, et al., "A Single Engineered Amino Acid Substitution Changes Antibody Fine Specificity", Journal of Immunology:152, pp. 146-152, 1994.
Bergmann, M.M. et al., "Evaluation of Food Allergy in Patients With Atopic Dermatitis", J Allergy Clin Immunol, 1, pp. 22-28, Jan. 1, 2013.
Eichenfield, Lawrence et al., "Guidelines of Care for the Management of Atopic Dermatitis: Part 1: Diagnosis and Assessment of Atopic Dermatitis", Feb. 2014, J. Am. Acad. Dermatol. 70:338-51.
De Bruin-Weller, M. et al., "Dupilumab with concomitant topical corticosteroid treatment in adults with atopic dermatitis with an inadequate response or intolerance to cyclosporin A or when this treatment is medically inadvisable: a placebo-controlled, randomized phase III clinical trial (Liberty Ad Cafe)", British Journal of Dermatology (2018) 178, pp. 1083-1101.
Oosterhaven, Jart et al., "Effect of dupilumab on hand eczema in patients with atopic dermatitis: An observational study", Journal of Dermatology 2019; 46: 680-685.
Voorberg, Angelique et al., "The long-term effect of dupilumab on chronic hand eczema in patients with moderate to severe atopic

(56) References Cited

OTHER PUBLICATIONS dermatitis—52 week results from the Dutch BioDay Registry", Contact Dermatitis, 2022; 87: 185-191.

Voorberg, Angelique et al., "Efficacy and safety of dupilumab in patients with severe chronic hand eczema with inadequate response or intolerance to alitretinoin: a randomized, double-blind, placebo-controlled phase IIb proof-of-concept study", British Journal of Dermatology, 2023; 189: 400-409.

Zirwas, Matthew, "Dupilumab for hand eczema", Research Letters, J Am Acad Dermatol, 2018, vol. 79, No. 1, pp. 167-169.

Waldman, Reid et al., "Dupilumab for the treatment of dyshidrotic eczema in 15 consecutive patients", Research Letters, J Am Acad Dermatol, 2021, vol. 82, vol. 5, pp. 1251-1252.

Weston, Gillian et al., "Dupilumab in the Treatment of Dyshidrosis: A Report of Two Cases", Journal of Drugs in Dermatology, Mar. 2018, vol. 17, Issue 3, pp. 355-356.

Oosterhaven, Jart et al., "Dupilumab Treatment of Very Severe Refractory Atopic Hand Eczema", JAMA Dermatology, vol. 154, No. 8, Aug. 1, 2018, p. 969-70.

Anonymous, ClinicalTrials.gov Record History; ver. 3: Sep. 3, 2021, pp. 1-12, retrieved on Feb. 2, 2024 from https://clinicaltrials.gov/study/NCT03861455?tab=history&a=3, entitled "Efficacy and Safety of Dupilumab Chronic Hands Eczema Refractory to Highly Potent Topical Corticosteroids (Dupeczemain)", last updated Aug. 23, 2023.

Silverberg, Jonathan et al., "Dupilumab provides clinical benefits to patients with atopic dermatitis who do not achieve clear or almost clear skin according to the Investigator's Global Assessment: a pooled analysis of data from two phase III trials", British Journal of Dermatology, John Wiley, UDS, vol. 181, No. 1, Apr. 11, 2019, pp. 80-87.

Clinical Trials.gov Identifier NCT03054428, "Efficacy and Safety of Dupilumab in Participants ≥12 to <18 Years of Age, With Moderate-to-severe Atopic Dermatitis", ClinicalTrials.gov ID NCT03054428, located online on Mar. 4, 2024 at:URL: https://clinicaltrials.gov/study/NCT03054428?term=nct03054428&limit=10&rank=1, 16 pgs.

Akademik, Medical Encyclopedia, "Treatment", located online on Mar. 4, 2024 at: https://dic.academic.ru/dic.nsf/enc_medicine/16487/%D0%9B%D0%B5%D1%87%D0%B5%D0%BD%D0%B8%D0%B5, 8 pages.

Kircik, Leon et al., "Transepidermal water loss (TEWL) and corneometry with hydrogel vehicle in the treatment of atopic dermatitis: a randomized, investigator-blind pilot study", J Drugs Dermatol., 2012, vol. 11(2):180-184 (abstract).

Kamal, Mohamed et al., "The Posology of Dupilumab in Pediatric Patients with Atopic Dermatitis", Clinical Pharmacology and Therapeutics, vol. 110, No. 5, Nov. 2021, pp. 1318-1328.

Simpson, Eric et al., "Efficacy and Safety of Dupilumab in Adolescents With Uncontrolled Moderate to Severe Atopic Dermatitis: A Phase 3 Randomized Clinical Trial", JAMA Dermatol. 2020; 156(1):44-56.

Treister, Alison et al., "Long-term off-label dupilumab in pediatric atopic dermatitis: A case series", Pediatric Dermatology 2019; 36(1):85-88.

Regeneron, "Positive Phase 3 Trial of Dupuxent(R)(Dupilumab) in Adolescents with Inadequately Controlled Moderate-to-Severe Atopic Dermatitis", [online], 2018, <URL: http://investor.regeneron.com/new-releases/news-release-details/positive-phase-3-trial-dupixentr-dupilumab-adolescents/>, searched on Jul. 20, 2024, 6 pages.

\* cited by examiner

METHODS FOR TREATING ATOPIC DERMATITIS BY ADMINISTERING AN IL-4R ANTAGONIST ANTIBODY

CROSS-REFERENCE TO RELATED APPLICATIONS

This application claims priority to United States Provisional Patent Application Nos. 62/882,946, filed Aug. 5, 2019; 62/940,108, filed Nov. 25, 2019; 62/985,715, filed Mar. 5, 2020; 63/024,467, filed May 13, 2020; and 63/032,408, filed May 29, 2020; the contents of each of which are incorporated by reference herein.

SEQUENCE STATEMENT

The instant application contains a Sequence Listing, which has been submitted electronically in ASCII format and is hereby incorporated by reference in its entirety. Said ASCII copy, created on Aug. 4, 2020, is named 40848-0098USU1-SEQLIST.TXT and is 11 kilobytes in size.

FIELD OF THE INVENTION

The present disclosure relates to the use of intereukin-4 receptor (IL-4R) antagonists for treating atopic dermatitis.

BACKGROUND

Atopic dermatitis (AD) is a chronic/relapsing inflammatory skin disease characterized by intense pruritus (i.e., itchiness), xerosis (skin dryness), and eczematous lesions whose features include erythema, infiltration/papulation, oozing with crusting, excoriations, and lichenification. It is often associated with other atopic disorders, such as allergic rhinitis and asthma. Severe disease can be extremely disabling due to several factors: major psychological problems, significant sleep loss, and impaired quality of life (QOL) that lead to a high socioeconomic cost. An estimated 2% to 10% of adults are affected by AD (Bieber 2008, *N. Engl. J. Med.* 358:1483-94).

AD is the most common inflammatory skin disease in childhood (Illi et al 2004, *J. Allergy Clin. Immunol.* 113: 925-31). The disease usually presents during early infancy and childhood, but it can persist into or start in adulthood (Kay et al 1994, *J. Am. Acad. Dermatol.* 30: 35-9). The disease affects 15 to 30% of children and 2 to 10% of adults in industrialized countries (Bieber 2008, *N. Engl. J. Med.* 358: 1483-94). Phase 1 of the International Study of Asthma and Allergies in Childhood showed a 1-year period prevalence rate as high as 20% in Australia, England, and Scandinavia (Williams et al 1999, *J. Allergy Clin. Immunol.* 103:125-38). Often AD constitutes the first step of atopic march (progression from one atopic disease to another). Approximately up to 60% of AD patients have concomitant asthma or allergic rhinitis or food allergy (Hong et al 2012, *Envt. Health Toxicol.* 27: e2012006).

The clinical pattern of AD varies with age. Infants typically present with erythematous papules and vesicles on the cheeks, forehead, or scalp, which are exudative and intensely pruritic. The childhood phase typically occurs from 2 years of age to puberty. Children are less likely to have the exudative lesions of infancy, and instead exhibit more lichenifled papules and plaques representing the more chronic disease involving the hands, feet, wrists, ankles, and antecubital and popliteal regions. The adult phase of AD begins at puberty and frequently continues into adulthood. Predominant areas of involvement include the flexural folds, the face and neck, the upper arms and back, and the dorsa of the hands, feet, fingers, and toes. The eruption is characterized by dry, scaling erythematous papules and plaques, and the formation of large lichenified plaques from lesional chronicity.

The disease has been shown to have a marked impact on the quality of life (QOL) of patients, greater than that seen in other common skin disorders like psoriasis and acne (Lewis-Jones et al 1995, *Brit. J. Dermatol.* 132: 942-9). Often severe, pruritus is a universal finding in AD and often results in sleep disruption, irritability, and generalized stress for both the affected patients as well as family members (Kim et al 2012, *J. Kor. Med. Sci.* 27:1327-32). In addition to causing discomfort, sleep loss, and psychosocial challenges, AD can impose major financial burdens on families for direct medical care, household accommodations, and missed work (Su et al 1997, *Arch. Dis. Child.* 76: 159-62; Verboom et al 2002, *Brit. J. Dermatol.* 147: 716-24; Williams 2005, *New Engl. J. Med.* 352: 2314-24).

Of particular interest in children is the phenomenon of "Atopic March" which is characterized by a typical sequence of progression of clinical signs of atopic disease. In general, the clinical signs of AD and of food allergies predate the development of asthma and allergic rhinitis, suggesting that AD is an "entry point" for subsequent allergic disease (Spergel 2003, *J Allergy Clin Immunol.* 112(6 Suppl):S118-27). Severity of AD is correlated with development of asthma and allergic rhinitis (Zheng 2011, *Allergy Asthma Immunol Res.* 3(2):67-73). The prevalence of asthma in children 6 years and older who had developed eczema during the first 4 years of their life has been estimated to be around 35% (Van der Hulst 2007, *J Allergy Clin Immunol.* 120(3):565-9). In a prospective study on 'Atopic March' in which children with eczema during infancy were followed, 47% of patients had allergic rhino-conjunctivitis and 29% had asthma (Ekback 2014, *PLoS One.* 9(6):e99609) by the age of 10 years. More severe skin disease is directly correlated with a higher risk of developing comorbidities (asthma, allergic rhinitis, food allergy, and mental health disorders) and is associated with more severe comorbidities (Silverberg 2013, *Pediatr Allergy Immunol.* 24(5):476-86). The incidence of mental health disorders like anxiety, depression, and Attention Deficit Hyperactivity Disorder (ADHD) is also higher in children with AD (Yaghmaie 2013, *J Allegy Clin Immunol.* 131(2):428-33). The course of the disease in school-going children can be complicated by potentially life-threatening complications like eczema herpeticum (Luca 2012, *Pediatr.* 161(4):671-5).

Non-pharmacological management of AD, which includes environmental control measures (e.g., avoidance of antigen and skin irritants) and skin care measures (e.g., maintaining the hydration of the skin through the use of emollients) play a supportive role, especially in children with moderate-to-severe disease. Pharmacological management of AD in children is mainly limited to topical therapy with topical corticosteroids (TCS) and topical calcineurin inhibitors (TCIs). However, long-term use of TCS in children is not recommended because of the risk of irreversible skin atrophy, dyspigmentation, acneiform eruptions, and risks associated with systemic absorption (e.g., growth retardation, hypothalamic pituitary axis effects, etc.). Topical calcineurin inhibitors, such as tacrolimus and pimecrolimus, are also used in AD as an alternative to or in combination with TCS. The more effective TCI products (e.g., tacrolimus 0.1%) are not approved for use in children aged 6 to 11 years old. Moreover, the use of TCI is frequently associated with skin irritation. Furthermore, a possible increased risk of malignancy (lymphoma and skin cancers) has been noted for TCIs.

Systemic agents are used off-label in children aged 6 to 11 years old (cyclosporine, systemic steroids, methotrexate, azathioprine, and mycophenolate mofetil). A recent survey conducted in Europe, "European TREatment of Severe Atopic Eczema in Children Taskforce (TREAT)" found that approximately 70% of respondents initiated systemic therapy for children with severe AD (Proudfoot 2013, *Br J Dermatol.* 169(4):901-9). All of these systemic agents have significant side effects in children, including stunted growth, diabetes, cutaneous atrophy, hypertension, osteoporosis, and rebound exacerbation after discontinuation (corticosteroids), myelosuppression and hepatotoxicity (methotrexate), nephrotoxicity and hypertension (cyclosporine), increased risk of malignancies (cyclosporine, azathioprine), and gastrointestinal disturbances and leucopenia (azathioprine). Moreover, a high proportion of patients in which disease is initially controlled by systemic agents suffer from relapse soon after therapy is discontinued (Schmitt 2009, *Brit J Dermatol*; journal compilation: 1-8).

Accordingly, currently there is a high, unmet medical need for a safe and effective therapy for AD in children.

SUMMARY

In one aspect, methods for treating atopic dermatitis (AD) or improving an AD-associated parameter in a subject are provided. In some embodiments, the method comprises administering to a pediatric subject having moderate-to-severe or severe AD, wherein the subject is ≥6 years to <12 years of age, one or more doses of an interleukin-4 receptor (IL-4R) antagonist. In some embodiments, the IL-4R antagonist is an anti-IL-4R antibody, or an antigen-binding fragment thereof.

In some embodiments, the method comprises:
(a) selecting a subject with severe AD, wherein the subject is ≥6 years to <12 years of age; and
(b) administering to the subject one or more doses of an interleukin-4 receptor (IL-4R) antagonist, wherein the IL-4R antagonist is an anti-IL-4R antibody, or an antigen-binding fragment thereof, that comprises the heavy chain complementarity determining regions (HCDRs) of a heavy chain variable region (HCVR) comprising the amino acid sequence of SEQ ID NO:1 and the light chain complementarity determining regions (LCDRs) of a light chain variable region (LCVR) comprising the amino acid sequence of SEQ ID NO:2.

In some embodiments, the subject is a subject with severe AD that cannot be adequately controlled with topical AD medications or for whom topical treatment is medically inadvisable. In some embodiments, the subject is inadequately responsive to treatment with a topical corticosteroid (TCS). In some embodiments, the subject is a subject with severe AD who is a candidate for systemic therapy.

In some embodiments, the subject:
(i) has a baseline Investigator's Global Assessment (IGA) score≥4;
(ii) has a baseline Eczema Area and Severity Index (EASI) score ≥21;
(iii) has a baseline Body Surface Area (BSA) affected by AD ≥15%; and/or
(iv) has chronic AD diagnosed at least one year prior to the onset of treatment.

In some embodiments, the subject:
(i) has a baseline Investigator's Global Assessment (IGA) score=4;
(ii) has a baseline Eczema Area and Severity Index (EASI) score ≥21;
(iii) has a baseline Body Surface Area (BSA) affected by AD ≥15%; and/or
(iv) has chronic AD diagnosed at least one year prior to the onset of treatment.

In some embodiments, the subject has at least one concurrent allergic condition. In some embodiments, the subject has a concurrent allergic condition selected from the group consisting of allergic rhinitis, asthma, food allergy, allergic conjunctivitis, hives, chronic rhinosinusitis, nasal polyps, and eosinophilic esophagitis.

In some embodiments, the IL-4R antagonist is subcutaneously administered at an initial dose followed by one or more secondary doses, wherein each secondary dose is administered 1 to 4 weeks after the immediately preceding dose. In some embodiments, the IL-4R antagonist is subcutaneously administered at an initial dose followed by one or more secondary doses, wherein each secondary dose is administered 1 to 4 weeks after the immediately preceding dose, wherein:
(i) for a subject having a body weight of <30 kg, the initial dose of the IL-4R antagonist is 200 mg and each secondary dose is 100 mg; or
(ii) for a subject having a body weight of ≥30 kg, the initial dose of the IL-4R antagonist is 400 mg and each secondary dose is 200 mg; or
(iii) the initial dose of the IL-4R antagonist is 600 mg and each secondary dose is 300 mg.

In some embodiments, the subject has a body weight of <30 kg and the IL-4R antagonist is administered at an initial dose of 200 mg followed by one or more secondary doses of 100 mg every two weeks (Q2W). In some embodiments, the subject has a body weight of ≥230 kg and the IL-4R antagonist is administered at an initial dose of 400 mg followed by one or more secondary doses of 200 mg every two weeks (Q2W). In some embodiments, the IL-4R antagonist is administered at an initial dose of 600 mg followed by one or more secondary doses of 300 mg every four weeks (Q4W).

In some embodiments, the IL-4R antagonist is subcutaneously administered at an initial dose followed by one or more secondary doses, wherein:
(i) for a subject having a body weight of <30 kg, the IL-4R antagonist is administered at an initial dose of 600 mg followed by one or more secondary doses of 300 mg Q4W; or
(ii) for a subject having a body weight of ≥30 kg to <60 kg, the IL-4R antagonist is administered at an initial dose of 400 mg followed by one or more secondary doses of 200 mg Q2W; or
(iii) for a subject having a body weight of ≥60 kg, the IL-4R antagonist is administered at an initial dose of 600 mg followed by one or more secondary doses of 300 mg Q2W.

In some embodiments, the subject has a body weight of <30 kg and the IL-4R antagonist is administered at an initial dose of 600 mg followed by one or more secondary doses of 300 mg Q4W. In some embodiments, the subject has a body weight of ≥15 kg to <30 kg and the IL-4R antagonist is administered at an initial dose of 600 mg followed by one or more secondary doses of 300 mg Q4W. In some embodiments, the subject has a body weight of ≥30 kg to <60 kg and the IL-4R antagonist is administered at an initial dose of 400 mg followed by one or more secondary doses of 200 mg Q2W. In some embodiments, the subject has a body weight of ≥60 kg and the IL-4R antagonist is administered at an initial dose of 600 mg followed by one or more secondary doses of 300 mg Q2W.

In some embodiments, the IL-4R antagonist is subcutaneously administered at a dose of about 50 mg to about 600 mg, with or without an initial or loading dose. In some embodiments, the IL-4R antagonist is administered to a subject (e.g., a subject having a body weight of <30 kg or a subject having a body weight of ≥15 kg to <30 kg) at a dose of 100 mg Q2W, with or without an initial or loading dose. In some embodiments, the IL-4R antagonist is administered to a subject (e.g., a subject having a body weight of ≥30 kg or a subject having a body weight of ≥30 kg to <60 kg) at a dose of 200 mg Q2W, with or without an initial or loading dose. In some embodiments, the IL-4R antagonist is administered to a subject (e.g., a subject having a body weight of <30 kg or a subject having a body weight of ≥15 kg to <30 kg) at a dose of 300 mg Q4W, with or without an initial or loading dose. In some embodiments, the IL-4R antagonist is administered to a subject (e.g., a subject having a body weight of ≥60 kg) at a dose of 300 mg Q2W, with or without an initial or loading dose.

In some embodiments, the IL-4R antagonist is subcutaneously administered at a dose of about 50 mg to about 600 mg, with an initial or loading dose that is administered as a "split dose," e.g., on two or more separate days. In some embodiments, the initial or loading dose is administered as a split dose over the course of about one week, about two weeks, about three weeks, or about four weeks. In some embodiments, the IL-4R antagonist is administered to a subject at an initial dose of 600 mg, wherein the initial dose is split into two or more doses (e.g., a first 300 mg dose and a second 300 mg dose) followed by one or more secondary doses of 300 mg Q4W. In some embodiments, the IL-4R antagonist is administered to a subject at an initial dose of 400 mg, wherein the initial dose is split into two or more doses (e.g., a first 200 mg dose and a second 200 mg dose) followed by one or more secondary doses of 200 mg Q2W. In some embodiments, the IL-4R antagonist is administered to a subject at an initial dose of 600 mg, wherein the initial dose is split into two or more doses (e.g., a first 300 mg dose and a second 300 mg dose) followed by one or more secondary doses of 300 mg Q2W. In some embodiments, part of the initial dose is administered on Day 1, then the remainder of the initial dose is administered one week later, two weeks later, three weeks later, or four weeks later, followed by one or more secondary doses after the remainder of the initial dose is administered. In some embodiments, part of the initial dose is administered on Day 1, then the remainder of the initial dose is administered on Day 8 (after one week), on Day 15 (after two weeks), or on Day 22 (after three weeks), followed by one or more secondary doses after the remainder of the initial dose is administered.

In some embodiments, the IL-4R antagonist is administered to a subject at an initial dose of 300 mg on Day 1, then 300 mg on Day 15 (Week 2), then after Day 15, subsequent doses are administered at a dose of 300 mg Q4W. In some embodiments, the IL-4R antagonist is administered to a subject having a body weight of <30 kg or a subject having a body weight of ≥15 kg to <30 kg at an initial dose of 300 mg on Day 1 then 300 mg two weeks later, then subsequent doses are administered at 300 mg Q4W. In some embodiments, the IL-4R antagonist is administered to a subject having a body weight of <30 kg or a subject having a body weight of ≥15 kg to <30 kg at an initial dose of 300 mg on Day 1, then 300 mg on Day 15 (Week 2), then after Day 15, is administered at a dose of 300 mg Q4W.

In some embodiments, the IL-4R antagonist is administered to a subject at a dose of 300 mg Q4W, with an extra dose administered at Week 2 (e.g., Day 15). In some embodiments, the IL-4R antagonist is administered to a subject having a body weight of <30 kg or a subject having a body weight of ≥15 kg to <30 kg at a dose of 300 mg Q4W, with an extra dose administered at Week 2 (e.g., Day 15).

In some embodiments, the IL-4R antagonist is administered to a subject at an initial dose of 300 mg, then starting 2 weeks after the initial dose, is administered at a dose of 300 mg Q4W. In some embodiments, the IL-4R antagonist is administered to a subject having a body weight of <30 kg or a subject having a body weight of ≥15 kg to <30 kg at an initial dose of 300 mg, then starting 2 weeks after the initial dose, is administered at a dose of 300 mg Q4W.

In some embodiments, the IL-4R antagonist (e.g., an anti-IL-4R antibody or an antigen-binding fragment thereof) is administered to a subject (e.g., a subject ≥6 years to <12 years of age having moderate-to-severe or severe AD who is a candidate for systemic therapy) at a dose of 300 mg Q4W. In some embodiments, an initial or loading dose of about 400 mg or about 600 mg of the IL-4R antagonist is administered. In some embodiments, no initial or loading dose is administered. In some embodiments, a split loading dose is administered.

In some embodiments, the IL-4R antagonist (e.g., an anti-IL-4R antibody or an antigen-binding fragment thereof) is administered to a subject (e.g., a subject ≥6 years to <12 years of age having moderate-to-severe or severe AD who is a candidate for systemic therapy) at a dose of 300 mg Q4W if the subject has a body weight of ≥15 kg to <30 kg, or at a dose of 200 mg Q2W if the subject has a body weight of ≥30 kg to <60 kg, or at a dose of 300 mg Q2W if the subject has a body weight of ≥60 kg. In some embodiments, an initial or loading dose of about 400 mg or about 600 mg of the IL-4R antagonist is administered. In some embodiments, no initial or loading dose is administered. In some embodiments, a split loading dose is administered.

In some embodiments, the IL-4R antagonist (e.g., an anti-IL-4R antibody or an antigen-binding fragment thereof) is administered to a subject (e.g., a subject ≥6 years to <12 years of age having moderate-to-severe or severe AD who is a candidate for systemic therapy) at a dose of 200 mg QW or 300 mg QW if the subject has a body weight of ≥60 kg.

In some embodiments, the subject is administered the IL-4R antagonist in combination with a topical medication (e.g., a topical corticosteroid (TCS) or a topical nonsteroidal medication). In some embodiments, the subject is administered the IL-4R antagonist in combination with a TCS. In some embodiments, the TCS is a medium-potency TCS. In some embodiments, the TCS is a low-potency TCS. In some embodiments, treatment with the IL-4R antagonist reduces the amount of TCS that is administered to the subject relative to baseline.

In some embodiments, treatment with the IL-4R antagonist results improves an AD-associated parameter that is selected from:
  (i) a reduction from baseline in IGA score to achieve an IGA score of 0 or 1 by week 16 after administration of the first dose of the IL-4R antagonist; and
  (ii) a reduction of at least 75% from baseline in an EASI score (EASI-75) by week 16 after administration of the first dose of the IL-4R antagonist.

In some embodiments, the IL-4R antagonist is an anti-IL-4R antibody, or an antigen-binding fragment thereof, that specifically binds IL-4R. In some embodiments, the anti-IL-4R antibody or antigen-binding fragment thereof comprises the heavy chain complementarity determining regions (HCDRs) of a heavy chain variable region (HCVR) comprising the amino acid sequence of SEQ ID NO:1 and the light chain complementarity determining regions (LCDRs) of a light chain variable region (LCVR) comprising the amino acid sequence of SEQ ID NO:2. In some embodiments, the anti-IL-4R antibody or antigen-binding fragment thereof comprises a HCVR comprising the amino acid sequence of SEQ ID NO:1 and comprises a LCVR comprising the amino acid sequence of SEQ ID NO:2. In some embodiments, the anti-IL-4R antibody comprises a heavy chain comprising the amino acid sequence of SEQ ID NO:9 and a light chain comprising the amino acid sequence of SEQ ID NO:10. In some embodiments, the IL-4R antagonist is dupilumab or a bioequivalent thereof.

In some embodiments, a method for treating AD or improving an AD-associated parameter in a subject comprises administering an IL-4R antagonist to a subject with moderate-to-severe or severe AD, wherein the subject is ≥6 years to <12 years of age, wherein the IL-4R antagonist is an anti-IL-4R antibody, or an antigen-binding fragment thereof, that specifically binds IL-4R and that comprises three HCDRs (HCDR1, HCDR2 and HCDR3) and three LCDRs (LCDR1, LCDR2 and LCDR3), wherein the HCDR1 comprises the amino acid sequence of SEQ ID NO:3, the HCDR2 comprises the amino acid sequence of SEQ ID NO:4, the HCDR3 comprises the amino acid sequence of SEQ ID NO:5, the LCDR1 comprises the amino acid sequence of SEQ ID NO:6, the LCDR2 comprises the amino acid sequence of SEQ ID NO:7, and the LCDR3 comprises the amino acid sequence of SEQ ID NO:8; wherein the IL-4R antagonist is subcutaneously administered at an initial dose followed by one or more secondary doses, wherein:
  (i) for a subject having a body weight of ≥15 kg to <30 kg, the IL-4R antagonist is administered at an initial dose of 600 mg followed by one or more secondary doses of 300 mg Q4W; or
  (ii) for a subject having a body weight of ≥30 kg to <60 kg, the IL-4R antagonist is administered at an initial dose of 400 mg followed by one or more secondary doses of 200 mg Q2W; or
  (iii) for a subject having a body weight of ≥60 kg, the IL-4R antagonist is administered at an initial dose of 600 mg followed by one or more secondary doses of 300 mg Q2W.

In some embodiments, the subject is concomitantly administered a topical medication (e.g., a topical corticosteroid (TCS) or a topical nonsteroidal medication, such as a calcineurin inhibitor or crisaborole). In some embodiments, the subject is concomitantly administered a TCS. In some embodiments, the TCS is a medium-potency TCS. In some embodiments, the TCS is a low-potency TCS.

In some embodiments, methods for treating AD or improving an AD-associated parameter in a subject are provided, wherein the subject is ≥6 years to <18 years of age and has moderate-to-severe or severe AD, wherein the method comprises administering to the subject an anti-IL-4R antibody, or an antigen-binding fragment thereof, that comprises the HCDRs of a HCVR comprising the amino acid sequence of SEQ ID NO:1 and the LCDRs of a LCVR comprising the amino acid sequence of SEQ ID NO:2; wherein:
  (i) for a subject having a body weight of ≥15 kg to <30 kg, the anti-IL-4R antibody or antigen-binding fragment thereof is administered at an initial dose of 600 mg followed by one or more secondary doses of 300 mg Q4W; or
  (ii) for a subject having a body weight of ≥30 kg to <60 kg, the anti-IL-4R antibody or antigen-binding fragment thereof is administered at an initial dose of 400 mg followed by one or more secondary doses of 200 mg Q2W; or
  (iii) for a subject having a body weight of ≥60 kg, the anti-IL-4R antibody or antigen-binding fragment thereof is administered at an initial dose of 600 mg followed by one or more secondary doses of 300 mg Q2W.

In some embodiments, the subject is ≥6 years to <12 years of age. In some embodiments, the subject has severe AD. In some embodiments, the subject is a candidate for systemic therapy.

In some embodiments, the IL-4R antagonist (e.g., an anti-IL-4R antibody, or antigen-binding fragment thereof, as disclosed herein) is contained in a container selected from the group consisting of a glass vial, a syringe, a pre-filled syringe, a pen delivery device, and an autoinjector. In some embodiments, the IL-4R antagonist is contained in a pre-filled syringe. In some embodiments, the pre-filled syringe is a single-dose pre-filled syringe. In some embodiments, the IL-4R antagonist is contained in an autoinjector. In some embodiments, the IL-4R antagonist is contained in a pen delivery device (e.g., a pre-filled pen).

In another aspect, therapeutic dosage forms of a pharmaceutical composition comprising an IL-4R antagonist are provided. In some embodiments, the therapeutic dose of the IL-4R antagonist is 2 mg/kg, and weekly administration of the dosage form for four weeks to a subject provides a mean serum concentration of the IL-4R antagonist of 74 (±20) mg/L. In some embodiments, the therapeutic dose of the IL-4R antagonist is 2 mg/kg, and weekly administration of the dosage form for at least 24 weeks to a subject provides a mean serum concentration of the IL-4R antagonist of about 61 mg/L to about 77 mg/L. In some embodiments, the therapeutic dose of the IL-4R antagonist is 4 mg/kg, and weekly administration of the dosage form for four weeks to a subject provides a mean serum concentration of the IL-4R antagonist of 161 (±60) mg/L. In some embodiments, the therapeutic dose of the IL-4R antagonist is 4 mg/kg, and weekly administration of the dosage form for at least 24 weeks to a subject provides a mean serum concentration of the IL-4R antagonist of about 143 mg/L to about 181 mg/L. In some embodiments, the mean serum concentration of the IL-4R antagonist is maintained for at least 48 weeks, when the therapeutic dosage form is administered weekly.

In some embodiments, a therapeutic dosage form of a pharmaceutical composition comprises an IL-4R antagonist, and administration of the dosage form for 16 weeks to a subject provides a mean serum concentration of the IL-4R antagonist of 80-100 mg/L. In some embodiments, the therapeutic dose of the IL-4R antagonist is 200 mg administered every two weeks. In some embodiments, the therapeutic dose of the IL-4R antagonist is 300 mg administered every four weeks.

In some embodiments, the therapeutic dosage form is administered to a subject ≥6 years to <18 years of age. In some embodiments, the subject is ≥6 years to <12 years of age. In some embodiments, the subject is ≥12 years to <18 years of age.

In some embodiments, the therapeutic dosage form comprises an IL-4R antagonist that is an anti-IL-4R antibody or antigen-binding fragment thereof that comprises an HCDR1 comprising the amino acid sequence of SEQ ID NO:3, an HCDR2 comprising the amino acid sequence of SEQ ID NO:4, an HCDR3 comprising the amino acid sequence of SEQ ID NO:5, an LCDR1 comprising the amino acid sequence of SEQ ID NO:6, an LCDR2 comprising the amino acid sequence of SEQ ID NO:7, and an LCDR3 comprising the amino acid sequence of SEQ ID NO:8.

Other embodiments will be apparent from a review of the ensuing detailed description.

BRIEF DESCRIPTION OF THE FIGURES

FIG. 4A: Phase 2a study. Vertical arrows represent time points at which dupilumab 2 mg/kg or 4 mg/kg was administered. FIG. 4B: Phase 3 OLE. Patients in the OLE received dupilumab 2 mg/kg weekly or 4 mg/kg weekly. $C_{max}$, maximum concentration; LLOQ, lower limit of quantification; SD, standard deviation; $t_{max}$, time to achieve maximum concentration.

FIG. 5A: Concentration-time profile of the Phase 2a study. Vertical arrows represent time points at which dupilumab 2 mg/kg or 4 mg/kg was administered.

FIG. 5B: Concentration-time profile of the Phase 3 OLE study. For both (A) and (B), concentrations below the limit of quantitation were set as LLOQ/2 (represented as a dotted line).

DETAILED DESCRIPTION

Figures 1A, 1B, 1C:
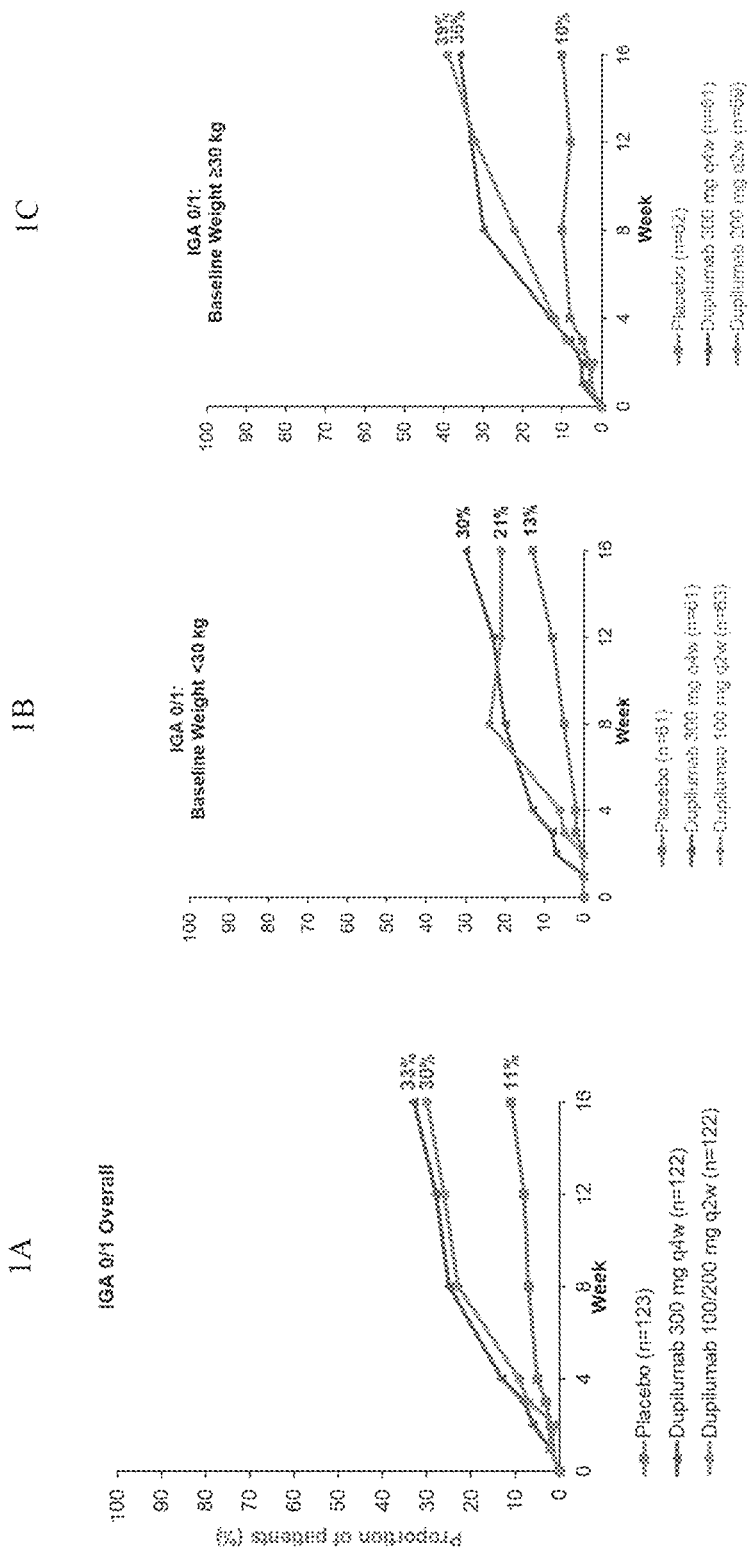
FIGS. 1A-1I. Proportion of patients achieving specified endpoints over time in the overall population and the baseline weight <30 kg, and ≥30 kg subgroups. (A-C) Proportion of patients achieving the co-primary endpoint of IGA 0/1 over time in the overall population (A), in the baseline weight <30 kg subgroup (B), and in the ≥30 kg subgroup (C). (D-F) Percentage of patients achieving the co-primary endpoint of EASI-75 over time in the overall population (D), in the baseline weight <30 kg subgroup (E), and in the ≥30 kg subgroup (F). (G-I) The least square (LS) percent change in EASI over time in the overall population (G), in the baseline weight <30 kg subgroup (H), and in the ≥30 kg subgroup (1). EASI=Eczema Area and Severity Index; EASI-75=≥75% improvement from baseline in EASI scores; IGA=Investigator's Global Assessment; LS=least-squares; Q2W=every 2 weeks; Q4W=every 4 weeks.

Before the present invention is described, it is to be understood that the invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

The terms "FIG.", "FIGS.", "Figure", and "Figures" are used interchangeably herein.

As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

As used herein, the terms "treat," "treating," or the like, mean to alleviate symptoms, eliminate the causation of symptoms either on a temporary or permanent basis, or to prevent or slow the appearance of symptoms of the named disorder or condition.

"Atopic dermatitis" or "AD", as used herein, means an inflammatory skin disease characterized by intense pruritus (e.g., severe itch) and by scaly and dry eczematous lesions. The term "atopic dermatitis" includes, but is not limited to, AD caused by or associated with epidermal barrier dysfunction, allergy (e.g., allergy to certain foods, pollen, mold, dust mite, animals, etc.), radiation exposure, and/or asthma. The present disclosure encompasses methods to treat patients with moderate-to-severe or severe AD. As used herein, "moderate-to-severe AD" is characterized by intensely pruritic, widespread skin lesions that are often complicated by persistent bacterial, viral or fungal infections. Moderate-to-severe AD also includes chronic AD in patients. In many cases, the chronic lesions include thickened plaques of skin, lichenification and fibrous papules. Patients affected by moderate-to-severe AD also, in general, have more than 20% of the body's skin affected, or 10% of skin area in addition to involvement of the eyes, hands and body folds. Moderate-to-severe AD is also considered to be present in patients who require frequent treatment with topical corticosteroids. A patient may also be said to have moderate-to-severe AD when the patient is resistant or refractory to treatment by either a topical corticosteroid or a calcineurin inhibitor. As used herein, "severe AD" is characterized by the presence of widespread skin lesions, unremitting itching, or physically or emotionally disabling disease that significantly compromises a patient's quality of life. In some cases, patients with severe AD also exhibits one or more symptoms such as excoriation, extensive skin thickening, bleeding, oozing, and/or cracking of skin, and alteration of pigmentation. In some embodiments, severe AD is refractory to treatment by a topical therapy (e.g., a topical corticosteroid, calcineurin inhibitor, crisaborole, or phototherapy).

As used herein, the term "subject in need thereof" refers to a human or non-human animal having AD (e.g., moderate-to-severe AD or severe AD). In some embodiments, the term "a subject in need thereof" refers to patients with moderate-to-severe or severe AD, wherein the patient is ≥12 and <18 years of age (adolescents). In other embodiments, the term "a subject in need thereof" refers to patients with moderate-to-severe or severe AD, wherein the patient is ≥6 and <12 years of age (children). The terms "subject" and "patient" are used interchangeably herein.

In some embodiments, the term "subject in need thereof" includes patients with moderate-to-severe or severe AD who are 6 to 18 years of age (e.g., adolescent patients ≥12 and <18 years of age or pediatric patients ≥6 and <12 years of age) and who are candidates for systemic therapy. In some embodiments, a subject is a candidate for systemic therapy if the subject's disease is not adequately controlled with topical therapy, and/or if topical therapy is not advisable (e.g., due to safety concerns). In some embodiments, the term "subject in need thereof" includes patients with moderate-to-severe or severe AD who are 6 to 18 years of age (e.g., adolescent patients ≥12 and <18 years of age or pediatric patients ≥6 and <12 years of age) and who have received prior treatment with systemic therapy. As used herein, the term "systemic therapy" refers to systemically administered therapeutic agents (e.g., orally administered corticosteroids). The term includes systemic immunosuppressant or immunomodulatory agents. In the context of the present disclosure, the term "systemic immunosuppressant" includes, but is not limited to, cyclosporine A, methotrexate, mycophenolate mofetil, azathioprine, systemic or oral corticosteroids, and interferon-gamma. In certain embodiments, the term also includes immunobiologics such as tumor necrosis factor alpha (TNFα) inhibitors (e.g., an anti-TNFα antibody such as infliximab), CD11a inhibitors (e.g., an anti-CD11a antibody such as efalizumab), IgE inhibitors (e.g., omalizumab), CD20 inhibitors (e.g., rituximab). Systemic therapy including systemic immunosuppressants may be used for short-term treatment of flares or as a temporary measure to control disease, but their use is limited by significant side effects, e.g., growth retardation in children, Cushing's syndrome, hypertension, glucose intolerance, myopathy, osteonecrosis, glaucoma and cataracts. Use of systemic immunosuppressants also carries the risk of rebound phenomenon, wherein symptoms of the disease may worsen significantly following cessation of treatment. In certain embodiments, the terms "systemic therapy", "systemic therapeutic agent" and "systemic immunosuppressant" have been used interchangeably throughout this disclosure.

The term "TCS," as used herein, includes group I, group II, group III and group IV topical corticosteroids. According to the Anatomical Therapeutic Classification System of World Health Organization, the corticosteroids are classified as weak (group 1), moderately potent (Group II) and potent (Group III) and very potent (Group IV), based on their activity as compared to hydrocortisone. Group IV TCS (very potent) are up to 600 times as potent as hydrocortisone and include clobetasol propionate and halcinonide. Group III TCS (potent) are 50 to 100 times as potent as hydrocortisone and include, but are not limited to, betamethasone valerate, betamethasone dipropionate, diflucortolone valerate, hydrocortisone-17-butyrate, mometasone furoate, and methylprednisolone aceponate. Group II TCS (moderately potent; also referred to interchangeably herein as "medium potency") are 2 to 25 times as potent as hydrocortisone and include, but are not limited to, clobetasone butyrate, and triamcinolone acetonide. Group I TCS (mild; also referred to interchangeably herein as "low potency") includes hydrocortisone.

Although any methods and materials similar or equivalent to those described herein can be used in the practice of the disclosure, the typical methods and materials are now described. All publications mentioned herein are incorporated herein by reference in their entirety.

Therapeutic Methods

In one aspect, methods for treating atopic dermatitis (AD) or improving an AD-associated parameter in a subject are provided. In some embodiments, the methods comprise administering to a subject having severe AD, wherein the subject is ≥6 years to <12 years of age, one or more doses of an intereukin-4 receptor (IL-4R) antagonist. In some embodiments, the IL-4R antagonist is administered concomitantly with topical therapy for AD, such as a topical corticosteroid (TCS) or a topical nonsteroidal medication (e.g., a calcineurin inhibitor or crisaborole).

In some embodiments, a subject to be treated according to the methods disclosed herein is a subject ≥6 years to <12 years old who has severe AD that is inadequately responsive to topical therapies (e.g., TCS with or without topical calcineurin inhibitors (TCIs)) or for whom topical therapy is inadvisable (e.g., due to adverse side effects or safety risks). In some embodiments, the subject has a documented history of inadequate response to a sufficient course of outpatient treatment with topical AD medication(s). As used herein, "inadequate response" refers to a failure to achieve and maintain remission or a low disease activity state (comparable to Investigator's Global Assessment [IGA] 0=clear to 2=mild) despite treatment for at least 28 days with a topical therapy (e.g., a regimen of TCS of medium to high potency, ±TCI as appropriate). In some embodiments, a subject has an "inadequate response" if the patient has received documented systemic treatment for AD.

In some embodiments, treatment with an IL-4R antagonist improves, alleviates, or reduces one or more symptoms of AD in a subject, including but not limited to pruritus (i.e., itchiness), xerosis (skin dryness), eczematous lesions, erythema, papulation, edema, oozing/crusting, excoriation, lichenification, sleep disturbance, anxiety, and depression.

In some embodiments, treatment with an IL-4R antagonist improves one or more AD-associated parameters in a subject. Examples of "AD-associated parameters" include, but are not limited to: (a) Investigators Global Assessment (IGA); (b) Body Surface Area Involvement of Atopic Dermatitis (BSA); (c) Eczema Area and Severity Index (EASI); (d) SCORAD; (e) 5-D Pruritus Scale; and (f) Pruritus Numeric Rating Scale (NRS). An "improvement in an AD-associated parameter" means a decrease from baseline of one or more of IGA, BSA, EASI, SCORAD, 5-D Pruritus Scale, NRS/worst itch score, patient global impression of disease, patient global impression of change, Children's Dermatology Life Quality Index (CDLQI), Patient Oriented Eczema Measure (POEM), Dermatitis Family Index (DFI) score, or Patient-Reported Outcomes Measurement Information System (PROMIS) anxiety and/or depression score. The term "baseline," as used with respect to an AD-associated parameter, means the numerical value of the AD-associated parameter for a subject prior to or at the time of administration of a pharmaceutical composition as disclosed herein.

To determine whether an AD-associated parameter has "improved," the parameter is quantified at baseline and at one or more time points after administration of the pharmaceutical composition of the present disclosure. For example, an AD-associated parameter may be measured at day 1, day 2, day 3, day 4, day 5, day 6, day 7, day 8, day 9, day 10, day 11, day 12, day 14, day 15, day 22, day 25, day 29, day 36, day 43, day 50, day 57, day 64, day 71, day 85; or at the end of week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with a pharmaceutical composition of the present disclosure. The difference between the value of the parameter at a particular time point following initiation of treatment and the value of the parameter at baseline is used to establish whether there has been an "improvement" (e.g., a decrease) in the AD associated parameter.

AD-associated parameters are described in US Patent Publication No. US 2014/0072583, incorporated herein in its entirety.

In some embodiments, treatment with an IL-4R antagonist according to the methods of the present disclosure results in an improvement in IGA score for the subject relative to baseline. Methods for determining an IGA score for a subject are described in the Examples section below. In some embodiments, a subject to be treated has a baseline IGA score ≥3 (e.g., an IGA score of 3 or an IGA score of 4). In some embodiments, treatment with an IL-4R antagonist results in a reduction from baseline in IGA score (e.g., from a baseline IGA score 24) of at least 1 point by week 16 after administration of the first dose of the IL-4R antagonist. In some embodiments, treatment with an IL-4R antagonist results in a reduction from baseline (e.g., from an IGA score 24) to an IGA score of 0 or 1 by week 16 after administration of the first dose of the IL-4R antagonist.

In some embodiments, treatment with an IL-4R antagonist results in a reduction from baseline in IGA score (e.g., from a baseline IGA score ≥3) of at least 1 point by week 16 after administration of the first dose of the IL-4R antagonist. In some embodiments, treatment with an IL-4R antagonist results in a reduction from baseline (e.g., from an IGA score ≥3) to an IGA score of 0 or 1 by week 16 after administration of the first dose of the IL-4R antagonist.

In some embodiments, treatment with an IL-4R antagonist according to the methods of the present disclosure results in an improvement in an EASI score for a subject relative to baseline. Methods for determining an EASI score for a subject are described in the Examples section below. In some embodiments, a subject to be treated has a baseline EASI score of ≥21 (e.g., an EASI score ≥30). In some embodiments, treatment with an IL-4R antagonist results in a reduction of at least 30%, at least 40%, at least 50%, at least 60%, at least 70%, at least 75%, at least 80%, or at least 90% from baseline in an EASI score by week 16 after administration of the first dose of the IL-4R antagonist. In some embodiments, treatment with an IL-4R antagonist results in the subject achieving an EASI-75 response (i.e., a ≥75% improvement from baseline) by week 16 after administration of the first dose of the IL-4R antagonist. In some embodiments, treatment with an IL-4R antagonist results in the subject achieving an EASI-50 response (i.e., a ≥50% improvement from baseline) by week 16 after administration of the first dose of the IL-4R antagonist.

In some embodiments, treatment with an IL-4R antagonist according to the methods of the present disclosure results in an improvement in a BSA score for a subject relative to baseline. Methods for determining a BSA score for a subject are described in the Examples section below. In some embodiments, a subject to be treated has a baseline BSA score of a 15% (e.g., ≥20%, ≥30%, ≥40%, ≥50%, ≥75%, or ≥90%). In some embodiments, a subject to be treated has a baseline BSA score of ≥50%. In some embodiments, treatment with an IL-4R antagonist results in a reduction of at least 10%, at least 20%, at least 30%, at least 40%, at least 50% or more from baseline in percent BSA that is affected by AD by week 16 after administration of the first dose of the IL-4R antagonist.

In some embodiments, treatment with an IL-4R antagonist according to the methods of the present disclosure results in an improvement in a pruritus score, such as a "worst itch scale" score, also referred to herein as a Pruritus Numeric Rating Scale (NRS) score, for a subject relative to baseline. Methods for determining a pruritus score are described in the Examples section below. In some embodiments, a subject to be treated has a baseline worst itch score weekly average score for maximum itch intensity that is ≥4 (e.g., ≥7). In some embodiments, treatment with an IL-4R antagonist results in a reduction of ≥3 points (e.g., ≥4 points) of a weekly average of a daily pruritus score (e.g., worst itch score) from baseline by week 16 after administration of the first dose of the IL-4R antagonist.

In some embodiments, treatment with an IL-4R antagonist according to the methods of the present disclosure results in an improvement in a SCORAD score for the subject relative to baseline. Methods for determining a SCORAD score for a subject are described in the Examples section below. In some embodiments, a subject to be treated has a baseline SCORAD score ≥40 (e.g., a SCORAD score ≥50, ≥60, or ≥70). In some embodiments, treatment with an IL-4R antagonist results in a reduction in SCORAD score of at least 20%, at least 30%, at least 40%, at least 50%, at least 60%, at least 70%, at least 75%, at least 80%, or at least 90% from baseline by week 16 after administration of the first dose of the IL-4R antagonist.

In some embodiments, treatment with an IL-4R antagonist enhances the efficacy and/or safety of a topical therapy for AD. As used herein, a topical therapy (e.g., TCS) regimen is "enhanced" if one or more of the following outcomes or phenomena are observed or achieved in a subject: (1) the amount of the topical agent (e.g., TCS) that is concomitantly administered is reduced; (2) the number of days in which the topical agent (e.g., TCS) is concomitantly administered is reduced; (3) the patient is administered a lower potency of the topical agent (e.g., the patient is switched from a medium-potency TCS to a low-potency TCS); (4) there is a reduction in or elimination of one or side effects due to the topical agent (e.g., TCS); or (5) there is a reduction in toxicity due to the topical agent (e.g., TCS). In some embodiments, the amount of the topical agent (e.g., TCS) that is concomitantly administered to the subject is decreased by at least 20%, 30%, 40%, 50%, 60%, 70%, 80% or more as compared to a baseline value for the subject or as compared to a subject that is not administered an IL-4R inhibitor. In some embodiments, treatment with an IL-4R antagonist allows for concomitant treatment with the topical agent (e.g., TCS) to be tapered off or discontinued.

Interleukin-4 Receptor Antagonists

In some embodiments, the methods of the present disclosure comprise administering to a subject in need thereof (e.g., a pediatric subject having severe AD or moderate-to-severe AD) an interleukin-4 receptor (IL-4R) antagonist or a pharmaceutical composition comprising an IL-4R antagonist. As used herein, an "IL-4R antagonist" (also referred to herein as an "IL-4R inhibitor", an "IL-4R blocker," or an "IL-4Rα antagonist") is any agent that binds to or interacts with IL-4Rα or an IL-4R ligand, and inhibits or attenuates the normal biological signaling function of a type 1 and/or a type 2 IL-4 receptor. Human IL-4Rα has the amino acid sequence of SEQ ID NO:11. A type 1 IL-4 receptor is a dimeric receptor comprising an IL-4Rα chain and a γc chain. A type 2 IL-4 receptor is a dimeric receptor comprising an IL-4Rα chain and an IL-13Rα1 chain. Type 1 IL-4 receptors interact with and are stimulated by IL-4, while type 2 IL-4 receptors interact with and are stimulated by both IL-4 and IL-13. Thus, the IL-4R antagonists that can be used in the methods of the present disclosure may function by blocking IL-4-mediated signaling, IL-13-mediated signaling, or both IL-4- and IL-13-mediated signaling. The IL-4R antagonists of the present disclosure may thus prevent the interaction of IL-4 and/or IL-13 with a type 1 or type 2 receptor.

Non-limiting examples of categories of IL-4R antagonists include small molecule IL-4R inhibitors, anti-IL-4R aptamers, peptide-based IL-4R inhibitors (e.g., "peptibody" molecules), "receptor-bodies" (e.g., engineered molecules comprising the ligand-binding domain of an IL-4R component), and antibodies or antigen-binding fragments of antibodies that specifically bind human IL-4Rα. As used herein, IL-4R antagonists also include antigen-binding proteins that specifically bind IL-4 and/or IL-13.

Anti-IL-4Rα Antibodies and Antigen-Binding Fragments Thereof

In certain exemplary embodiments of the present disclosure, the IL-4R antagonist is an anti-IL-4Rα antibody or antigen-binding fragment thereof. The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order FR1, CDR1, FR2, CDR2, FR3, CDR3, FR4. In some embodiments, the FRs of the anti-IL-4R antibody (or antigen-binding portion thereof) are identical to the human germline sequences. In some embodiments, one or more FRs of the anti-IL-4R antibody (or antigen-binding portion thereof) are naturally or artificially modified.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed by the term "antigen-binding fragment," as used herein.

An antigen-binding fragment of an antibody will typically comprise at least one variable domain. The variable domain may be of any size or amino acid composition and will generally comprise at least one CDR that is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$—$V_L$ or $V_L$—$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (Xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The constant region of an antibody is important in the ability of an antibody to fix complement and mediate cell-dependent cytotoxicity. Thus, in some embodiments the isotype of an antibody may be selected on the basis of whether it is desirable for the antibody to mediate cytotoxicity.

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present disclosure using routine techniques available in the art. For example, in some embodiments, the methods of the present disclosure comprise the use of bispecific antibodies wherein one arm of an immunoglobulin is specific for IL-4Rα or a fragment thereof, and the other arm of the immunoglobulin is specific for a second therapeutic target or is conjugated to a therapeutic moiety. Exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, Cross-Fab, (SEED) body, leucine zipper, Duobody, IgG1/IgG2, dual acting Fab (DAF)-IgG, and Mab² bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., J. Am. Chem. Soc. [Epub: Dec. 4, 2012]).

In some embodiments, the antibodies used in the methods of the present disclosure are human antibodies. The term "human antibody," as used herein, is intended to include antibodies having variable and constant regions derived from human germline immunoglobulin sequences. The human antibodies of the disclosure may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present disclosure may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see, e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

An "isolated antibody" refers to an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody." An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

According to certain embodiments, the antibodies used in the methods of the present disclosure specifically bind IL-4Rα. The term "specifically binds," as used herein, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. In some embodiments, an antibody that "specifically binds" IL-4Rα binds to IL-4Rα or a portion thereof with an equilibrium dissociation constant ($K_D$) of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 1 nM, less than about 0.5 nM, less than about 0.25 nM, less than about 0.1 nM or less than about 0.05 nM, as measured in a surface plasmon resonance assay (e.g., BIAcore™, Biacore Life Sciences division of GE Healthcare, Piscataway, NJ). In some embodiments, an antibody that specifically binds to a target antigen (e.g., IL-4Rα) can also specifically bind to another antigen, e.g., an ortholog of the target antigen. For example, in some embodiments, an isolated antibody that specifically binds human IL-4Rα exhibits cross-reactivity to other antigens, such as IL-4Rα molecules from other (non-human) species.

In some embodiments, the IL-4R antagonist is an anti-IL-4Rα antibody, or antigen-binding fragment thereof, comprising a heavy chain variable region (HCVR), light chain variable region (LCVR), and/or complementarity determining regions (CDRs) comprising any of the amino acid sequences of the anti-IL-4R antibodies as set forth in U.S. Pat. No. 7,608,693. In some embodiments, the IL-4R antagonist is an anti-IL-4Rα antibody or antigen-binding fragment thereof that comprises the heavy chain complementarity determining regions (HCDRs) of a heavy chain variable region (HCVR) comprising the amino acid sequence of SEQ ID NO:1 and the light chain complementarity determining regions (LCDRs) of a light chain variable region (LCVR) comprising the amino acid sequence of SEQ ID NO:2. In some embodiments, the IL-4R antagonist is an anti-IL-4Rα antibody or antigen-binding fragment thereof that comprises three HCDRs (HCDR1, HCDR2 and HCDR3) and three LCDRs (LCDR1, LCDR2 and LCDR3), wherein the HCDR1 comprises the amino acid sequence of SEQ ID NO:3; the HCDR2 comprises the amino acid sequence of SEQ ID NO:4; the HCDR3 comprises the amino acid sequence of SEQ ID NO:5; the LCDR1 comprises the amino acid sequence of SEQ ID NO:6; the LCDR2 comprises the amino acid sequence of SEQ ID NO:7; and the LCDR3 comprises the amino acid sequence of SEQ ID NO:8.

In some embodiments, the anti-IL-4R antibody or antigen-binding fragment thereof comprises the HCDR1, HCDR2, HCDR3, LCDR1, LCDR2, and LCDR3 of SEQ ID NOs: 3, 4, 5, 6, 7, and 8, respectively, and further comprises an HCVR having at least 85% sequence identity (e.g., at least 90%, 91%, 92%, 93%, 94%, 95%, 96%, 97%, 98%, or 99% sequence identity) to the amino acid sequence of SEQ ID NO:1 and an LCVR having at least 85% sequence identity (e.g., at least 90%, 91%, 92%, 93%, 94%, 95%, 96%, 97%, 98%, or 99% sequence identity) to the amino acid sequence of SEQ ID NO:2. In some embodiments, the anti-IL-4R antibody or antigen-binding fragment thereof comprises an HCVR comprising SEQ ID NO:1 and an LCVR comprising SEQ ID NO:2.

In some embodiments, the anti-IL-4R antibody comprises a heavy chain comprising the amino acid sequence of SEQ ID NO:9. In some embodiments, the anti-IL-4R antibody comprises a light chain comprising the amino acid sequence of SEQ ID NO:10.

An exemplary antibody comprising a heavy chain comprising the amino acid sequence of SEQ ID NO:9 and a light chain comprising the amino acid sequence of SEQ ID NO:10 is the fully human anti-IL-4R antibody known as dupilumab. According to certain exemplary embodiments, the methods of the present disclosure comprise the use of dupilumab, or a bioequivalent thereof. The term "bioequivalent," as used herein with reference to dupilumab, refers to anti-IL-4R antibodies or IL-4R-binding proteins or fragments thereof that are pharmaceutical equivalents or pharmaceutical alternatives whose rate and/or extent of absorption do not show a significant difference with that of dupilumab when administered at the same molar dose under similar experimental conditions, either single dose or multiple dose. In some embodiments, the term refers to antigen-binding proteins that bind to IL-4R which do not have clinically meaningful differences with dupilumab in their safety, purity and/or potency.

Other anti-IL-4Rα antibodies that can be used in the context of the methods of the present disclosure include, e.g., the antibody referred to and known in the art as AMG317 (Corren et al., 2010, *Am J Respir Crit Care Med.*, 181(8):788-796), or MEDI 9314, or any of the anti-IL-4Rα antibodies as set forth in U.S. Pat. Nos. 7,186,809, 7,605, 237, 7,638,606, 8,092,804, 8,679,487, or U.S. Pat. No. 8,877,189.

In some embodiments, an anti-IL-4Rα antibody used in the methods of the present disclosure can have pH-dependent binding characteristics. For example, an anti-IL-4Rα antibody for use as disclosed herein may exhibit reduced binding to IL-4Rα at acidic pH as compared to neutral pH. Alternatively, an anti-IL-4Rα antibody for use as disclosed herein may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-4Rα at acidic pH as compared to neutral pH" is expressed in terms of a ratio of the $K_D$ value of the antibody binding to IL-4Rα at acidic pH to the $K_D$ value of the antibody binding to IL-4Rα at neutral pH (or vice versa). For example, an antibody or antigen-binding fragment thereof may be regarded as exhibiting "reduced binding to IL-4Rα at acidic pH as compared to neutral pH" for purposes of the present disclosure if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present disclosure can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen binding at acidic pH relative to neutral pH may be obtained.

Preparation of Human Antibodies

Methods for generating human antibodies in transgenic mice are known in the art. Any such known methods can be used in the context of the present disclosure to make human antibodies that specifically bind to human IL-4R.

Using VELOCIMMUNE™ technology (see, for example, U.S. Pat. No. 6,596,541, Regeneron Pharmaceuticals) or any other known method for generating monoclonal antibodies, high affinity chimeric antibodies to IL-4R are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc., using standard procedures known to those skilled in the art. The mouse constant regions are replaced with a desired human constant region to generate the fully human antibody of the disclosure, for example wild-type or modified IgG1 or IgG4. While the constant region selected may vary according to specific use, high affinity antigen-binding and target specificity characteristics reside in the variable region.

In general, the antibodies that can be used in the methods of the present disclosure possess high affinities, as described above, when measured by binding to antigen either immobilized on solid phase or in solution phase. The mouse constant regions are replaced with desired human constant regions to generate the fully human antibodies of the disclosure. While the constant region selected may vary according to specific use, high affinity antigen-binding and target specificity characteristics reside in the variable region.

In one embodiment, a human antibody or antigen-binding fragment thereof that specifically binds IL-4R and that can be used in the methods disclosed herein comprises the three heavy chain CDRs (HCDR1, HCDR2 and HCDR3) contained within a heavy chain variable region (HCVR) having an amino acid sequence of SEQ ID NO: 1, and the three light chain CDRs (LCVR1, LCVR2, LCVR3) contained within a light chain variable region (LCVR) having an amino acid sequence of SEQ ID NO: 2. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); A-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

Pharmaceutical Compositions

In one aspect, the present disclosure provides methods that comprise administering an IL-4R antagonist to a subject, wherein the IL-4R antagonist (e.g., an anti-IL-4R antibody) is contained within a pharmaceutical composition that comprises one or more pharmaceutically acceptable vehicle, carriers, and/or excipients. Various pharmaceutically acceptable carriers and excipients are well-known in the art. See, e.g., Remington's Pharmaceutical Sciences, Mack Publishing Company, Easton, PA In some embodiments, the carrier is suitable for intravenous, intramuscular, oral, intraperitoneal, intrathecal, transdermal, topical, or subcutaneous administration.

Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. In some embodiments, a pharmaceutical composition as disclosed herein is administered intravenously. In some embodiments, a pharmaceutical composition as disclosed herein is administered subcutaneously.

In some embodiments, the pharmaceutical composition comprises an injectable preparation, such as a dosage form for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

The dose of antibody administered to a subject according to the methods of the present disclosure may vary depending upon the age and the size of the subject, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions comprising anti-IL-4R antibodies may be determined empirically; for example, subject progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351). Specific exemplary doses of anti-IL4R antibodies, and administration regimens involving the same, that can be used in the context of the present disclosure are disclosed elsewhere herein.

In some embodiments, a pharmaceutical composition of the present disclosure is contained within a container. Thus, in another aspect, containers comprising a pharmaceutical composition as disclosed herein (e.g., a pharmaceutical composition comprising an IL-4R antagonist such as an anti-IL-4R antibody as disclosed herein) are provided. For example, in some embodiments, a pharmaceutical composition is contained within a container selected from the group consisting of a glass vial, a syringe, a pen delivery device, and an autoinjector.

In some embodiments, a pharmaceutical composition of the present disclosure is delivered, e.g., subcutaneously or intravenously, with a standard needle and syringe. In some embodiments, the syringe is a pre-filled syringe. In some embodiments, a pen delivery device or autoinjector is used to deliver a pharmaceutical composition of the present disclosure (e.g., for subcutaneous delivery). A pen delivery device can be reusable or disposable. Typically, a reusable pen delivery device utilizes a replaceable cartridge that contains a pharmaceutical composition. Once the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Examples of suitable pen and autoinjector delivery devices include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BDM pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany). Examples of disposable pen delivery devices having applications in subcutaneous delivery of a pharmaceutical composition of the present disclosure include, but are not limited to the SOLOSTAR™ pen (Sanofi-Aventis), the FLEXPEN™ (Novo Nordisk), and the KWiKPEN™

(Eli Lilly), the SURECLICK™ Autoinjector (Amgen, Thousand Oaks, CA), the PENLET™ (Haselmeier, Stuttgart, Germany), the EPIPEN (Dey, L.P.), and the HUMIRA™ Pen (Abbott Labs, Abbott Park IL).

In some embodiments, the pharmaceutical composition is delivered using a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533. Other delivery systems are known and can be used to administer the pharmaceutical composition, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432).

In some embodiments, pharmaceutical compositions for use as described herein are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-4R antibody that can be used in the context of the present disclosure are disclosed, e.g., in U.S. Pat. No. 8,945,559.

Dosage and Administration

In some embodiments, an IL-4R antagonist (e.g., anti-IL-4R antibody) is administered to a subject according to the methods of the present disclosure in a therapeutically effective amount. As used herein with reference to an IL-4R antagonist, the phrase "therapeutically effective amount" means an amount of IL-4R antagonist that results in one or more of (a) an improvement in one or more AD-associated parameters (as mentioned elsewhere herein); and/or (b) a detectable improvement in one or more symptoms or indicia of atopic dermatitis.

In the case of an anti-IL-4R antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-4R antibody. In some embodiments, a therapeutically effective amount is from about 75 mg to about 600 mg, or from about 100 mg to about 600 mg, or from about 200 mg to about 600 mg. In certain embodiments, 75 mg, 100 mg, 150 mg, 200 mg, or 300 mg of an anti-IL-4R antibody is administered to a subject.

The amount of IL-4R antagonist (e.g., anti-IL-4R antibody) contained within the individual doses may be expressed in terms of milligrams of antibody per kilogram of subject body weight (i.e., mg/kg). For example, the IL-4R antagonist may be administered to a subject at a dose of about 0.0001 to about 10 mg/kg of subject body weight, e.g., at a dose of about 1 mg/kg to about 10 mg/kg, at a dose of about 2 mg/kg to about 9 mg/kg, or at a dose of about 3 mg/kg to about 8 mg/kg. In some embodiments, the IL-4R antagonist may be administered to a subject at a dose of about 1 mg/kg, 2 mg/kg, 3 mg/kg, 4 mg/kg, 5 mg/kg, 6 mg/kg, 7 mg/kg, 8 mg/kg, 9 mg/kg, or 10 mg/kg.

In some embodiments, the methods disclosed herein comprise administering an IL-4R antagonist to a subject at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved.

In some embodiments, multiple doses of an IL-4R antagonist are administered to a subject over a defined time course. In some embodiments, the methods of the present disclosure comprise sequentially administering to a subject multiple doses of an IL-4R antagonist. As used herein, "sequentially administering" means that each dose of IL-4R antagonist is administered to the subject at a different point in time, e.g., on different days separated by a predetermined interval (e.g., hours, days, weeks or months). In some embodiments, the methods of the disclosure comprise sequentially administering to the patient a single initial dose of an IL-4R antagonist, followed by one or more secondary doses of the IL-4R antagonist, and optionally followed by one or more tertiary doses of the IL-4R antagonist.

The terms "initial dose," "secondary doses," and "tertiary doses," refer to the temporal sequence of administration of the IL-4R antagonist. Thus, the "initial dose" is the dose that is administered at the beginning of the treatment regimen (also referred to as the "loading dose"); the "secondary doses" are the doses that are administered after the initial dose; and the "tertiary doses" are the doses that are administered after the secondary doses. The initial, secondary, and tertiary doses may all contain the same amount of IL-4R antagonist, but generally may differ from one another in terms of frequency of administration. In certain embodiments, however, the amount of IL-4R antagonist contained in the initial, secondary and/or tertiary doses varies from one another (e.g., adjusted up or down as appropriate) during the course of treatment. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses").

In some embodiments, a loading dose is a "split dose" that is administered as two or more doses (e.g., 2, 3, 4, or 5 doses) that are administered on separate days. In some embodiments, a loading dose is administered as a split dose wherein the two or more doses are administered at least about one week apart. In some embodiments, a loading dose is administered as a split dose wherein the two or more doses are administered about 1 week, 2 weeks, 3 weeks, or 4 weeks apart. In some embodiments, the loading dose is split evenly over the two or more doses (e.g., half of the loading dose is administered as the first portion and half of the loading dose is administered as the second portion). In some embodiments, the loading dose is split unevenly over the two or more doses (e.g., more than half of the loading dose is administered as the first portion and less than half of the loading dose is administered as the second portion). In some embodiments, a loading dose is administered as a split dose wherein the first portion of the loading dose (e.g., the first half) is administered at Day 1 and the second portion of the same loading dose (e.g., the second half) is administered after 1 week (e.g., on Day 8), after 2 weeks (e.g., on Day 15), after 3 weeks (e.g., on Day 22), or after 4 weeks (e.g., on Day 29), followed by one or more secondary or maintenance doses.

For example, an IL-4R antagonist may be administered to a subject at a loading dose of about 200 mg, 400 mg, or about 600 mg followed by one or more maintenance doses of about 75 mg to about 300 mg. In one embodiment, the initial dose and the one or more secondary doses each include 50 mg to 600 mg of the IL-4R antagonist, e.g., 100 mg, 150 mg, 200 mg, 250 mg, 300 mg, 400 mg, 500 mg, or 600 mg of the IL-4R antagonist. In some embodiments, the initial dose and the one or more secondary doses each contain the same amount of the IL-4R antagonist. In other embodiments, the initial dose comprises a first amount of the IL-4R antagonist, and the one or more secondary doses each comprise a second amount of the IL-4R antagonist. For example, the first amount of the IL-4R antagonist can be 1.5×, 2×, 2.5×, 3×, 3.5×, 4× or 5× or more than the second amount of the IL-4R antagonist. In one exemplary embodiment, an IL-4R antagonist is administered to a subject at a loading dose of about 400 mg or about 600 mg followed by one or more maintenance doses of about 200 mg or 300 mg. In another exemplary embodiment, for a subject having a body weight that is <30 kg (e.g., ≥15 kg to <30 kg), an IL-4R antagonist is administered to a subject at a loading dose of about 200 mg followed by one or more maintenance doses of about 100 mg, or at a loading dose of about 600 mg followed by one or more maintenance doses of about 300 mg. In another exemplary embodiment, for a subject having a body weight that is ≥30 kg (e.g., ≥30 kg to <60 kg), an IL-4R antagonist may be administered to a subject at a loading dose of about 400 mg followed by one or more maintenance doses of about 200 mg, or at a loading dose of about 600 mg followed by one or more maintenance doses of about 300 mg. In yet another exemplary embodiment, for a subject having a body weight that is ≥60 kg, an IL-4R antagonist may be administered to a subject at a loading dose of about 600 mg followed by one or more maintenance doses of about 300 mg. In some embodiments, a subject is administered an IL-4R antagonist (e.g., one or more doses from about 50 mg to about 600 mg, e.g., about 50 mg, about 75 mg, about 100 mg, about 150 mg, about 200 mg, about 250 mg, about 300 mg, about 350 mg, about 400 mg, about 450 mg, about 500 mg, about 550 mg, or about mg) without a loading dose.

In some embodiments, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of IL-4R antagonist that is administered to a patent prior to the administration of the very next dose in the sequence with no intervening doses.

The methods of the disclosure may comprise administering to a patient any number of secondary and/or tertiary doses of an IL-4R antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In some embodiments involving multiple secondary doses, each secondary dose is administered at the same frequency as the other secondary doses. For example, each secondary dose may be administered to the patient 1 to 2 weeks after the immediately preceding dose. Similarly, in some embodiments involving multiple tertiary doses, each tertiary dose is administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

In some embodiments, for a subject having severe AD who is ≥6 years to <12 years of age, a therapeutically effective amount of an IL-4R antagonist (e.g., anti-IL-4R antibody) comprises an initial (loading) dose followed by one or more secondary (maintenance) doses, wherein the initial dose of the IL-4R antagonist (e.g., anti-IL-4R antibody) comprises 200 mg and each secondary dose of the IL-4R antagonist (e.g., anti-IL-4R antibody) comprises 100 mg, administered every two weeks (Q2W), if the subject is <30 kg in weight.

In some embodiments, for a subject having severe AD who is ≥6 years to <12 years of age, a therapeutically effective amount of an IL-4R antagonist (e.g., anti-IL-4R antibody) comprises an initial (loading) dose followed by one or more secondary (maintenance) doses, wherein the initial dose of the IL-4R antagonist (e.g., anti-IL-4R antibody) comprises 400 mg and each secondary dose of the IL-4R antagonist (e.g., anti-IL-4R antibody) comprises 200 mg, administered every two weeks (Q2W), if the subject is ≥30 kg in weight.

In some embodiments, for a subject having severe AD who is ≥6 years to <12 years of age, a therapeutically effective amount of an IL-4R antagonist (e.g., anti-IL-4R antibody) comprises an initial (loading) dose followed by one or more secondary (maintenance) doses, wherein the initial dose of the IL-4R antagonist (e.g., anti-IL-4R antibody) comprises 600 mg and each secondary dose of the IL-4R antagonist (e.g., anti-IL-4R antibody) comprises 300 mg, administered every four weeks (Q4W).

In some embodiments, for a subject having severe AD who is ≥6 years to <12 years of age, a therapeutically effective amount of an IL-4R antagonist (e.g., anti-IL-4R antibody) comprises an initial (loading) dose followed by one or more secondary (maintenance) doses, wherein the initial dose of the IL-4R antagonist (e.g., anti-IL-4R antibody) comprises 600 mg and each secondary dose of the IL-4R antagonist (e.g., anti-IL-4R antibody) comprises 300 mg, administered every four weeks (Q4W), if the subject is <30 kg in weight.

In some embodiments, for a subject having severe AD who is ≥6 years to <12 years of age, a therapeutically effective amount of an IL-4R antagonist (e.g., anti-IL-4R antibody) comprises an initial (loading) dose followed by one or more secondary (maintenance) doses, wherein the initial dose of the IL-4R antagonist (e.g., anti-IL-4R antibody) comprises 600 mg and each secondary dose of the IL-4R antagonist (e.g., anti-IL-4R antibody) comprises 300 mg, administered every four weeks (Q4W), if the subject is ≥15 kg to <30 kg in weight. In some embodiments, the initial dose is administered as a split dose in which 300 mg is administered on Day 1 and 300 mg is administered two weeks later.

In some embodiments, for a subject having severe AD who is ≥6 years to <12 years of age, a therapeutically effective amount of an IL-4R antagonist (e.g., anti-IL-4R antibody) comprises an initial (loading) dose followed by one or more secondary (maintenance) doses, wherein the initial dose of the IL-4R antagonist (e.g., anti-IL-4R antibody) comprises 400 mg and each secondary dose of the IL-4R antagonist (e.g., anti-IL-4R antibody) comprises 200 mg, administered every two weeks (Q2W), if the subject is ≥30 kg to <60 kg in weight.

In some embodiments, for a subject having severe AD who is ≥6 years to <12 years of age, a therapeutically effective amount of an IL-4R antagonist (e.g., anti-IL-4R antibody) comprises an initial (loading) dose followed by one or more secondary (maintenance) doses, wherein the initial dose of the IL-4R antagonist (e.g., anti-IL-4R antibody) comprises 600 mg and each secondary dose of the IL-4R antagonist (e.g., anti-IL-4R antibody) comprises 300 mg, administered every two weeks (Q2W), if the subject is ≥60 kg in weight.

In some embodiments, the IL-4R antagonist is administered without an initial or loading dose. For example, in some embodiments, for a subject having severe AD who is ≥6 years to <12 years of age, a therapeutically effective amount of an IL-4R antagonist (e.g., anti-IL-4R antibody) comprises a dose of the IL-4R antagonist (e.g., anti-IL-4R antibody) comprising 100 mg administered every two weeks (Q2W), if the subject is <30 kg in weight.

In some embodiments, for a subject having severe AD who is ≥6 years to <12 years of age, a therapeutically effective amount of an IL-4R antagonist (e.g., anti-IL-4R antibody) comprises a dose of the IL-4R antagonist (e.g., anti-IL-4R antibody) comprising 200 mg administered every two weeks (Q2W), if the subject is ≥30 kg in weight.

In some embodiments, for a subject having severe AD who is ≥6 years to <12 years of age, a therapeutically effective amount of an IL-4R antagonist (e.g., anti-IL-4R antibody) comprises a dose of the IL-4R antagonist (e.g., anti-IL-4R antibody) comprising 300 mg administered every four weeks (Q4W).

In some embodiments, for a subject having severe AD who is ≥6 years to <12 years of age, a therapeutically effective amount of an IL-4R antagonist (e.g., anti-IL-4R antibody) comprises a dose of the IL-4R antagonist (e.g., anti-IL-4R antibody) comprising 300 mg administered every four weeks (Q4W), if the subject is <30 kg in weight.

In some embodiments, for a subject having severe AD who is ≥6 years to <12 years of age, a therapeutically effective amount of an IL-4R antagonist (e.g., anti-IL-4R antibody) comprises a dose of the IL-4R antagonist (e.g., anti-IL-4R antibody) comprising 300 mg administered every four weeks (Q4W), if the subject is ≥15 kg to <30 kg in weight.

In some embodiments, for a subject having severe AD who is ≥6 years to <12 years of age, a therapeutically effective amount of an IL-4R antagonist (e.g., anti-IL-4R antibody) comprises a dose of the IL-4R antagonist (e.g., anti-IL-4R antibody) comprising 200 mg administered every two weeks (Q2W), if the subject is ≥30 kg to <60 kg in weight.

In some embodiments, for a subject having severe AD who is ≥6 years to <12 years of age, a therapeutically effective amount of an IL-4R antagonist (e.g., anti-IL-4R antibody) comprises a dose of the IL-4R antagonist (e.g., anti-IL-4R antibody) comprising 300 mg administered every two weeks (Q2W), if the subject is ≥60 kg in weight.

In some embodiments, for a subject having severe AD who is ≥6 years to <12 years of age, a therapeutically effective amount of an IL-4R antagonist (e.g., anti-IL-4R antibody) comprises a dose of the IL-4R antagonist (e.g., anti-IL-4R antibody) comprising 200 mg administered every week (QW), if the subject is ≥60 kg in weight.

In some embodiments, for a subject having severe AD who is ≥6 years to <12 years of age, a therapeutically effective amount of an IL-4R antagonist (e.g., anti-IL-4R antibody) comprises a dose of the IL-4R antagonist (e.g., anti-IL-4R antibody) comprising 300 mg administered every week (QW), if the subject is ≥60 kg in weight.

Therapeutic Dosage Forms

In another aspect, the present disclosure provides therapeutic dosage forms of an IL-4R antagonist (e.g., an anti-IL-4R antibody or antigen-binding fragment thereof), wherein administration of the dosage form to a subject over a period of time (e.g., over 4 weeks, 8 weeks, 12 weeks, 16 weeks, or longer) results in sustained serum concentrations of the IL-4R antagonist.

In yet another aspect, the present disclosure provides a therapeutic dosage form of a pharmaceutical composition comprising an IL-4R antagonist, wherein the therapeutic dose is 2 mg/kg, wherein weekly administration of the dosage form for four weeks to a subject provides a mean serum concentration of 74 (±20) mg/L. In one embodiment of a therapeutic dosage form according to the disclosure, the mean serum concentration of the IL-4R antagonist is maintained for at least 48 weeks, when the therapeutic dosage form is administered weekly.

In still another aspect, the present disclosure provides a therapeutic dosage form of a pharmaceutical composition comprising an IL-4R antagonist, wherein the therapeutic dose is 4 mg/kg, wherein weekly administration of the dosage form for four weeks to a subject provides a mean serum concentration of 161 (±60) mg/L. In one embodiment of a therapeutic dosage form according to the disclosure, the mean serum concentration of the IL-4R antagonist is maintained for at least 48 weeks, when the therapeutic dosage form is administered weekly.

In still another aspect, the present disclosure provides a therapeutic dosage form of a pharmaceutical composition comprising an IL-4R antagonist, wherein administration of the dosage form for 16 weeks to a subject provides a mean serum concentration of 80-100 mg/L. In one embodiment of a therapeutic dosage form according to the disclosure, the therapeutic dose is 200 mg administered every two weeks. In another embodiment of a therapeutic dosage form according to the disclosure, the therapeutic dose is 300 mg administered every four weeks.

In specific embodiments of a therapeutic dosage form according to the disclosure, the subject is ≥6 years to <18 years of age. In additional embodiments of a therapeutic dosage form according to the disclosure, the IL-4R antagonist is an anti-IL-4R antibody or antigen-binding fragment thereof that comprises an HCDR1 comprising the amino acid sequence of SEQ ID NO:3, an HCDR2 comprising the amino acid sequence of SEQ ID NO:4, an HCDR3 comprising the amino acid sequence of SEQ ID NO:5, an LCDR1 comprising the amino acid sequence of SEQ ID NO:6, an LCDR2 comprising the amino acid sequence of SEQ ID NO:7, and an LCDR3 comprising the amino acid sequence of SEQ ID NO:8.

Dose Up-Titration

In another aspect, the present disclosure provides methods of treating AD (e.g., moderate-to-severe AD or severe AD) in a subject that is ≥6 to <18 years of age, wherein the dose of the IL-4R antagonist is up-titrated if the subject does not adequately respond to an initial dosing regimen. In some embodiments, the method comprises:

(a) administering a first dosing regimen of an IL-4R antagonist as disclosed herein (e.g., an IL-4R antibody) to a subject having moderate-to-severe AD or severe AD, wherein the subject is ≥6 years to <18 years of age;

(b) determining whether the subject has an inadequate clinical response to the first dosing regimen; and (c) for a subject having an inadequate clinical response, administering a second dosing regimen of the IL-4R antagonist to the subject, wherein the second dosing regimen comprises administering the IL-4R antagonist at (i) a dose of 200 mg Q2W if the subject has a body weight <60 kg; or (ii) a dose of 300 mg Q2W if the subject has a body weight ≥60 kg.

In some embodiments, the subject is a pediatric subject (≥6 to <12 years of age) having severe AD. In some embodiments, the initial dosing regimen for the pediatric subject comprises administering the IL-4R antagonist at an initial dose of 600 mg followed by one or more secondary doses of 300 mg every four weeks (Q4W). In some embodiments, the initial dosing regimen has a duration of at least 16 weeks.

In some embodiments, the subject is an adolescent subject (≥12 to <18 years of age) having moderate-to-severe AD. In some embodiments, the initial dosing regimen for the adolescent subject comprises administering the IL-4R antagonist at an initial dose of 600 mg followed by one or more secondary doses of 300 mg every four weeks (Q4W). In some embodiments, the initial dosing regimen has a duration of at least 16 weeks.

In some embodiments, an "inadequate clinical response" is determined by assessing one or more AD-associated parameters as disclosed herein (e.g., IGA or EASI scores). In some embodiments, a subject has an "inadequate clinical response" when the subject has an IGA score ≥2 after at least 16 weeks of treatment with the first dosing regimen. In some embodiments, a subject has an "inadequate clinical response" when the subject has an EASI score that is not reduced by at least 50% (e.g., by at least 75%) from baseline after at least 16 weeks of treatment with the first dosing regimen. For a subject that is identified as having an inadequate clinical response to the first dosing regimen, the method comprises up-titrating the dose of the IL-4R antagonist to one of the following regimens, based on body weight: for patients weighing <60 kg, the dose of the IL-4R antagonist is up-titrated to a dosage of 200 mg Q2W; for patients weighing ≥60 kg, the dose of the IL-4R antagonist is up-titrated to a dosage of 300 mg Q2W.

Combination Therapies

In some embodiments, the methods of the present disclosure comprise administering to the subject the IL-4R antagonist in combination with one or more additional therapeutic agents. In some embodiments, the additional therapeutic agent is a topical therapeutic agent, e.g., a TCS or a topical nonsteroidal medication such as a TC or crisaborole. As used herein, the expression "in combination with" means that the topical therapy (e.g., TCS) is administered before, after, or concurrent with the IL-4R inhibitor. The term "in combination with" also includes sequential or concomitant administration of IL-4R inhibitor and the topical therapy (e.g., TCS).

For example, when administered "before" the pharmaceutical composition comprising the IL-4R antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the IL-4R antagonist. When administered "after" the pharmaceutical composition comprising the IL-4R antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the IL-4R antagonist. Administration "concurrent" or with the pharmaceutical composition comprising the IL-4R antagonist means that the additional therapeutic agent is administered to the subject in a separate dosage form within less than 5 minutes (before, after, or at the same time) of administration of the pharmaceutical composition comprising the IL-4R antagonist, or administered to the subject as a single combined dosage formulation comprising both the additional therapeutic agent and the IL-4R antagonist.

In some embodiments, the additional therapeutic agent is a TCS. In some embodiments, the TCS is a medium-potency TCS. In some embodiments, the TCS is a low-potency TCS. In some embodiments, the additional therapeutic agent is a TCI. In some embodiments, the additional therapeutic agent is crisaborole.

EXAMPLES

The following examples are put forth so as to provide those of ordinary skill in the art with a complete disclosure and description of how to make and use the methods and compositions of the disclosure, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Clinical Trial Investigating the Efficacy of Dupilumab in Pediatric Patients with Severe Atopic Dermatitis Study Design and Objectives This was a Phase 3, multicenter, randomized, double-blind, parallel group study to investigate the efficacy and safety of dupilumab administered concomitantly with topical corticosteroids (TCS) in pediatric patients with severe AD. The study population included patients ≥6 years to <12 years of age with severe AD whose disease cannot be adequately controlled with topical medications. Dupilumab is a fully human anti-IL-4R antibody comprising a heavy chain comprising the amino acid sequence of SEQ ID NO:9 and a light chain comprising the amino acid sequence of SEQ ID NO:10; an HCVR/LCVR amino acid sequence pair comprising SEQ ID NOs:1/2; and heavy and light chain CDR sequences comprising SEQ ID NOs:3-8.

Eligible patients who successfully complete screening procedures were randomized to one of the following treatment groups:
(1) dupilumab every 2 weeks (Q2W) treatment group: 100 mg for patients <30 kg or 200 mg for patients ≥30 kg
(2) dupilumab every 4 weeks (Q4W) treatment group: 300 mg
(3) placebo.

To account for body size difference in the pediatric population and taking into account the observed large therapeutic indices of dupilumab, a tiered fixed dosing regimen was chosen. This approach reduces the risk of dosing errors that can occur with weight-based dosing, as well as allowing for dosing convenience by simplifying administration using a prefilled syringe/device. Dupilumab was dosed as follows: For the dupilumab Q2W treatment group, patients with baseline weight <30 kg receive Q2W SC injections of 100 mg dupilumab (0.7 mL of a 150 mg/mL solution) from week 2 to week 14, following a loading dose of 200 mg on day 1. Patients with baseline weight 230 kg receive Q2W SC injections of 200 mg dupilumab (1.14 mL of a 175 mg/mL solution) from week 2 to week 14, following a loading dose of 400 mg on day 1. For the dupilumab Q4W treatment group, all patients regardless of weight receive Q4W SC injections of 300 mg dupilumab (2 mL of a 150 mg/mL solution) from week 4 to week 12, following a loading dose of 600 mg on day 1. For the placebo treatment group, patients receive matching placebo (including doubling the amount of placebo on day 1 to match the loading dose).

The study consisted of the following periods: (1) screening period of up to 9 weeks; (2) TCS standardization period of 2 weeks; (3) treatment period of 16 weeks; and (4) follow-up of 12 weeks (for patients who do not enter the OLE). During the screening period, systemic treatments for AD was washed out, as applicable. The use of TCS (±TCI) was permitted at the discretion of the investigator during the screening period until day −14. Starting on day −14, all patients initiated a standardized TCS treatment regimen.

During the treatment period, patients had weekly in-clinic visits through week 4, and then in-clinic visits Q4W through week 16 with weekly telephone visits in between the in-clinic visits. Parents/caregivers were trained on injecting study drug during in-clinic visit 3 (day 1), visit 5 (week 2), and visit 7 (week 4) (for patients who received Q2W treatment during the study). During weeks in which no in-clinic visit is scheduled, the parent/caregiver administered study drug to the patient. Parents/caregivers not wanting to administer study drug to patient were given the option to have the clinic staff administer all the study drug injections in the clinic. Safety, laboratory, and clinical assessments were performed at specified clinic visits. The end of treatment period visit occurred at week 16, two weeks after the last dose of study drug for patients randomized to the Q2W treatment group or placebo Q2W group, and 4 weeks after the last dose of study drug for patients randomized to the Q4W treatment or placebo Q4W group. The co primary endpoints were assessed at this visit.

Patients who participated in the study were offered the opportunity to screen for entry into the OLE study at the end of the treatment period (week 16). Patients declining to enroll in the OLE study or who failed eligibility criteria for the OLE study had a 12-week follow-up period. For these patients, after week 16, follow-up visits occurred every 4 weeks from week 20 to week 28. During the follow-up period, patients were monitored for safety and tolerability and have laboratory and clinical assessments.

Study Population

This study enrolled pediatric patients (aged ≥6 to <12 years at the time of screening) who have severe AD that cannot be adequately controlled with topical AD medications.

Inclusion Criteria: A patient had to meet the following criteria to be eligible for inclusion in the study: (1) male or female, 26 to <12 years of age at time of screening visit; (2) diagnosis of AD according to the American Academy of Dermatology consensus criteria (Eichenfield 2003) at screening visit; (3) chronic AD diagnosed at least 1 year prior to the screening visit; (4) IGA=4 at screening and baseline visits; (5) EASI ≥21 at the screening and baseline visits; (6) BSA ≥15% at screening and baseline visits; (7) baseline worst itch score weekly average score for maximum itch intensity 24 (Note: Baseline worst itch average score for maximum itch intensity is determined based on the average of daily worst itch scores for maximum itch intensity (the daily score ranges from 0 to 10) during the 7 days immediately preceding randomization. A minimum of 4 daily scores out of the 7 days is required to calculate the baseline average score. A complete daily score consists of answers to both questions: "What was the worst itch you had today?" and "What was the worst itch you had last night?" For patients who do not have at least 4 daily scores reported during the 7 days immediately preceding the planned randomization date, randomization should be postponed until this requirement is met, but without exceeding the 77-day maximum duration for screening plus TCS standardization) (8) documented recent history (within 6 months before the baseline visit) of inadequate response to topical AD medication(s). (Note: Inadequate response is defined as failure to achieve and maintain remission or a low disease activity state (comparable to IGA 0=clear to 2=mild) despite treatment with a daily regimen of TCS of medium to high potency (±TCI as appropriate), applied for at least 28 days. Patients with documented systemic treatment for AD in the past 6 months are also considered as inadequate responders to topical treatments and are potentially eligible for treatment with dupilumab after appropriate washout. (9) at least 11 (of a total of 14) applications of a stable dose of topical emollient (moisturizer) twice daily during the 7 consecutive days immediately before the baseline visit; (10) willing and able to comply with all clinic visits and study-related procedures; (11) patient, either alone or with help of parents/legal guardians, as appropriate, must be able to understand and complete study-related questionnaires; (12) parent or legal guardian must provide signed informed consent. Patients must also provide separate informed assent to enroll in the study, and sign and date either a separate informed assent form (IAF) or the informed consent form (ICF) signed by the parent/legal guardian (as appropriate based on local regulations and requirements).

Exclusion Criteria: The following were exclusion criteria for the study: (1) Participation in a prior dupilumab clinical study; (2) Treatment with a systemic investigational drug before the baseline visit; (Note: Treatment with a systemic investigational drug refers to treatment received in a clinical study with a drug that is not yet available on the market); (3) Treatment with a topical investigational drug within 2 weeks prior to the baseline visit; (4) Treatment with crisaborole within 2 weeks prior to the baseline visit; (5) History of important side effects of medium potency topical corticosteroids (e.g., intolerance to treatment, hypersensitivity reactions, significant skin atrophy, systemic effects), as assessed by the investigator or patient's treating physician; (6) Treatment with a TC within 2 weeks prior to the baseline visit; (7) Having used any of the following treatments within 4 weeks before the baseline visit, or any condition that, in the opinion of the investigator, is likely to require such treatment(s) during the first 4 weeks of study treatment: (a) immunosuppressive/immunomodulating drugs (e.g., systemic corticosteroids, cyclosporine, mycophenolate-mofetil, interferon gamma, Janus kinase inhibitors, azathioprine, methotrexate, etc.); (b) phototherapy for AD; (8) Treatment with biologics, as follows: (a) any cell-depleting agents including but not limited to rituximab: within 6 months before the baseline visit, or until lymphocyte and CD 19+ lymphocyte count returns to normal, whichever is longer; (b) other biologics: within 5 half-lives (if known) or 16 weeks before the baseline visit, whichever is longer; (9) Treatment with a live (attenuated) vaccine within 4 weeks before the baseline visit. (Note: For patents who have vaccination with live, attenuated vaccines planned during the course of the study (based on national vaccination schedule/local guidelines), it will be determined, after consultation with a pediatrician, whether the administration of vaccine can be postponed until after the end of study, or preponed to before the start of the study, without compromising the health of the patient. Patients for whom administration of live (attenuated) vaccine can be safely postponed would be eligible to enroll into the study. Patients who have their vaccination preponed can enroll in the study only after a gap of 4 weeks following administration of the vaccine.] (10) Planned or anticipated use of any prohibited medications and procedures during study treatment; (11) Body weight <15 kg at baseline; (12) Initiation of treatment of AD with prescription moisturizers or moisturizers containing additives such as ceramide, hyaluronic acid, urea, or filaggrin degradation products during the screening period (patients may continue using stable doses of such moisturizers if initiated before the screening visit); (13) Regular use (more than 2 visits per week) of a tanning booth/parlor within 8 weeks of the baseline visit; (14) Active chronic or acute infection requiring treatment with systemic antibiotics, antivirals, antiprotozoals, or antifungals within 2 weeks before the baseline visit. (Note: patients may be rescreened after infection resolves); (15) Established diagnosis of a primary immunodeficiency disorder (e.g., severe combined immunodeficiency, Wiskott Aldrich Syndrome, DiGeorge Syndrome, X-linked Agammaglobulinemia, common variable immunodeficiency), or secondary immunodeficiency (16) History of past or current tuberculosis or other mycobacterial infection; (17) Known history of human immunodeficiency virus (HIV) infection or HIV seropositivity at the screening visit; (18) Established diagnosis of hepatitis B viral infection at the time of screening or is positive for hepatitis B surface antigen (HBsAg) or hepatitis B core antibody (HBcAb) at the time of screening (Note: Patients who have gained immunity for hepatitis B virus infection after vaccination (patients who are HBsAg negative, hepatitis B surface antibody [HBsAb] positive, and HBcAb negative) are eligible for the study); (19) Established diagnosis of hepatitis C viral infection at the time of screening or is positive for hepatitis C antibody at the screening visit; (20) On current treatment for hepatic disease including but not limited to acute or chronic hepatitis, cirrhosis, or hepatic failure, or has evidence of liver disease as indicated by persistent (confirmed by repeated tests 22 weeks apart) elevated transaminases (alanine aminotransferase [ALT] and/or aspartate aminotransferase [AST]) more than 3 times the upper limit of normal (ULN) during the screening period; (21) Presence of any 1 or more of the following abnormalities in laboratory test results at screening: (i) Platelets ≥100×103/μL; (ii) Neutrophils <1.5×103/μL; (iii) Creatine phosphokinase (CPK) >5×ULN; (iv) Serum creatinine >1.5×ULN. (Note: If an abnormal value is detected at screening, a repeat test should be performed to confirm the abnormality); (22) Presence of skin comorbidities that may interfere with study assessments, including but not limited to conditions like scabies, seborrheic dermatitis, cutaneous T cell lymphoma, psoriasis, etc.; (23) History of malignancy before the baseline visit; (24) Diagnosed active endoparasitic infections; suspected or high risk of endoparasitic infection, unless clinical and (if necessary) laboratory assessment have ruled out active infection before randomization; (25) Severe concomitant illness(es) that, in the investigator's judgment, would adversely affect the patient's participation in the study. Examples include, but are not limited to patients with short life expectancy, patients with uncontrolled diabetes (hemoglobin A1c ≥29%), patients with cardiovascular conditions (e.g., Class III or IV cardiac failure according to the New York Heart Association classification), severe renal conditions (e.g., patients on dialysis), hepato-biliary conditions (e.g., Child-Pugh class B or C), neurological conditions (e.g., demyelinating diseases), active major autoimmune diseases (e.g., lupus, inflammatory bowel disease, rheumatoid arthritis, etc.), other severe endocrinological, gastrointestinal, metabolic, pulmonary, or lymphatic diseases. The specific justification for patients excluded under this criterion will be noted in study documents (chart notes, case report forms [CRF], etc.); (26) Any other medical or psychological condition including relevant laboratory abnormalities at screening that, in the opinion of the investigator, suggest a new and/or insufficiently understood disease, may present an unreasonable risk to the study patient as a result of his/her participation in this clinical trial, may make patient's participation unreliable, or may interfere with study assessments; (27) Planned major surgical procedure during the patient's participation in this study; (28) Patient or his/her immediate family is a member of the dupilumab investigational team; (29) Patient is female who is pregnant, breastfeeding, or planning to become pregnant or breastfeed during the study; (30) Patients who are committed to an institution by virtue of an order issued either by the judicial or the administrative authorities; (31) Patient is female of childbearing potential* and sexually active, who is unwilling to use highly effective methods of contraception prior to the initial dose, during the study and for at least 12 weeks after the last dose of study drug. Highly effective contraceptive measures include stable use of combined (estrogen and progestogen containing) hormonal contraception (oral, vaginal, transdermal) or progestogen-only hormonal contraception (oral, injectable, implantable) associated with inhibition of ovulation initiated 2 or more menstrual cycles prior to screening; intrauterine device (IUD); intrauterine hormone-releasing system (IUS); bilateral tubal ligation; vasectomized partner; and or sexual abstinence**. [*For the purpose of this study, any female who has had her first menstrual period (menarche) and is sexually active will be considered to be of childbearing potential. Female patients who are not of childbearing potential at the start of the study but have the onset of menarche during the course of the study and are sexually active will also have to follow adequate birth control methods to continue participation in the study. **Sexual abstinence is considered a highly effective method only if defined as refraining from heterosexual intercourse during the entire period of risk associated with the study treatments. The reliability of sexual abstinence needs to be evaluated in relation to the duration of the clinical trial and the preferred and usual lifestyle of the subject.]

Study Treatments

Investigational and Reference Treatments:

Dupilumab 175 mg/mL: Each 1.14 mL single-use, pre-filled glass syringe with snap-off cap delivers 200 mg of study drug (1.14 mL of a 175 mg/mL solution).

Dupilumab 150 mg/mL: Each 2.25 mL single-use, pre-filled glass syringe with snap-off cap delivers 300 mg of study drug (2.0 mL of a 150 mg/mL solution)

Dupilumab 150 mg/ml: Each 0.7 mL single-use, pre-filled glass syringe with snap-off cap delivers 100 mg study drug (0.7 mL of a 150 mg/mL solution).

Placebo matching dupilumab was prepared in the same formulation without the addition of protein (i.e., active substance, anti-IL-4Rα monoclonal antibody). Three matching placebo formulations were used (2 mL placebo matching 300 mg dupilumab formulation, 1.14 mL placebo matching 200 mg dupilumab formulation, and 0.7 mL placebo matching 100 mg dupilumab formulation).

Subcutaneous injection sites of the study drug was alternated among the different quadrants of the abdomen (avoiding navel and waist areas), upper thighs, and upper arms so that the same site is not injected for 2 consecutive administrations. To allow for adequate assessment of possible injection site reactions, study drug was administered only into areas of normal looking skin (for patients with 100% BSA involvement, patients were instructed to administer the injection into as near normal looking skin as possible).

Background treatment: Patients were instructed to apply moisturizers (emollients) at least twice daily for at least the 7 consecutive days immediately before randomization. After randomization, patients were required to continue to apply moisturizers throughout the study (all 28 weeks where applicable). However, to allow adequate assessment of skin dryness, moisturizers should not be applied for at least 8 hours before each clinic visit. All types of moisturizers were permitted, but patients were not to initiate treatment with prescription moisturizers (e.g., ceramide containing products like EpiCeram®) or moisturizers containing additives (ceramide, hyaluronic acid, urea, filaggrin degradation products) during the screening period or during the study. Patients could continue using stable doses of such moisturizers if initiated before the screening visit.

Starting on day −14, all patients were required to initiate treatment with TCS using a standardized regimen according to the following guidelines:

Apply medium potency TCS once daily to areas with active lesions. Based on investigator discretion, low potency TCS may be used once daily on areas of thin skin (face, neck, intertriginous, and genital areas, areas of skin atrophy, etc.) or for areas where continued treatment with medium potency TCS is considered unsafe.

Once the patient achieves an IGA score of 2 or less, decrease the frequency of use of medium potency TCS to 3 times per week, and then stop once lesions are clear (IGA 0). Patients should be instructed to use TCS only on active lesions, and to stop use of TCS if lesions clear completely in between clinic visits.

If lesions return, reinstitute treatment with medium potency TCS, with the same step-down approach described above upon lesion resolution.

In case there are signs of local (e.g., impending skin atrophy), or systemic TCS toxicity with medium potency steroids, patients should be switched to low potency steroids.

For lesions persisting or worsening under daily treatment with medium potency TCS, patients may be treated (rescued) with high potency TCS (super-potent/very-high potency steroids are not allowed even for rescue), unless higher potency TCS are considered unsafe (a potent TCS should normally be restricted to use on non-delicate skin sites [excluding face, flexures, groin], and should not be used for a prolonged period in order to prevent the development of cutaneous atrophy and adrenal axis suppression. Low potency steroids should normally be used for delicate skin sites (face, flexures, groin) during these flares.

A list of acceptable steroids for use was provided to investigators. It was recommended that patients use triamcinolone acetonide 0.1% cream, fluocinolone acetonide 0.025% cream, or clobetasone butyrate 0.05% for medium potency, and hydrocortisone acetate 1% cream for low potency. If rescue with TCS was needed, it was recommended that patients use mometasone furoate 0.1% ointment as high potency steroid. Patients having tolerance issues with any of these steroids, or if steroids were not commercially available, were able to substitute with products of the same potency from the list provided in the study reference manual. The use of very-high potency or super-potent TCS was prohibited during the study, as their use is not recommended in patients under 12 years of age.

Rescue treatment: Rescue treatment for AD was available to patients during the study according to the following guidelines: Investigators will be required to perform an IGA assessment prior to starting rescue treatment and initiate rescue treatment only in patients who either have an IGA score=4, or have intolerable symptoms. If possible, investigators are encouraged to consider rescue initially with topical treatment (e.g., high potency TCS) and to escalate to systemic medications only for patients who do not respond adequately after at least 7 days of topical treatment. Patients may continue study treatment if rescue consists of topical medications. The use of very high potency or superpotent TCS is prohibited. Very-high-potency topical corticosteroids include:

Betamethasone dipropionate augmented 0.05% ointment

Clobetasol propionate 0.05% solution, foam, cream or ointment

Diflorasone diacetate 0.05% ointment

Halobetasol propionate 0.05% cream or ointment.

Patients receiving systemic corticosteroids or systemic non-steroidal immunosuppressive drugs (e.g., cyclosporine, methotrexate, mycophenolate-mofetil, azathioprine, etc.) as rescue medication during the study were discontinued permanently from the study drug.

Procedures and Assessments

A variety of parameters was collected during the study to assess efficacy and safety of the dupilumab therapy. Efficacy parameters included patient reported assessments, including worst itch score, patient global impression of disease, patient global impression of change, CDLQI, POEM, DFI, Patient Reported Outcomes Measurements Information Systems (PROMIS) anxiety and depression scores, Faces pain scale, and investigator-reported assessments (including BSA affected by AD, SCORAD, Global Individual Signs Score [GISS], and EASI that measure the extent and severity of AD, and the IGA that rates the overall severity of AD). Safety parameters included vital signs, physical examinations, clinical laboratory tests, 12-lead electrocardiograms (ECGs), and clinical evaluations. Patients were asked to monitor all adverse events (AEs) experienced from the time of informed consent/assent until their last study visit.

Efficacy Assessment

Patient Assessment of Pruritus Using Worst Itch Scale: The worst itch scale is a simple assessment tool that patients use to report the intensity of their pruritus (itch). This is an 11-point scale (0 to 10) in which 0 indicates no itching while 10 indicates worst itching possible. Patients were asked the following 2 questions:

"What was the worst itch you had today?"

"What was the worst itch you had last night?"

Patients were asked to provide answers to these 2 questions daily throughout the entire study. Both questions were answered in the evening and the daily worst itch score was calculated as the worse of the scores for the 2 questions.

Patient Global Impression of Disease: Patients rated their disease based on the 5-level scale as follows: "In general, how itchy have you been during the last 7 days?"•Not itchy at all•A little itchy•Medium itchy•Pretty itchy•Very itchy. Patients underwent this assessment at screening, at baseline and days 15, 29, 57, 85, and 113 (end of study) or early termination.

Patient Global Impression of Chance: Patients rated their disease based on the 5-level scale as follows: "Since you started your study medication, how has your itching changed?"•Much better•A little better•The same•A little worse•Much worse. Patients underwent this assessment at screening and days 15, 29, 57, 85, and 113 (end of study) or early termination.

Children's Dermatology Life Quality Index: The CDLQI is a validated questionnaire designed to measure the impact of skin disease on the QOL in children (Lewis-Jones et al 1995, *Brit. J. Dermatol.* 132: 942-9). The aim of the questionnaire was to measure how much a patient's skin problem has affected the patient over a recall period of the past week. To complete the questionnaire, patients need to provide responses to 10 questions (the questions focus on domains such as symptoms, feelings associated with disease, the impact of the disease on leisure, school or holidays, personal relationships, sleep, and side effects of treatment for the skin disease). The instrument has a recall period of 7 days. Nine of the 10 questions are scored as follows: •Very much=3•Quite a lot=2•Only a little=1•Not at all=0•Question unanswered=0 Question 7 has an additional possible response (prevented school), which is assigned a score of 3. The CDLQI for a patient is the sum of the score of each question with a maximum of 30 and a minimum of 0. The higher the score, the greater the impact is on the QOL. The CDLQI can also be expressed as a percentage of the maximum possible score of 30. Patients underwent this assessment at screening, baseline, and on days 15, 29, 57, 85, and 113 (end of study) or early termination.

Patient Oriented Eczema Measure: The POEM is a 7-item, validated questionnaire used in clinical practice and clinical trials to assess disease symptoms in children and adults (Charman et al 2004, *Arch. Dermatol.* 140: 1513-9). The format is a response to 7 items (dryness, itching, flaking, cracking, sleep loss, bleeding, and weeping) based on frequency of these disease symptoms during the past week (i.e., 0=no days, 1=1 to 2 days, 2=3 to 4 days, 3=5 to 6 days, and 4=all days) with a scoring system of 0 to 28; the total score reflects disease-related morbidity. The questionnaire was administered at screening, baseline and on days 15, 29, 57, 85, and 113 (end of study) or early termination.

Dermatitis Family Index: The DFI assesses the impact of having a child with AD on family QOL (Lawson 1998). The 10-item disease specific questionnaire was formed after ethnographical interviews and focus groups revealed the areas of family QOL affected by AD. The self-administered instrument is completed by an adult family member of a child affected by dermatitis. The items inquire about housework, food preparation, sleep, family leisure activity, shopping, expenditure, tiredness, emotional distress, relationships and the impact of helping with treatment on the primary caregiver's life. The DFI questions are scored on a four-point Likert scale ranging from 0 to 3, so that the total DFI score ranges from 0 to 30. The time frame of reference is the past week. A higher DFI score indicates greater impairment in family QOL as affected by AD. The questionnaire was administered at screening, baseline and on days 15, 29, 57, 85, and 113 (end of study) or early termination.

Faces Pain Scale—Revised: The Faces Pain Scale—Revised (FPS-R) is a self-report measure of pain intensity developed for children (Hicks 2001). It was adapted from the Faces Pain Scale to make it possible to score the sensation of pain on the widely accepted 0 to 10 metric. The scale shows a close linear relationship with visual analog pain scales across the age range of 4 to 16 years. It is easy to administer and requires no equipment except for the photocopied faces. The instrument has well established psychometric properties and has been validated in school-going children. The questionnaire was administered at baseline and on days 15, 29, 57, and 85 or early termination.

PROMIS Anxiety and Depression Scale: The PROMIS Anxiety instrument measures self-reported fear (fearfulness, panic), anxious misery (worry, dread), hyperarousal (tension, nervousness, restlessness), and somatic symptoms related to arousal (racing heart, dizziness). The PROMIS Depression instrument assesses self-reported negative mood (sadness, guilt), views of self (self-criticism, worthlessness), and social cognition (loneliness, interpersonal alienation), as well as decreased positive affect and engagement (loss of interest, meaning, and purpose). The instrument was administered at screening, baseline and on days 15, 29, 57, 85, and 113 (end of study) or early termination.

Investiaator's Global Assessment: The IGA is an assessment instrument used in clinical studies to rate the severity of AD globally, based on a 5-point scale ranging from 0 (clear) to 4 (severe). The IGA score was assessed at screening, baseline and on days 8, 15, 22, 29, 57, 85, and 113 (end of study) or early termination.

Eczema Area and Severity Index: The EASI is a validated measure used in clinical practice and clinical trials to assess the severity and extent of AD (Hanifin et al 2001, *Exp. Dermatol.* 10: 11-18). The EASI is a composite index with scores ranging from 0 to 72. Four AD disease characteristics (erythema, thickness [induration, papulation, edema], scratching [excoriation], and lichenification) each are assessed for severity by the investigator or designee on a scale of "0" (absent) through "3" (severe). In addition, the area of AD involvement is assessed as a percentage by body area of head, trunk, upper limbs, and lower limbs, and converted to a score of 0 to 6. In each body region, the area is expressed as 0, 1 (1% to 9%), 2 (10% to 29%), 3 (30% to 49%), 4 (50% to 69%), 5 (70% to 89%), or 6 (90% to 100%). The EASI was collected at screening, baseline and on days 8, 15, 22, 29, 57, 85, and 113 (end of study) or early termination.

Global Individual Signs Score: Individual components of the AD lesions (erythema, infiltration/papulation, excoriations, and lichenification) are rated globally (i.e., each assessed for the whole body, not by anatomical region) on a 4-point scale (from 0=none to 3=severe) using the EASI severity grading criteria. The Global Individual Signs Score (GISS) was assessed at screening, baseline and on days 8, 15, 22, 29, 57, 85, and 113 (end of study) or early termination.

SCORing Atopic Dermatitis: The SCORing Atopic Dermatitis (SCORAD) is a validated tool used in clinical research and clinical practice that was developed to standardize the evaluation of the extent and severity of AD (European Task Force on Atopic Dermatitis 1993, *Dermatol.* 186: 23-31). There are 3 components to the assessment A=extent or affected BSA, B=severity, and C=subjective symptoms. The extent of AD is assessed as a percentage of each defined body area and reported as the sum of all areas, with a maximum score of 100% (assigned as "A" in the overall SCORAD calculation). The severity of 6 specific symptoms of AD (redness, swelling, oozing/crusting, excoriation, skin thickening/lichenification, and dryness) is assessed using the following scale: none (0), mild (1), moderate (2), or severe (3) (for a maximum of 18 total points, assigned as "B" in the overall SCORAD calculation). Subjective assessment of itch and sleeplessness is recorded for each symptom by the patient or relative on a Visual Analogue Scale, where 0 is no itch (or sleeplessness) and 10 is the worst imaginable itch (or sleeplessness), with a maximum possible score of 20. This parameter is assigned as "C" in the overall SCORAD calculation. The SCORAD is calculated as: A/5+7B/2+C where the maximum is 103. Patients underwent this assessment at screening, baseline and on days 8, 15, 22, 29, 57, 85, and 113 (end of study) or early termination.

Body Surface Area Involvement of Atopic Dermatitis: Body surface area affected by AD is assessed for each section of the body using the rule of nines (the possible highest score for each region is: head and neck [9%], anterior trunk [18%], back [18%], upper limbs [18%], lower limbs [36%], and genitals [1%]) and is reported as a percentage of all major body sections combined. Patients underwent this assessment at screening, baseline and on days 8, 15, 22, 29, 57, 85, and 113 (end of study) or early termination.

Assessment of Missed School Days: Patients who are enrolled in school are asked to report the number of missed school days since the last study assessment. Patients underwent this assessment at baseline and on days 29, 57, 85, and 113 (end of study) or early termination.

Caregiver Assessment of Missed Workdays: This questionnaire asks the caregiver to report the impact of having a child with AD on their workdays. Caregivers who were employed were asked to report the number of sick-leave days since the last study assessment. Caregivers underwent this assessment at baseline and on days 29, 57, 85, and 113 (end of study) or early termination.

Topical Corticosteroids Accountability: At every in-clinic visit following the TCS standardization visit, the type, amount, frequency, and potency of TCS used was recorded by site personnel. The amount of TCS used was determined by weighing the tube at each visit through the end of the study.

Safety Assessment

Safety was assessed by monitoring vital signs, physical examinations, clinical laboratory tests, 12-lead electrocardiograms (ECGs), clinical evaluations, and by monitoring adverse events (AEs) and Serious Adverse Events.

An Adverse Event (AE) is any untoward medical occurrence in a subject or clinical investigation subject administered a pharmaceutical product. An AE can, therefore, be any unfavorable and unintended sign (including abnormal laboratory finding), symptom, or disease temporally associated with the use of a medicinal product, whether or not considered related to the medicinal (investigational) product. AEs also include: any worsening (i.e., any clinically significant change in frequency and/or intensity) of a pre-existing condition that is temporally associated with the use of the study drug; abnormal laboratory findings considered by the Investigator to be clinically significant; and any untoward medical occurrence.

A Serious Adverse Event (SAE) is any untoward medical occurrence that at any dose results in death; is life-threatening; requires in-patient hospitalization or prolongation of existing hospitalization; results in persistent or significant disability/incapacity; is a congenital anomaly/birth defect; or is an important medical event.

Statistical Analyses

For primary efficacy analyses, the Cochran-Mantel-Haenszel test adjusted by randomization strata (baseline weight group and region) was used for analyzing the percentage of patients with IGA 0 or 1 at week 16 or percentage of patients with EASI-75 at week 16. The Mantel-Fleiss (MF) criterion was checked, and if not met, sensitivity analyses including each stratification factor separately in CMH test were conducted.

To account for the impact of rescue treatment on the efficacy effect: For the primary efficacy endpoints (which are binary efficacy endpoints), if rescue treatment was used, the patient was classified as a nonresponder from the time the rescue is used. If a patient withdrew from study, this patient was counted as a nonresponder for endpoints after withdrawal.

Sensitivity analysis using the last observation carried forward (LOCF) approach to determine patients status at week 16 was conducted to assess the robustness of the primary efficacy analysis with regards to handling of missing data. The efficacy data was set to missing after rescue treatment is used, then the LOCF method used to determine patients' status at week 16. In addition, the Cochran-Mantel-Haenszel method adjusted by randomization strata was performed on all observed data regardless if rescue treatment is used. A patient with missing data was counted as a non-responder.

Results

Baseline Characteristics

Baseline demographics and disease characteristics are summarized in Tables 1A-1B, 2, and 3A-B.

TABLE 1A

| | Baseline Demographics (Overall) | | | |
|---|---|---|---|---|
| N (Full Analysis Set (FAS)) | Pbo + TCS 123 | Q4W + TCS 122 | Q2W + TCS 122 | Overall 367 |
| Age (years), mean (SD) | 8.3 (1.76) | 8.5 (1.74) | 8.5 (1.68) | 8.5 (1.72) |
| ≥ 6 – < 9 | 57 (46.3%) | 60 (49.2%) | 58 (47.5%) | 175 (47.7%) |
| ≥ 9 – < 12 | 66 (53.7%) | 62 (50.8%) | 64 (52.5%) | 192 (52.3%) |

TABLE 1A-continued

| Baseline Demographics (Overall) | | | | |
|---|---|---|---|---|
| N (Full Analysis Set (FAS)) | Pbo + TCS 123 | Q4W + TCS 122 | Q2W + TCS 122 | Overall 367 |
| Gender (Male), n (%) | 61 (49.6%) | 57 (46.7%) | 65 (53.3%) | 183 (49.9%) |
| Race, n (%) | | | | |
| White | 77 (62.6%) | 89 (73.0%) | 88 (72.1%) | 254 (69.2%) |
| Black or African American | 23 (18.7%) | 19 (15.6%) | 20 (16.4%) | 62 (16.9%) |
| Asian | 13 (10.6%) | 5 (4.1%) | 10 (8.2%) | 28 (7.6%) |
| Weight (kg), mean (SD) | 31.5 (10.82) | 31.0 (9.40) | 32.1 (10.79) | 31.5 (10.34) |
| <30 kg | 61 (49.6%) | 61 (50.0%) | 63 (51.6%) | 185 (50.4%) |
| >30 kg | 62 (50.4%) | 61 (50.0%) | 59 (48.4%) | 182 (49.6%) |
| BMI (kg/m$^2$), mean (SD) | 17.9 (3.90) | 17.6 (2.93) | 18.0 (3.68) | 17.8 (3.53) |

TABLE 1B

| | Baseline Demographics (by Baseline Weight) | | | | | |
|---|---|---|---|---|---|---|
| | Baseline weight <30 kg | | | Baseline weight ≥30 kg | | |
| | Placebo + TCS (n = 61) | 300 mg q4w + TCS (n = 61) | 100 mg q2w + TCS (n = 63) | Placebo + TCS (n = 62) | 300 mg q4w + TCS (n = 61) | 200 mg q2w + TCS (n = 59) |
| Age, mean (SD), years | 7.1 (1.3) | 7.5 (1.4) | 7.6 (1.4) | 9.5 (1.3) | 9.5 (1.5) | 9.5 (1.4) |
| Race, n (%) | | | | | | |
| White | 40 (65.6) | 45 (73.8) | 43 (68.3) | 37 (59.7) | 44 (72.1) | 45 (76.3) |
| Black/African American | 9 (14.8) | 9 (14.8) | 12 (19.0) | 14 (22.6) | 10 (16.4) | 8 (13.6) |
| Asian | 7 (11.5) | 4 (6.6) | 6 (9.5) | 6 (9.7) | 1 (1.6) | 4 (6.8) |
| Other | 4 (6.6) | 3 (4.9) | 1 (1.6) | 5 (8.1) | 5 (8.2) | 1 (1.7) |
| Not reported/missing | 1 (1.6) | 0 | 1 (1.6) | 0 | 1 (1.6) | 1 (1.7) |
| Gender (Male), n (%) | 30 (49.2) | 27 (44.3) | 32 (50.8) | 31 (50.0) | 30 (49.2) | 33 (55.9) |
| Weight (kg), mean (SD) | 23.3 (3.4) | 23.8 (3.0) | 24.5 (3.5) | 39.5 (9.5) | 38.1 (8.0) | 40.2 (10.0) |
| Weight group, n (%) | | | | | | |
| <30 kg | 61 (100) | 61 (100) | 63 (100) | 0 | 0 | 0 |
| >30 kg | 0 | 0 | 0 | 62 (100) | 61 (100) | 59 (100) |
| BMI (kg/m$^2$), mean (SD) | 16.0 (2.5) | 15.7 (1.3) | 16.1 (1.7) | 19.8 (4.1) | 19.5 (2.9) | 20.2 (4.0) |

TABLE 2

| | Concurrent Conditions and Prior Medications | | | |
|---|---|---|---|---|
| N (SAF) | Pbo + TCS N = 120 | Q4W + TCS N = 120 | Q2W + TCS N = 122 | Overall N = 362 |
| # of patients with ≥ 1 concurrent allergic condition excluding AD | 111 (92.5%) | 107 (89.2%) | 114 (93.4%) | 332 (91.7%) |
| ALLERGIC RHINITIS | 72 (60.0%) | 73 (60.8%) | 73 (59.8%) | 218 (60.2%) |
| ASTHMA | 54 (45.0%) | 55 (45.8%) | 60 (49.2%) | 169 (46.7%) |
| FOOD ALLERGY | 83 (69.2%) | 75 (62.5%) | 75 (61.5%) | 233 (64.4%) |
| ALLERGIC CONJUNCTIVITIS | 16 (13.3%) | 14 (11.7%) | 14 (11.5%) | 44 (12.2%) |
| HIVES | 8 (6.7%) | 14 (11.7%) | 14 (11.5%) | 36 (9.9%) |
| CHRONIC RHINOSINUSITIS | 4 (3.3%) | 5 (4.2%) | 2 (1.6%) | 11 (3.0%) |
| NASAL POLYPS | 0 | 0 | 2 (1.6%) | 2 (0.6%) |
| EOSINOPHILIC ESOPHAGITIS | 0 | 1 (0.8%) | 1 (0.8%) | 2 (0.6%) |

TABLE 2-continued

| | Concurrent Conditions and Prior Medications | | | |
|---|---|---|---|---|
| N (SAF) | Pbo + TCS N = 120 | Q4W + TCS N = 120 | Q2W + TCS N = 122 | Overall N = 362 |
| OTHER ALLERGIES | 81 (67.5%) | 67 (55.8%) | 79 (64.8%) | 227 (62.7%) |
| History of systemic medication for AD, n/N1 (%) | 36/120 (30.0) | 42/120 (35.0) | 40/122 (32.8) | |
| Patients receiving prior corticosteroids | 17/120 (14.2) | 25/120 (20.8) | 30/122 (24.6) | |
| Patients receiving prior systemic nonsteroidal immunosuppressants | 22/120 (18.3) | 23/120 (19.2) | 16/122 (13.1) | |
| Azathioprine | 0 | 2/120 (1.7) | 2/122 (1.6) | |
| Cyclosporine | 12/120 (10.0) | 17/120 (14.2) | 11/122 (9.0) | |
| Methotrexate | 11/120 (9.2) | 7/120 (5.8) | 3/122 (2.5) | |
| Mycophenolate | 2/120 (1.7) | 2/120 (1.7) | 1/122 (0.8) | |
| Eosinophils, median (Q1–Q3), × $10^9$/L | 0.7 (0.4-1.1) | 0.8 (0.4-1.1) | 0.6 (0.4-1.2) | |

TABLE 3A

| | Baseline Disease Characteristics (Overall) | | | |
|---|---|---|---|---|
| N (FAS) | Pbo + TCS 123 | Q4W + TCS 122 | Q2W +TCS 122 | Overall 367 |
| Duration of AD (yr), mean (SD) | 7.2 (2.15) | 7.4 (2.44) | 7.2 (2.31) | 7.3 (2.30) |
| EASI score (0-72), mean (SD) | 39.0 (12.01) | 37.4 (12.45) | 37.3 (10.86) | 37.9 (11.79) |
| IGA (0-4), n (%) | | | | |
| 3 | 0 | 1 (0.8%) | 0 | 1 (0.3%) |
| 4 | 123 (100%) | 121 (99.2%) | 122 (100%) | 366 (99.7%) |
| Peak Pruritus NRS [0-10], mean (SD) | 7.7 (1.54) | 7.8 (1.58) | 7.8 (1.52) | 7.8 (1.54) |
| POEM (0-30), mean (SD) | 20.7 (5.48) | 21.3 (5.51) | 20.5 (5.50) | 20.9 (5.49) |
| CDLQI (0-30), mean (SD) | 14.6 (7.41) | 16.2 (7.85) | 14.5 (6.78) | 15.1 (7.38) |
| SCORAD (0-103), mean (SD) | 72.9 (12.01) | 75.6 (11.71) | 72.3 (10.83) | 73.6 (11.59) |
| BSA involvement (%), mean (SD) | 60.2 (21.46) | 54.8 (21.58) | 57.8 (20.04) | 57.6 (21.10) |
| DFI, mean (SD) | 15.0 (7.5) | 16.9 (8.7) | 14.9 (7.1) | |
| PROMIS anxiety, mean (SD) | 57.3 (11.6) | 59.8 (13.7) | 58.6 (11.3) | |
| PROMIS depression, mean (SD) | 55.0 (12.1) | 58.1 (12.8) | 56.3 (11.2) | |

TABLE 3B

| | Baseline Disease Characteristics (by Baseline Weight) | | | | | |
|---|---|---|---|---|---|---|
| | Baseline weight <30 kg | | | Baseline weight ≥30 kg | | |
| | Placebo + TCS (n = 61) | 300 mg q4w + TCS (n = 61) | 100 mg q2w + TCS (n = 63) | Placebo + TCS (n = 62) | 300 mg q4w + TCS (n = 61) | 200 mg q2w + TCS (n = 59) |
| Duration of AD (yr), mean (SD) | 6.3 (1.7) | 6.8 (1.7) | 6.4 (2.1) | 8.0 (2.2) | 8.0 (2.9) | 8.1 (2.3) |
| EASI score (0-72), mean (SD) | 38.9 (12.6) | 36.9 (12.4) | 37.5 (10.0) | 39.0 (11.5) | 37.8 (12.6) | 37.1 (11.8) |
| Weekly average of daily NRS, mean (SD) | 7.6 (1.6) | 7.9 (1.5) | 7.9 (1.5) | 7.8 (1.5) | 7.7 (1.7) | 7.6 (1.5) |
| BSA, mean (SD) | 62.0 (20.9) | 54.6 (21.9) | 61.5 (19.4) | 58.4 (22.1) | 54.9 (21.4) | 53.9 (20.2) |
| SCORAD, mean (SD) | 73.0 (12.6) | 75.5 (12.6) | 73.3 (10.4) | 72.8 (11.5) | 75.8 (10.9) | 71.2 (11.3) |
| CDLQI, mean (SD) | 16.1 (6.9) | 16.9 (8.1) | 16.0 (7.0) | 13.2 (7.7) | 15.5 (7.7) | 13.0 (6.3) |

TABLE 3B-continued

| | Baseline Disease Characteristics (by Baseline Weight) | | | | | |
|---|---|---|---|---|---|---|
| | Baseline weight <30 kg | | | Baseline weight ≥30 kg | | |
| | Placebo + TCS (n = 61) | 300 mg q4w + TCS (n = 61) | 100 mg q2w + TCS (n = 63) | Placebo + TCS (n = 62) | 300 mg q4w + TCS (n = 61) | 200 mg q2w + TCS (n = 59) |
| POEM, mean (SD) | 21.1 (4.9) | 21.5 (6.0) | 21.1 (5.6) | 20.4 (6.0) | 21.1 (5.1) | 19.9 (5.3) |
| DFI, mean (SD) | 16.1 (7.6) | 17.7 (8.9) | 16.2 (6.8) | 14.0 (7.4) | 16.1 (8.4) | 13.5 (7.1) |
| PROMIS anxiety, mean (SD) | 58.9 (11.8) | 60.3 (13.6) | 60.6 (10.5) | 55.8 (11.4) | 59.3 (13.8) | 56.5 (11.8) |
| PROMIS depression, mean (SD) | 54.4 (12.3) | 58.8 (13.1) | 57.8 (10.6) | 55.6 (11.9) | 57.4 (12.5) | 54.7 (11.7) |

Baseline demographics were comparable across the three treatment groups. Patients in this study had a mean age of 8.5 years and had a long duration of AD (mean of 7.3 years). A high incidence of atopic co-morbidity was observed across all treatment groups. Overall, 91.7% of patients had at least one concurrent allergic condition. The mean BSA affected by AD was 57.6%. Nearly all (99.7%) patients had IGA 4 (severe disease). Mean EASI score was 37.9. Mean Peak Pruritis NRS score was 7.8. Mean POEM score was 20.9/30. On average, patients reported a very large effect on quality of life (mean CDLQI score 15.1/30). Mean SCORAD score was 73.6/103.

For the patients who were randomized and treated, high patient retention was observed for all treatment groups (Table 4).

TABLE 4

| Patient Treatment Disposition | | | | | |
|---|---|---|---|---|---|
| | Pbo + TCS | Q4W + TCS | Q2W + TCS | Combined | Total |
| Patients randomized | 123 | 122 | 122 | 244 | N = 367 |
| Patients randomized and treated | 121 (98.4%) | 120 (98.4%) | 121 (99.2%) | 241 (98.8%) | 362 (98.6%) |
| Completed the study treatment, n (%) | 114 (92.7%) | 118 (96.7%) | 119 (97.5%) | 237 (97.1%) | 351 (95.6%) |
| Discontinuation study treatment, n (%) | 9 (7.3%) | 4 (3.3%) | 3 (2.5%) | 7 (2.9%) | 16 (4.4%) |
| Adverse event | 1 (0.8%) | 0 | 1 (0.8%) | 1 (0.4%) | 2 (0.5%) |
| Lack of efficacy | 2 (1.6%) | 0 | 0 | 0 | 2 (0.5%) |
| Patient mis-stratified | 0 | 0 | 1 (0.8%) | 1 (0.4%) | 1 (0.3%) |
| Patient randomized in error | 1 (0.8%) | 1 (0.8%) | 1 (0.8%) | 2 (0.8%) | 3 (0.8%) |
| Use of prohibited medication | 1 (0.8%) | 1 (0.8%) | 0 | 1 (0.4%) | 2 (0.5%) |
| Withdrew consent | 4 (3.3%) | 2 (1.6%) | 0 | 2 (0.8%) | 6 (1.6%) |

Efficacy

Both dupilumab+TCS regimens (weight-tiered 100/200 mg Q2W+TCS and non-weight-tiered 300 mg Q4W+TCS) vs placebo+TCS significantly improved all prespecified efficacy endpoints. Tables 5A-5B3 and 6A-61B summarize improvements in various AD-associated parameters in patents treated with dupilumab.

TABLE 5A

| Efficacy Results for Co-Primary and Secondary Endpoints (Overall) | | | | |
|---|---|---|---|---|
| | | AD-1652 FAS | | |
| | Endpoint | Pbo + TCS | 300 mg Q4W + TCS | 100/200 mg Q2W + TCS |
| | N (FAS) | 123 | 122 | 122 |
| Co-Primary | IGA 0/1, n (%) | 14 (11.4%) | 40 (32.8%)¶ | 36 (29.5%)* |
| | EASI-75, n (%) | 33 (26.8%) | 85 (69.7%)¶ | 82 (67.2%)¶ |

TABLE 5A-continued

Efficacy Results for Co-Primary and Secondary Endpoints (Overall)

|  | Endpoint | Pbo + TCS | AD-1652 FAS 300 mg Q4W + TCS | 100/200 mg Q2W + TCS |
|---|---|---|---|---|
| Key Secondary | % change EASI, LS Mean (SE) | −48.6 (2.46) | −82.1 (2.37)¶ | −78.4 (2.35)¶ |
|  | % change Pruritus NRS, LS Mean (SE) | −25.9 (2.90) | −54.6 (2.89)¶ | −57.0 (2.77)¶ |
| Other Secondary | ≥4 point reduction in PNRS, n/N1[1] (%) | 15/122 (12.3%) | 61/120 (50.8%)¶ | 70/120 (58.3%)¶ |
|  | ≥3 point reduction in PNRS, n/N1[1] (%) | 26/123 (21.1%) | 73/121 (60.3%)¶ | 81/120 (67.5%)¶ |
|  | EASI-50, n (%) | 53 (43.1%) | 111 (91.0%)¶ | 101 (82.8%)¶ |
|  | EASI-90, n (%) | 9 (7.3%) | 51 (41.8%)¶ | 37 (30.3%)¶ |
|  | Change POEM, LS Mean (SE) | −5.3 (0.69) | −13.6 (0.65) | −13.4 (0.65)¶ |
|  | Change CDLQI, LS Mean (SE) | −6.4 (0.51) | −10.6 (0.47) | −10.7 (0.46)¶ |
|  | % change SCORAD, LS Mean (SE) | −29.8 (2.26) | −62.4 (2.13) | −60.2 (2.11)¶ |

*P<0.001;
†P <0.05;
¶P <0.0001;
‡P<0.01;
§nominal P value.
[1] N1 is the number of patients with baseline pruritus NRS ≥4 (3);
* p-value = 0.0004.
LS, least squares;
SE, standard error.

TABLE 5B

Efficacy Results for Co-Primary and Secondary Endpoints (by Baseline Weight)

|  | Baseline weight <30 kg | | | Baseline weight ≥30 kg | | |
|---|---|---|---|---|---|---|
|  | Placebo + TCS (n = 61) | 300 mg Q4W + TCS (n = 61) | 100 mg Q2W + TCS (n = 63) | Placebo + TCS (n = 62) | 300 mg Q4W + TCS (n = 61) | 200 mg Q2W + TCS (n = 59) |
| Co-primary endpoints | | | | | | |
| Proportion of patients with IGA 0/1, n (%) | 8 (13.1) | 18 (29.5) §† | 13 (20.6) | 6 (9.7) | 22 (36.1) †* | 23 (39.0) §* |
| Proportion of patients with EASI-75, n (%) | 17 (27.9) | 46 (75.4) §¶ | 38 (60.3) §* | 16 (25.8) | 39 (63.9) §¶ | 44 (74.6) §¶ |
| Secondary endpoints | | | | | | |
| % change in EASI, LS mean ± SE | −49.1 (3.3) | −84.3 (3.0) §¶ | −76.7 (3.0) §¶ | −48.3 (3.6) | −79.9 (3.6) §¶ | −80.4 (3.6) §¶ |
| Proportion of patients with EASI-50, n (%) | 26 (42.6) | 58 (95.1) §¶ | 50 (79.4) §¶ | 27 (43.5) | 53 (86.9) §¶ | 51 (86.4) §¶ |
| % change in weekly average of Daily Peak Pruritus NRS, LS mean ± SE | −27.0 (4.2) | −55.1 (3.9) §¶ | −56.1 (3.9) §¶ | −25.0 (4.0) | −54.3 (4.2) §¶ | −58.2 (4.0) §¶ |
| Proportion of patients with ≥4-point reduction in weekly average of daily Peak Pruritus NRS, n/N1 (%) | 7/60 (11.7) | 33/61 (54.1) §¶ | 35/63 (55.6) §¶ | 8/62 (12.9) | 28/59 (47.5) §¶ | 35/57 (61.4) §¶ |
| Proportion of patients with ≥3-point reduction in weekly average of daily Peak Pruritus NRS, n/N2 (%) | 11/61 (18.0) | 38/61 (62.3) §¶ | 43/63 (68.3) §¶ | 15/62 (24.2) | 35/60 (58.3) §* | 38/57 (66.7) §¶ |
| Proportion of patients with EASI-90, n (%) | 4 (6.6) | 28 (45.9) §¶ | 16 (25.4) §‡ | 5 (8.1) | 23 (37.7) §¶ | 21 (35.6) §* |
| Change in POEM, LS mean ± SE | −5.9 (1.0) | −14.0 (1.0) §¶ | −13.3 (0.9) §¶ | −4.7 (0.9) | −13.2 (0.9) §¶ | −13.6 (0.9) §¶ |
| Change in CDLQI, LS mean ± SE | −7.2 (0.8) | −11.5 (0.7) §¶ | −11.6 (0.7) §¶ | −5.6 (0.7) | −9.7 (0.6) §¶ | −9.8 (0.6) §¶ |
| % change in SCORAD, LS mean ± SE | −28.9 (3.1) | −65.3 (2.9) §¶ | −58.1 (2.8) §¶ | −30.7 (3.3) | −59.3 (3.1) §¶ | −62.7 (3.1) §¶ |

*P < 0.001; †P < 0.05; ¶P < 0.0001; ‡P < 0.01; §nominal P value.
N1, number of patients with baseline NRS score ≥4 and non-missing values at each visit; N2, number of patients with baseline NRS score n and non-missing values at each visit; LS, least squares; SE, standard error.

TABLE 6A

Efficacy Results for Other Secondary Endpoints (Overall)

| Endpoint | AD-1652 FAS | | |
|---|---|---|---|
| | Pbo + TCS | 300 mg Q4W + TCS | 100/200 mg Q2W + TCS |
| N(FAS) | 123 | 122 | 122 |
| Change from baseline to week 16 in NRS, LSMean (SE)/Diff | −2.05 (0.215) | −4.22 (0.207)/−2.18 | −4.45 (0.206)/−2.41 |
| Change from baseline to week 16 in BSA, LSMean (SE)/Diff | −21.65 (1.72) | −40.53 (1.648)/−18.88 | −39.37 (1.629)/−17.72 |
| Time to onset of effect on pruritus (≥4 point reduction of NRS from baseline), Median/HR | NC | 10 (7,13)/2.921 | 10.0 (8,12)/3.114 |
| Time to onset of effect on pruritus (≥3 point reduction of NRS from baseline), Median/HR | NC | 6 (5,9)/2.075 | 5 (5,7)/2.278 |
| Change from baseline in Dermatitis Family Index (DFI), LSMean (SE)/Diff | −6.77 (0.497) | −10.75 (0.476)/−3.98 | −10.89 (0.469)/−4.11 |
| Change from baseline Patient Reported Outcomes Measurements Information Systems (PROMIS) pediatric anxiety score, LSMean (SE)/Diff | −9.48 (0.855) | −12.30 (0.807)/−2.82* | −12.62 (0.806)/−3.14** |
| Change from baseline in PROMIS pediatric depressive symptoms score, LSMean (SE)/Diff | −7.42 (0.848) | −12.84 (0.793)/−5.42 | −11.92 (0.790)/−4.50 |
| Proportion of TCS medication-free days, Mean (SD) | 0.11 (0.184) | 0.20 (0.232)** | 0.19 (0.207)** |
| Mean weekly dose of TCS for low/medium-potency TCS, LSMean (SE)/Diff | 20.1 (1.37) | 15.0 (1.36)/−5.1** | 14.4 (1.38)/−5.7** |
| Mean weekly dose of TCS for high-potency TCS, LSMean (SE)/Diff | 4.2 (1.18) | 6.9 (1.70)/2.7# | 5.8 (0.83)/1.6# |
| Incidence of skin-infection TEAEs (excluding herpetic infections) through week 16, n (%)/Diff | 16 (13.0%) | 7 (5.7%)/−7.3%# | 10 (8.2%)/−4.8%# |
| Incidence of SAEs, n (%)/Diff | 2 (1.6%) | 2 (1.6%)/0%# | 0/−1.6%# |
| Change in SCORAD sleep component VAS, LS mean ± SE$^a$ | −2.0 (0.3) | −4.3 (0.2)¶ | −4.5 (0.2)¶ |
| Change in POEM sleep item, LS mean ± SE$^b$ | −1.0 (0.1) | −2.1 (0.1)¶ | −2.1 (0.1)¶ |
| Change in CDLQI sleep item, LS mean ± SE$^c$ | −0.6 (0.1) | −1.4 (0.1)¶ | −1.4 (0.1)¶ |

Nominal P-values are provided for the endpoints not in hierarchy.
No asterisk means P-value <0.001,
# means P-value ≥ 0.05,
* means P-value < 0.05,
¶ means P-value < 0.0001,
** means P-value < 0.01.
Sleeplessness was assessed by the $^a$SCORAD sleep component - a visual analog scale with a maximum score of 10, indicating the worst imaginable sleeplessness;
$^b$ POEM sleep item ("Over the last week, on how many nights has your sleep been disturbed because of the eczema?");
$^c$ CDLQI sleep item ("Over the last week, how much has your sleep been affected by your skin problem?").
LS, least squares;
SE, standard error.

TABLE 6B

Efficacy Results for Other Secondary Endpoints (by Baseline Weight)

| | Baseline weight <30 kg | | | Baseline weight ≥30 kg | | |
|---|---|---|---|---|---|---|
| | Placebo + TCS (n = 61) | 300 mg Q4W + TCS (n = 61) | 100 mg Q2W + TCS (n = 63) | Placebo + TCS (n = 62) | 300 mg Q4W + TCS (n = 61) | 200 mg Q2W + TCS (n = 59) |
| Change in weekly average of daily Peak Pruritus NRS, LS mean ± SE | NA | | | | | |
| Change in BSA, LS mean ± SE | −23.9 (2.3) | −43.2 (2.2) §¶ | −40.6 (2.1) §¶ | −19.8 (2.5) | −38.2 (2.5) §¶ | 38.4 (2.5) §¶ |
| Change in DFI, LS mean ± SE | NA | | | | | |
| Change in PROMIS anxiety, LS mean ± SE | NA | | | | | |
| Change in PROMIS depression, LS mean ± SE | NA | | | | | |
| Mean proportion of TCS-free days (SD) | NA | | | | | |
| Mean weekly use of low-or medium-potency TCS, LS mean ± SE, g | NA | | | | | |

TABLE 6B-continued

Efficacy Results for Other Secondary Endpoints (by Baseline Weight)

| | Baseline weight <30 kg | | | Baseline weight ≥30 kg | | |
|---|---|---|---|---|---|---|
| | Placebo + TCS (n = 61) | 300 mg Q4W + TCS (n = 61) | 100 mg Q2W + TCS (n = 63) | Placebo + TCS (n = 62) | 300 mg Q4W + TCS (n = 61) | 200 mg Q2W + TCS (n = 59) |
| Change in SCORAD sleep component VAS, LS mean ± SE[a] | −2.0 (0.4) | −4.6 (0.3) [§¶] | −4.5 (0.3) [§¶] | −2.1 (0.4) | −3.9 (0.3) [§*] | −4.5 (0.3) [§¶] |
| Change in POEM sleep item, LS mean ± SE[b] | −1.0 (0.2) | −2.2 (0.2) [§¶] | −1.9 (0.2) [§*] | −0.9 (0.2) | −2.0 (0.2) [§¶] | −2.3 (0.2) [§¶] |
| Change in CDLQI sleep item, LS mean ± SE[c] | −0.7 (0.1) | −1.5 (0.1) [§¶] | −1.4 (0.1) [§¶] | −0.6 (0.1) | −1.2 (0.1) [§¶] | −1.3 (0.1) [§¶] |

*$P < 0.001$; †$P < 0.05$; ¶$P < 0.0001$; ‡$P < 0.01$; §nominal P value.
Sleeplessness was assessed by the [a]SCORAD sleep component-a visual analog scale with a maximum score of 10, indicating the worst imaginable sleeplessness;
[b]POEM sleep item ("Over the last week, on how many nights has your sleep been disturbed because of the eczema?");
[c]CDLQI sleep item ("Over the last week, how much has your sleep been affected by your skin problem?").
LS, least squares; NA, not available; SE, standard error.

Figures 1D, 1E, 1F:
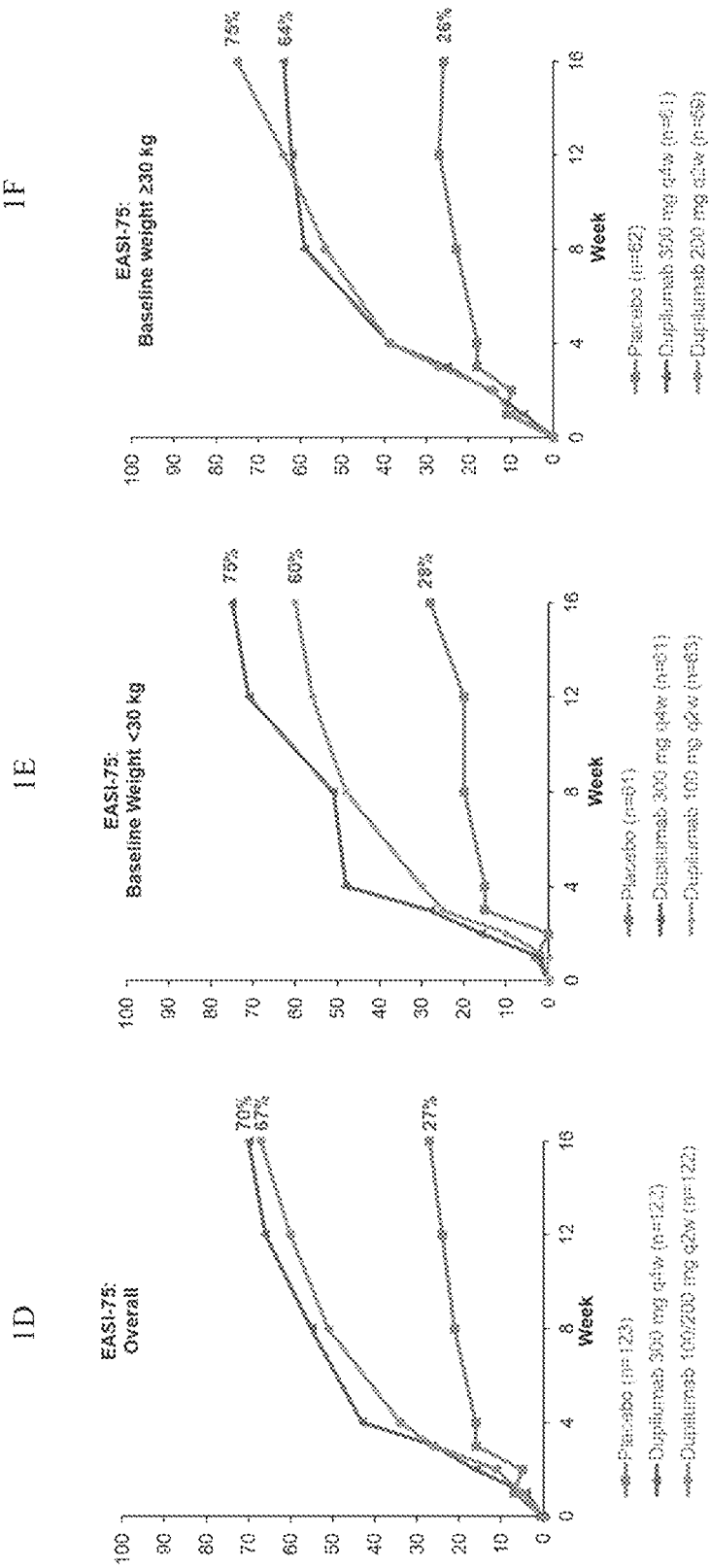
Figure 1G:
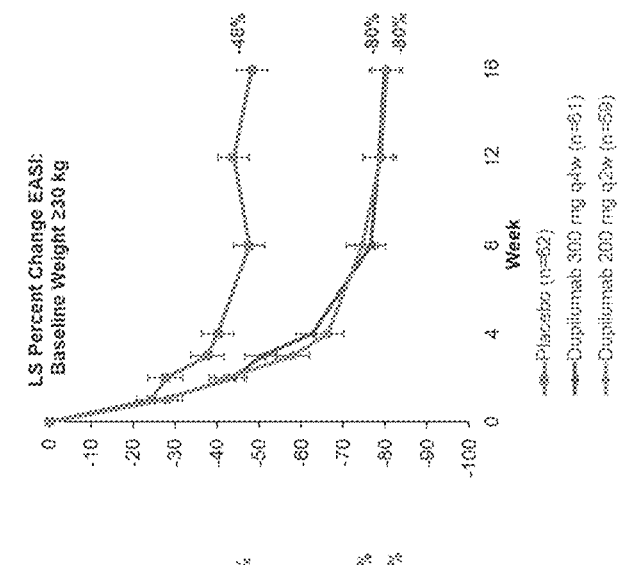
Figures 2A, 2B, 2C:
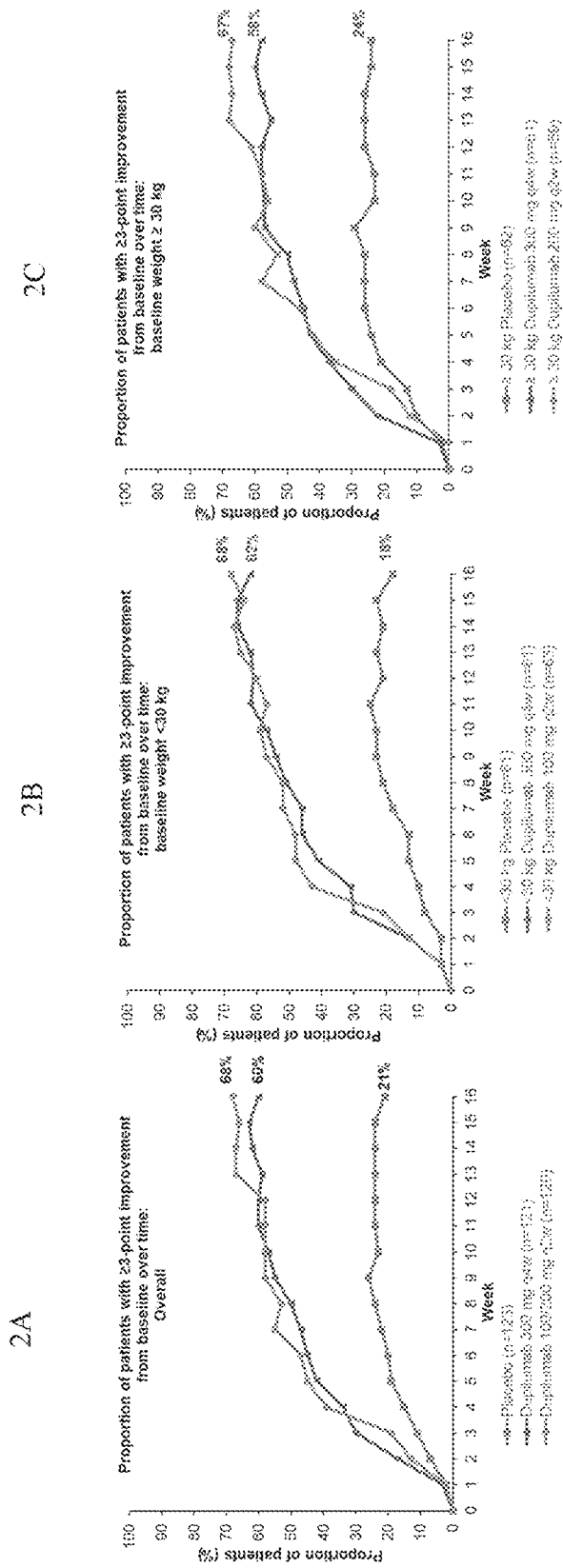
FIGS. 2A-2F. Proportions of patients with 23-improvement (A-C) and 24-point improvement (D-F) in weekly average of Peak Pruritus Numerical Rating Scale over time, in the overall population (A, D), in the baseline weight <30 kg subgroup (B, E), and in the ≥30 kg subgroup (C, F). Q2W=every 2 weeks; Q4W=every 4 weeks.
Figures 2D, 2E, 2F:
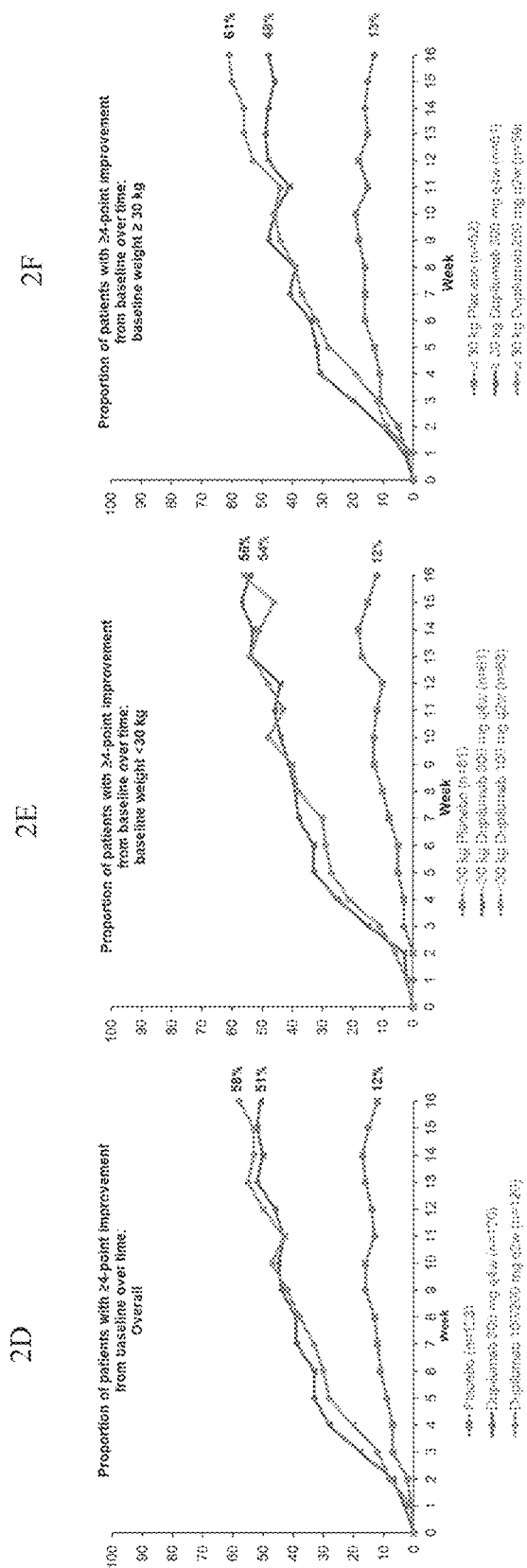

Statistical significance was achieved for the primary endpoint (IGA 0/1) and co-primary endpoint (EASI-75) at week 16 for both dupilumab treatment arms (300 mg Q4W and 100/200 mg Q2W) (IGA (0/1) responder rates: placebo: 11.4; 300 mg Q4W 32.8%; 100/200 mg Q2W: 29.5%; EASI-75 responder rates: placebo: 26.8%; 300 mg Q4W 69.7%; 100/200 mg Q2W: 67.2%). See, Table 5A and FIGS. 1A and 1D. Statistical significance was achieved for key secondary efficacy endpoints for both dupilumab treatment arms (Mean % change in EASI: placebo: −48.6%; 300 mg Q4W: −82.1%; 100/200 mg Q2W: −78.4%; mean % change in pruritus NRS: placebo: −25.9%; 300 mg Q4W: −54.6%; 100/200 mg Q2W: −57.0%). See, Table 5A and FIG. 1G. Statistical significance was also achieved for all remaining endpoints in hierarchy for both dupilumab treatment arms (Table 5A) and additional endpoints (Table 6A); see also FIGS. 2A and 2D.

The efficacy results in this study were comparable to the severe AD subgroup in an adult Phase 3 study with concomitant TCS (CHRONOS): For primary endpoint IGA 0/1, 32.8% of the 300 mg Q4W and 29.5% of the 100/200 mg were responders, as compared to 28.3% of adults in the severe AD subgroup. EASI-75% responder rates were 69.7% for 300 mg Q4W, 67.2% for 100/200 mg Q2W, and 67.9% for adults in the severe AD subgroup. Results were also comparable for the secondary endpoints % change EASI, % change Pruritus NRS, ≥4 point reduction in PNRS, ≥3 point reduction in PNRS, EASI-50, EASI-90, change in POEM, and % change in SCORAD.

Figure 1H:
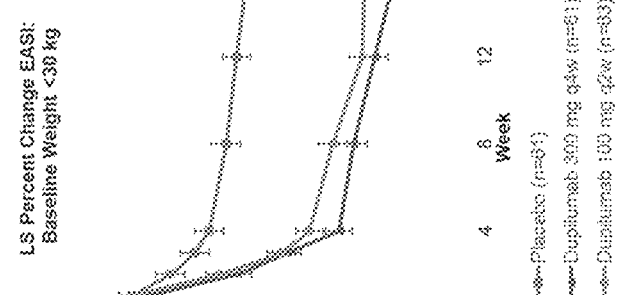

Overall efficacy results by dose and weight group are shown in Tables 5B and 6B and are also summarized in Table 7. For patients in the <30 kg subgroup, a higher percentage of patients in the 300 mg Q4W treatment group met the IGA 0/1 endpoint as compared to the 100 mg Q2W treatment group (29.5% vs 20.6%). A higher percentage of patients in the 300 mg Q4W treatment group also met the EASI-75 co-primary endpoint as compared to the 100 mg q2w treatment group (75.4% vs 60.3%). For several secondary endpoints, results were numerically greater for the 300 mg Q4W treatment group as compared to the 100 mg Q2W treatment group: a higher percentage change in EASI was observed for the 300 mg Q4W treatment group (−84.3% vs −76.7%); more patients achieved EASI-50 in the 300 mg Q4W treatment group (95.1% vs 79.4%); and more patients achieved EASI-90 in the 300 mg Q4W treatment group (45.9% vs 25.4%). See, FIGS. 1B, 1E, and 1H. However, for other secondary endpoints such as percentage change in Pruritis NRS, ≥24 point NRS reduction, 23 point NRS reduction, change in POEM score, and change in CDLQI score, comparable efficacy was shown for the 300 mg Q4W and 100 mg Q2W treatment groups. See, FIGS. 2B and 2E.

Figure 1I:
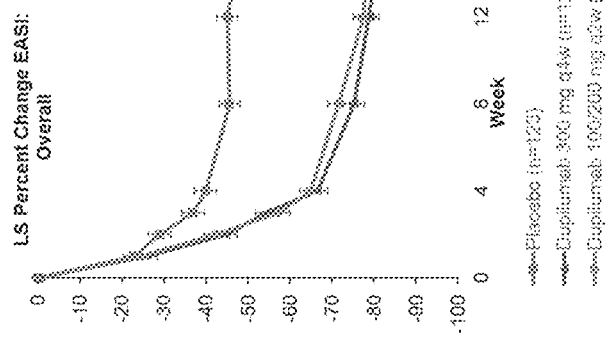

For patients in the ≥30 kg subgroup, results were numerically greater for the 200 mg Q2W treatment group as compared to the 300 mg Q4W treatment group for categorical itch endpoints: 61.4% of patients in the 200 mg Q2W treatment group exhibited a ≥4 point NRS reduction as compared to 47.5% of patients in the 300 mg Q4W treatment group; 66.7% of patients in the 200 mg Q2W treatment group exhibited a ≥3 point NRS reduction as compared to 58.3% of patients in the 300 mg q4w treatment group. See, FIGS. 2C and 2F. For the co-primary endpoint EASI-75, a higher percentage of patients in the 200 mg Q2W treatment group were responders as compared to the 300 mg Q4W treatment group (74.6% vs 63.9%). See, FIG. 1F. Other primary and secondary endpoints were generally comparable between the 300 mg Q4W and 200 mg Q2W treatment groups (Table 7 and FIGS. 1C and 1I).

TABLE 7

Overall Efficacy by Dose and Weight Group

| | | | | | Q2W +TCS | |
|---|---|---|---|---|---|---|
| | Pbo + TCS | | 300 mg Q4W + TCS | | <30 kg | ≥30 kg |
| Endpoint | <30 kg N = 61 | ≥30 kg N = 62 | <30 kg N = 61 | ≥30 kg N = 61 | (100 mg) N = 63 | (200 mg) N = 59 |
| IGA 0/1, n (%) | 8 (13.1%) | 6 (9.7%) | 18 (29.5%) | 22 (36.1%) | 13 (20.6%) | 23 (39.0%) |
| EASI-75, n (%) | 17 (27.9%) | 16 (25.8%) | 46 (75.4%) | 39 (63.9%) | 38 (60.3%) | 44 (74.6%) |

TABLE 7-continued

Overall Efficacy by Dose and Weight Group

| | Pbo + TCS | | 300 mg Q4W + TCS | | Q2W +TCS | |
| --- | --- | --- | --- | --- | --- | --- |
| | <30 kg | ≥30 kg | <30 kg | ≥30 kg | <30 kg (100 mg) | ≥30 kg (200 mg) |
| Endpoint | N = 61 | N = 62 | N = 61 | N = 61 | N = 63 | N = 59 |
| % change EASI, LSmean (SE) | −49.1 (3.30) | −48.3 (3.63) | −84.3 (3.08) | −79.9 (3.57) | −76.7 (3.04) | −80.4 (3.61) |
| % change Pruritus NRS, LSmean (SE) | −27.0 (4.24) | −25.0 (3.95) | −55.1 (3.94) | −54.3 (4.19) | −56.1 (3.86) | −58.2 (4.01) |
| ≥4 point NRS reduction, n/N1[1] (%) | 7/60 (11.7%) | 8/62 (12.9%) | 33/61 (54.1%) | 28/59 (47.5%) | 35/63 (55.6%) | 35/57 (61.4%) |
| ≥3 point NRS reduction, n/N1[1] (%) | 11/61 (18.0%) | 15/62 (24.2%) | 38/61 (62.3%) | 35/60 (58.3%) | 43/63 (68.3%) | 38/57 (66.7%) |
| EASI-50, n (%) | 26 (42.6%) | 27 (43.5%) | 58 (95.1%) | 53 (86.9%) | 50 (79.4%) | 51 (86.4%) |
| EASI-90, n (%) | 4 (6.6%) | 5 (8.1%) | 28 (45.9%) | 23 (37.7%) | 16 (25.4%) | 21 (35.6%) |
| Change POEM, LSmean (SE) | −5.9 (1.04) | −4.7 (0.91) | −14.0 (0.95) | −13.2 (0.89) | −13.3 (0.94) | −13.6 (0.90) |
| Change CDLQI, LSmean (SE) | −7.2 (0.76) | −5.6 (0.66) | −11.5 (0.69) | −9.7 (0.63) | −11.6 (0.67) | −9.8 (0.63) |
| % change SCORAD, LSmean (SE) | −28.9 (3.05) | −30.7 (3.28) | −65.3 (2.87) | −59.3 (3.12) | −58.1 (2.83) | −62.7 (3.14) |

[1] N1 is the number of patients with baseline pruritus NRS ≥4 (3).

For the primary endpoint IGA 0/1 at week 16, comparable efficacy was observed between the 300 mg Q4W and the 100/200 mg Q2W treatment groups. At week 16, 32.8% of patients in the 300 mg Q4W treatment group and 29.5% of patients in the 100/200 mg Q2W treatment group achieved an IGA of 0 or 1, as compared to only 11.4% of patients in the placebo+TCS group. The increase in the proportion of patients achieving an IGA of 0 or 1 was apparent as early as week 2 of treatment for the 300 mg Q4W treatment group (5.7% of patients as responders vs 1.6% of patient for placebo group), and by week 8, 24.6% of patients in the 300 mg Q4W treatment group had achieved an IGA of 0 or 1 (vs 7.3% for placebo). For the 100/200 mg Q2W treatment group, at week 66.6% of patients had achieved an IGA of 0 or 1 (vs 3.3% for placebo), and by week 8, 23% of patients in the 100/200 mg Q2W treatment group had achieved an IGA of 0 or 1 (vs 7.3% for placebo).

For the co-primary endpoint EASI-75 at week 16, comparable efficacy was observed between the 300 mg Q4W and the 100/200 mg Q2W treatment groups. At week 16, 69.7% of patients in the 300 mg Q4W treatment group and 67.2% of patients in the 100/200 mg Q2W treatment group achieved EASI-75, as compared to only 26.8% of patients in the placebo+TCS group. Comparable efficacy was observed for the Q4W and Q2W treatment groups for each of the EASI-50/75/90 response thresholds (Table 5), although a slight decrease in the proportion of responders was observed from weeks 12-16 for the Q2W treatment group (for EASI-50, a decrease from 86.1% at week 12 to 82.8% at week 16; for EASI-90, a decrease from 31.1% at week 12 to 30.3% at week 16). Comparable efficacy in the EASI percent change from baseline to week 16 was observed between the dupilumab treatment groups (−82.1% for the 300 mg Q4W treatment group and −78.4% for the 100/200 mg Q2W treatment group, vs −48.6% for placebo+TCS group). For both dupilumab treatment arms, the efficacy in EASI-75 response rate and EASI percent change was comparable to the efficacy observed for dupilumab with concomitant TCS for adults in the severe AD subgroup.

Pruritis NRS response rates were numerically greater for 100/200 mg Q2W on categorical itch endpoints. For the endpoint NRS ≥3 response at week 16, 67.5% of patients in the 100/200 mg Q2W treatment group were responders, while 60.3% of patients in the 300 mg Q4W treatment group were responders. Both treatment groups were significantly greater than placebo (21.1%). For the endpoint NRS ≥4 response at week 16, 58.3% of patients in the 100/200 mg Q2W treatment group were responders, while 50.8% of patients in the 300 mg Q4W treatment group were responders. Both treatment groups were significantly greater than placebo (12.3%). An effect on itch was apparent at week 2 in both dupilumab treatment arms: at week 2, 17.4% of patients in the 300 mg Q4W treatment group and 12.5% of patients in the 100/200 mg Q2W treatment group achieved NRS ≥3, in contrast to only 6.5% of patients in the placebo group. Both dupilumab treatment groups exhibited comparable efficacy in pruritus NRS percent change from baseline (−54.6% for the 300 mg Q4W treatment group and −57% for the 100/200 mg Q2W treatment group, vs −25.9% for placebo).

In children with moderate-to-severe AD, skin lesions often involve a large body surface area (BSA), resulting in pruritus and sleep deprivation that greatly impact quality of life for young patients and that of their caregivers. Scoring AD (SCORAD) is an AD-specific measurement tool recommended by European AD guidelines that evaluates the investigator-assessed affected BSA and severity of signs, as well as patient-reported symptoms of pruritus and sleep loss. The effect of dupilumab in combination with standardized topical treatment on SCORAD and its components was assessed using Least squares (LS) mean (standard error [SE]) scores for total SCORAD (score range 0-103 s) 7.

(components, namely: BSA affected by AD (0-100%); objective SCORAD (o-SCORAD, 0-83); SCORAD prutus Visual Analog Scale (VAS, 0-10); and sleep loss VAS (0-10). Multiple imputation method was used with censoring after rescue treatment use.

Figure 3:
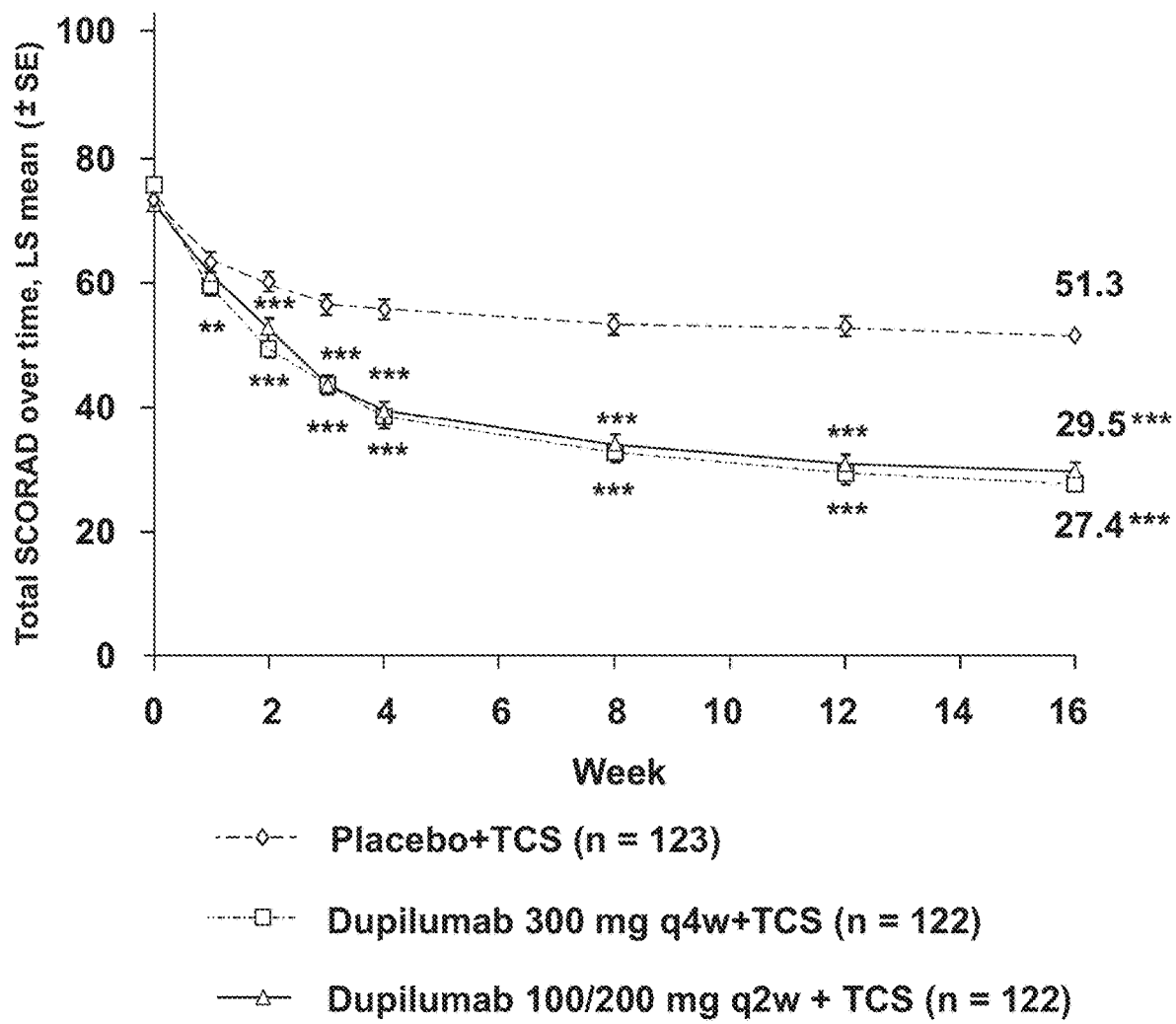
FIG. 3 graphically depicts the total SCORAD over time for subjects receiving placebo+topical corticosteroids (TCS), dupilumab 300 mg Q4W+TCS, or dupilumab 100/200 mg Q2W+TCS. P<0.01; *P<0.001 vs placebo+TCS.

Baseline demographics and disease characteristics are presented in Table 8, below. Treatment with dupilumab+TCS resulted in a significant improvement in total SCORAD score by Week 1 with Q4W+TCS and Week with Q2W+TCS, and further improvements were seen through end of treatment at Week 16 (FIG. 3, Table 8). By Week 2, significant reductions were seen in affected BSA with both dupilumab treatment regimens, with further reductions observed up to Week 16. o-SCORAD significantly improved as early as Week 1 with dupilumab Q4W+TCS and by Week 2 with dupilumab Q2W+TCS, both vs placebo+TCS, and these results continued to improve through Week 16. By Week 2, symptoms of prutus and sleep loss significantly improved with both dupilumab treatment regimens vs placebo+TCS as measured by SCORAD pruritus VAS and sleep loss VAS, and both continued to improve through end of treatment at Week 16 (Table 8).

subjects receiving placebo and TCS, the week 16 score of 51.3 amounted to about 70% of the initial (baseline) total SCORAD score of 72.9. In other words, the subjects receiving placebo and TCS only exhibited about a 30% decrease (100%-70%) in total SCORAD score from baseline. In comparison, for total SCORAD score of subjects receiving dupilumab 300 mg Q4W and TCS, the week 16 score of 27.4 amounted to about 36% of the initial (baseline) total SCORAD score of 75.6. In other words, the subjects receiving dupilumab 300 mg Q4W and TCS exhibited about a 64% decrease (100%-36%) in total SCORAD score from baseline. And for total SCORAD score of subjects receiving dupilumab 100/200 mg Q2W and TCS, the week 16 score of 29.5 amounted to about 40% of the initial (baseline) total SCORAD score of 72.3. In other words, the subjects receiving dupilumab 100/200 mg Q2W and TCS exhibited about a 60% decrease (100%-40%) in total SCORAD score from baseline.

Comparable rates of rescue treatment were observed between the 300 mg Q4W and the 100/200 mg Q2W treatment groups; the rate of rescue treatment for the dupi-

TABLE 8

Baseline characteristics and efficacy outcomes at Week 1, Week 2, and Week 16 for total SCORAD and SCORAD components

| LS mean (± SE) score | Score range | Placebo + TCS (n = 123) | Dupilumab 300 mg Q4W+ TCS (n = 122) | Dupilumab 100/200 mg Q2W + TCS (n = 122) |
|---|---|---|---|---|
| Total SCORAD, baseline | 0-103 | 72.9 (1.1) | 75.6 (1.1) | 72.3 (1.0) |
| Week 1 | | 63.4 (1.2) | 58.9 (1.2)** | 61.2 (1.2) |
| Week 2 | | 60.0 (1.3) | 49.4 (1.3)*** | 52.5 (1.3)*** |
| Week 16 | | 51.3 (1.6) | 27.4 (1.5)*** | 29.5 (1.5)*** |
| BSA affected by AD (%), baseline | 0-100 | 58.9 (2.0) | 54.7 (2.0) | 56.5 (1.9) |
| Week 1 | | 48.0 (1.4) | 46.9 (1.4) | 47.8 (1.4) |
| Week 2 | | 46.7 (1.6) | 38.9 (1.6)*** | 38.6 (1.6)*** |
| Week 16 | | 36.0 (1.8) | 16.5 (1.7)*** | 18.5 (1.7)*** |
| o-SCORAD, baseline | 0-83 | 59.6 (0.9) | 61.1 (0.9) | 58.7 (0.8) |
| Week 1 | | 51.7 (1.0) | 48.3 (1.0)* | 50.3 (1.0) |
| Week 2 | | 48.4 (1.1) | 40.3 (1.1)*** | 43.0 (1.1)*** |
| Week 16 | | 41.7 (1.4) | 23.0 (1.3)*** | 25.1 (1.3)*** |
| SCORAD pruritus VAS, baseline | 0-10 | 7.4 (0.2) | 7.8 (0.2) | 7.6 (0.2) |
| Week 1 | | 6.5 (0.2) | 6.0 (0.2) | 6.0 (0.2) |
| Week 2 | | 6.3 (0.2) | 5.1 (0.2)*** | 5.3 (0.2)** |
| Week 16 | | 5.1 (0.2) | 2.6 (0.2)*** | 2.5 (0.2)*** |
| SCORAD sleep loss VAS, baseline | 0-10 | 6.0 (0.3) | 6.8 (0.3) | 6.0 (0.3) |
| Week 1 | | 5.1 (0.2) | 4.8 (0.2) | 4.9 (0.2) |
| Week 2 | | 5.2 (0.3) | 4.1 (0.3)** | 4.1 (0.3)** |
| Week 16 | | 4.2 (0.3) | 2.0 (0.3)*** | 1.8 (0.3)*** |

*P < 0.05;
**P < 0.01;
***P < 0.001 vs placebo + TCS.

Thus, in children aged ≥6 to <12 with severe AD, treatment with dupilumab and concomitant medium-potency TCS resulted in rapid significant reduction in BSA affected by AD, and improvements in AD signs, pruritus, and sleep loss as assessed by total SCORAD and SCORAD components.

Based on the data in Table 8 at week 16, percentage improvements in total SCORAD and SCORAD component parameters were calculated. For total SCORAD score of lumab treated groups was significantly lower than the placebo group (for placebo, 19.5% of patients required rescue treatment by week 16, while 2.5% of patients in the 300 mg Q4W and 4.1% of patients in the 100/200 Q2W treatment groups required rescue treatment). The rate of rescue for these pediatric dupilumab-treated patients was overall lower than the rate of rescue in adolescents and adults with severe AD (Table 9).

TABLE 9

Rescue Treatment

| | 6-≤12 years (w. TCS) | | 12-≤18 years (w/o. TCS) | | | Adults Wk 16 (w. TCS) IGA 4 Subgroup | |
|---|---|---|---|---|---|---|---|
| | 300 mg | 100/200 mg | | IGA4 Subgroup | | | 300 mg |
| | Pbo + TCS 123 | Q4W + TCS 122 | Q2W + TCS 122 | Pbo 46 | 300 mg Q4W 46 | 100/200 mg Q2W 43 | Pbo 147 | Q2W + TCS 53 |
| % pts rescued by Wk 16 | 19.5% | 2.5% | 4.1% | 67.4% | 32.6% | 18.6% | 48.3% | 9.4% |

Safety

No new or unexpected side effects were observed in the trial compared to those seen in trials of adult or adolescent patients. See Table 10, below. For the 16-week treatment period, the overall rate of adverse events was lower for the dupilumab groups as compared to placebo (65% for dupilumab 300 mg Q4W, 67.2% for dupilumab 100/200 mg Q2W, and 73.3% for placebo). All serious adverse events were unrelated to the study drug. Treatment discontinuations due to AEs were uncommon (placebo+TCS, n=2; 100/200 mg Q2W+TCS, n=2). No deaths or treatment-related events of hypersensitivity or anaphylaxis occurred during the study. No new safety signals were observed. Adverse events that were observed at a higher rate with dupilumab included conjunctivitis (narrow CMQ) (6.7% for narrow conjunctivitis 6.7% for dupilumab every four weeks and vs 14.8% for dupilumab every two weeks, compared to 4.2% for placebo); conjunctivitis (broad CMQ) (8.3% for dupilumab every four weeks and 18.9% for dupilumab every two weeks, as compared to 7.5% for placebo); and injection site reaction (10% for dupilumab every four weeks and 10.7% for dupilumab every two weeks, compared to 5.8% for placebo). Most conjunctivitis events recovered or were recovering with standard ophthalmic treatments during study drug treatment. The highest incidence of conjunctivitis (24%) occurred in the treatment group with the lowest exposure (100 mg Q2W+TCS), consistent with previous analyses suggesting that conjunctivitis associated with dupilumab treatment may result from relative undertreatment within the eye compartment (Akinlade et al., Br J Dermatol, 2019, 181(3):459-473). A lower incidence of conjunctivitis was observed in the Q4W treatment group as compared to the Q2W treatment group. As seen in trials of adult and adolescent patients, and consistent with long-term experience with dupilumab treatment, adjudicated skin infections and herpes viral infections were observed at a lower rate in the dupilumab treatment groups as compared to the placebo group (adjudicated skin infection: 13.3% for placebo, 5.8% for dupilumab every four weeks, and 8.2% for dupilumab every two weeks; Herpes viral infections: 5% for placebo, 1.7% for dupilumab every four weeks, and 3.3% for dupilumab every two weeks).

In this patient population with a high burden of comorbid type 2 inflammatory diseases, and as would be expected given the demonstrated efficacy of dupilumab for these conditions, incidence of type 2 inflammatory AEs was lower with higher dupilumab exposure. Among patients <30 kg, AEs of AD exacerbation, asthma, and allergic rhinitis were less common in the 300 mg Q4W+TCS group than 100 mg Q2W+TCS (Table 10). A similar trend was noted in patients ≥30 kg, with lower incidence for 200 mg Q2W+TCS than 300 mg Q4W+TCS.

The long-term safety of treatment with dupilumab and TCS in pediatric subjects from the 16-week clinical trial described above was assessed in an open-label extension study. Among patients who entered this study, 110 (30%) had moderate and 72 (20%) had severe atopic dermatitis at the time of enrollment in the open-label extension study. The safety profile of dupilumab+TCS in subjects followed through Week 52 of the open-label extension was similar to the safety profile observed at Week 16 in the 16-week trial. The long-term safety profile of dupilumab+TCS observed in pediatric patients was consistent with that seen in adults and adolescents with atopic dermatitis.

TABLE 10

Safety Assessment

| | Overall | | | Baseline weight <30 kg | | | Baseline weight ≥30 kg | | |
|---|---|---|---|---|---|---|---|---|---|
| | Placebo (n = 120) | 300 mg Q4W + TCS (n = 120) | 100/200 mg Q2W + TCS (n = 122) | Placebo + TCS (n = 60) | 300 mg Q4W + TCS (n = 60) | 100 mg Q2W + TCS (n = 63) | Placebo + TCS (n = 60) | 300 mg Q4W + TCS (n = 60) | 200 mg Q2W + TCS (n = 59) |
| Patients with ≥1 TEAE, n (%) | 88 (73.3) | 78 (65.0) | 82 (67.2) | 43 (71.7) | 39 (65.0) | 46 (73.0) | 45 (75.0) | 39 (65.0) | 36 (61.0) |
| Patients with ≥1 serious TEAE, n (%)* | 2 (1.7) | 2 (1.7) | 0 | 0 | 2 (3.3) | 0 | 2 (3.3) | 0 | 0 |
| Patients with ≥1 TEAE leading to permanent treatment discontinuation** | 2 (1.7) | 0 | 2 (1.6) | 2 (3.3) | 0 | 1 (1.6) | 0 | 0 | 1 (1.7) |
| Deaths | 0 | 0 | 0 | 0 | 0 | 0 | 0 | 0 | 0 |
| TEAEs (PT) reported in ≥5% of patients, n (%) | | | | | | | | | |
| Dermatitis atopic, exacerbation | 17 (14.2) | 8 (6.7) | 10 (8.2) | 7 (11.7) | 4 (6.7) | 8 (12.7) | 10 (16.7) | 4 (6.7) | 2 (3.4) |
| Asthma | 12 (10.0) | 2 (1.7) | 4 (3.3) | 7 (11.7) | 0 | 4 (6.3) | 5 (8.3) | 2 (3.3) | 0 |

TABLE 10-continued

Safety Assessment

| | Overall | | | Baseline weight <30 kg | | | Baseline weight ≥30 kg | | |
|---|---|---|---|---|---|---|---|---|---|
| | Placebo (n = 120) | 300 mg Q4W + TCS (n = 120) | 100/200 mg Q2W + TCS (n = 122) | Placebo + TCS (n = 60) | 300 mg Q4W + TCS (n = 60) | 100 mg Q2W + TCS (n = 63) | Placebo + TCS (n = 60) | 300 mg Q4W + TCS (n = 60) | 200 mg Q2W + TCS (n = 59) |
| Rhinitis allergic | 5 (4.2) | 3 (2.5) | 4 (3.3) | 2 (3.3) | 1 (1.7) | 3 (4.8) | 3 (5.0) | 2 (3.3) | 1 (1.7) |
| Nasopharyngitis | 8 (6.7) | 15 (12.5) | 8 (6.6) | 2 (3.3) | 6 (10.0) | 6 (9.5) | 6 (10.0) | 9 (15.0) | 2 (3.4) |
| Upper respiratory tract infection | 12 (10.0) | 13 (10.8) | 10 (8.2) | 5 (8.3) | 9 (15.0) | 5 (7.9) | 7 (11.7) | 4 (6.7) | 5 (8.5) |
| Viral upper respiratory tract infection | 6 (5.0) | 2 (1.7) | 1 (0.8) | 5 (8.3) | 1 (1.7) | 1 (1.6) | 1 (1.7) | 1 (1.7) | 0 |
| Vomiting | 8 (6.7) | 6 (5.0) | 6 (4.9) | 4 (6.7) | 3 (5.0) | 2 (3.2) | 4 (6.7) | 3 (5.0) | 4 (6.8) |
| Cough | 9 (7.5) | 3 (2.5) | 5 (4.1) | 5 (8.3) | 0 | 2 (3.2) | 4 (6.7) | 3 (5.0) | 3 (5.1) |
| Headache | 10 (8.3) | 6 (5.0) | 7 (5.7) | 3 (5.0) | 1 (1.7) | 1 (1.6) | 7 (11.7) | 5 (8.3) | 6 (10.2) |
| Other adverse events, n (%) | | | | | | | | | |
| Infections and infestations (SOC) | 61 (50.8) | 52 (43.3) | 49 (40.2) | 30 (50) | 26 (43.3) | 28 (44.4) | 31 (51.7) | 26 (43.3) | 21 (35.6) |
| Conjunctivitis cluster[a] | 5 (4.2) | 8 (6.7) | 18 (14.8) | 2 (3.3) | 4 (6.7) | 13 (20.6) | 3 (5.0) | 4 (6.7) | 5 (8.5) |
| Keratitis cluster[b] | 0 | 0 | 1 (0.8) | 0 | 0 | 1 (1.6) | 0 | 0 | 0 |
| Skin infection (adjudicated)[c] | 16 (13.3) | 7 (5.8) | 10 (8.2) | 8 (13.3) | 4 (6.7) | 5 (7.9) | 8 (13.3) | 3 (5.0) | 5 (8.5) |
| Injection-site reactions (HLT) | 7 (5.8) | 12 (10.0) | 13 (10.7) | 4 (6.7) | 6 (10.0) | 5 (7.9) | 3 (5.0) | 6 (10.0) | 8 (13.6) |
| Herpes viral infections (HLT) | 6 (5.0) | 2 (1.7) | 4 (3.3) | 3 (5.0) | 0 | 3 (4.8) | 3 (5.0) | 2 (3.3) | 1 (1.7) |

[a]Conjunctivitis cluster (narrow conjunctivitis) includes PTs (MedDRA Preferred Terms) conjunctivitis, conjunctivitis allergic, conjunctivitis bacterial, conjunctivitis viral, and atopic keratoconjunctivitis.
[b]Keratitis cluster includes PTs keratitis, ulcerative keratitis, allergic keratitis, atopic keratoconjunctivitis, and ophthalmic herpes simplex.
[c]Skin infections were adjudicated on a case-by-case basis and included bacterial, viral, and fungal infections.

Clinical Pharmacology and Pharmacokinetics

The 300 mg Q4W and 200 mg Q2W regimens achieved similar steady state (week 16) trough concentrations (80 mg/L) as compared to the 100 mg Q2W regimen, which achieved a lower trough concentration (50 mg/L). Trough concentrations of functional dupilumab at week 16 by body weight category and treatment group showed lower concentrations in the 100 mg Q2W <30 kg group and 300 mg Q4W ≥30 kg groups. Consistent with the efficacy analysis, 300 mg Q4W+TCS regimen maintained substantially higher trough blood levels than did 100 mg Q2W+TCS in the <30 kg stratum (Week 16 mean $C_{trough}$ 99 mg/L vs. 63 mg/L). In the ≥30 kg group, the 200 mg Q2W+TCS regimen maintained consistently higher trough blood levels than did 300 mg Q4W+TCS (86 mg/L vs. 54 mg/L). Exposure/response relationships over time, assessed by quartile analyses of exposure for percent change from baseline in EASI and percentage of patients achieving IGA 0/1 and logistic regression for binary endpoints (EASI-50, EASI-75, EASI-90, and IGA 0/1), indicated a trend for increasing drug effect with increasing $C_{trough}$ (data not shown).

CONCLUSION

In pediatric patients aged 6-11 with severe AD inadequately controlled with topical medications, treatment with dupilumab for 16 weeks resulted in clinically meaningful, statistically significant, and rapid improvement across AD-associated parameters, including itch, anxiety, and depression, and in sleep and QoL. As most efficacy measures were continuing to show improvement at the Week 16 time point, it is possible that further benefit would accrue with longer treatment.

The monthly (300 mg Q4W) and weight-based (100 mg Q2W for patients <30 kg, 200 mg Q2W for patients ≥30 kg) dosing regimens were comparable for most endpoints. For the sub-group of patients having a body weight <30 kg, for some endpoints (IGA 0/1 at the end of 16 weeks; EASI-50/ 75/90 at the end of 16 weeks; percentage change in EASI) the Q4W regimen was numerically superior to the Q2W regimen. However, for certain other endpoints (Pruritis NRS, 24 point NRS reduction, 23 point NRS reduction, change in POEM score, and change in CDLQI score) the Q4W and Q2W regimens were comparable in efficacy. For the sub-group of patients having a body weight ≥30 kg, for some endpoints (≥4 point NRS reduction, 23 point NRS reduction, and EASI-75) the Q2W regimen was numerically superior to the Q4W regimen, although the Q2W and Q4W regimens exhibited comparable efficacy in other primary and secondary endpoints.

No new safety signals were observed. As with previous studies of dupilumab in AD, only injection-site reactions and conjunctivitis were notably increased for dupilumab vs placebo; most cases were mild-to-moderate and resolved during the course of the trial. Overall incidence of TEAEs was lower with dupilumab treatment. This observation seems to be related to the effect of dupilumab on comorbid type 2 inflammatory conditions as well as on skin infections. Notably, this pediatric study population with severe AD suffers from a very high burden of comorbid type 2 or allergic conditions: almost half of these children suffer from asthma; about 60% have allergic rhinitis; and about 65% report food allergies. In addition, children with severe AD are at markedly increased risk for skin infections. Consistent with the concept that patients suffering from severe AD have a systemic perturbation in their immune axis—resulting from Th-2 polarization—that can be addressed by dupilumab, dupilumab treatment not only improved all measures of AD in these patients, but resulted in a decrease in type 2 AEs. Additionally, as infections in these patients result from a breakdown in skin integrity, and as dupilumab treatment can restore skin integrity, dupilumab treatment was associated with lower rates of skin and herpesviral infections. Dupilumab-associated decreases in type 2 comorbidities and infections were correlated with pharmacokinetic exposure. The benefit of dupilumab with regard to infections runs counter to the experience with most other immunomodulatory therapies—e.g., Janus kinase inhibitors, tumor necrosis factor inhibitors, interleukin-23 inhibitors, corticosteroids, cyclosporins, FK506 inhibitors, etc.—that tend to be profoundly immunosuppressive. There is an obvious benefit in this pediatric population for AD treatment that can also address associated comorbid atopic conditions while avoiding immunosuppression. In summary, this study demonstrates the efficacy and safety of dupilumab administered concomitantly with TCS in pediatric patients ≥6 years to <12 years of age with severe AD.

Example 2: Pharmacokinetic Analysis of Dupilumab in Pediatric and Adolescent Patients with Uncontrolled Moderate-to-Severe Atopic Dermatitis In order to characterize the pharmacokinetic profile of dupilumab in children (aged ≥6 to <12 years) and adolescents (aged ≥12 to <18 years) with moderate-to-severe AD, 37 children and 40 adolescents enrolled in the Phase 2a study NCT02407756, incorporated herein in its entirety, and 33 children and 36 adolescents enrolled in the Phase 3 OLE study NCT02612454, incorporated herein in its entirety, were followed. The patients selected for enrollment in the Phase 2a and Phase 3 OLE studies included pediatric patients (aged ≥6 to <18 years) with AD that was inadequately controlled with topical medications or for whom topical therapies were inadvisable. Eligible patients had AD for >1 year before screening, based on American Academy of Dermatology criteria; one baseline IGA with a score of 3 or 4, and ≥10% BSA affected by AD.

The Phase 2a study consisted of a screening period of up to 35 days, a baseline visit, and 2 treatment phases: Part A, in which patients received a single dose of dupilumab (2 mg/kg or 4 mg/kg) followed by an 8-week sampling period for systemic drug concentration; and Part B, in which patients received the same dose weekly for 4 weeks followed by an 8-week safety follow-up period. In the Phase 2a study, the primary outcome was the characterization of the pharmacokinetics of dupilumab.

The Phase 3 OLE study enrolled pediatric patients who participated in previous dupilumab AD trials (the presently described Phase 2a study and other studies). Patients enrolled into the OLE study continued receiving 2 mg/kg or 4 mg/kg dupilumab weekly; the study consisted of a screening period (Day −28 to Day −1), a treatment period that lasts until regulatory approval of the product for the age group of the patients in that geographic region, and a 12-week follow-up period. Data up to 52 weeks from the baseline visit of the OLE study are reported herein.

Outcomes

The primary endpoint of the Phase 2a study was concentration of functional dupilumab in serum over time and other PK parameters; main secondary outcomes included incidence of treatment-emergent adverse events (TEAEs) and percentage changes from baseline in Eczema Area and Severity Index (EASI), Scoring Atopic Dermatitis (SCORAD) and Peak Pruritus Numerical Rating Scale (NRS). The Phase 3 OLE primary endpoints were incidence and rate (events/patient-year [PY]) of TEAEs. Main secondary endpoints included incidence and rate (events/PY) of serious TEAEs and of TEAEs of special interest; proportion of patients with an IGA score 0/1; proportion of patients with ≥75% reduction in EASI (EASI 75) from baseline of parent study; percentage change from baseline of parent study in EASI score; percentage change from baseline of parent study in SCORAD score and change from OLE baseline in Children's Dermatology Life Quality Index (CDQLI).

Pharmacokinetics

PK samples were collected in a semi-dense manner in Part A of the Phase 2a study and at sparse time points in Part B of the Phase 2a and the OLE studies. To limit blood draws in this pediatric population, patients were randomized to a sampling schedule including a subset of potential time points. The mean concentration-time profiles were generated from pooling of all collected samples and used to determine the time to maximum mean concentration ($t_{max}$) and area under the concentration-time curve from time zero to the time of last measurable concentration in Part A ($AUC_{last}$). Maximum dupilumab concentration in serum ($C_{max}$) were calculated for patients with PK samples collected at the $t_{max}$ timepoint. In the OLE, steady-state $C_{tough}$ samples were evaluated over weeks 24-48. Serum samples for dupilumab were analyzed using a validated Enzyme Linked Immunosorbent Assay, with lower limit of quantitation 0.078 mg/L. The PK analysis set included patients with 21 non-missing functional dupilumab result following the first dose of the study drug.

Statistical Analysis

No formal sample size or power calculations were performed. PK, safety and efficacy variables were summarized descriptively; no inferential statistical tests were prespecified in the statistical analysis plan to allow comparison between the treatment arms. Any differences observed in the descriptive summary of the PK, safety and efficacy variables were based on numerical comparisons. The safety and efficacy analysis sets for all statistical analyses for both studies included all patients who received any study drug. Data after rescue treatment use during Part B of the Phase 2a study were set to missing. For continuous endpoints, missing values during the 4-week repeat-dose treatment period of Part B up to end-of-treatment visit were imputed by the last-observation-carried-forward method. After the end of treatment in Part B, no missing data were imputed. For categorical variables, patients with missing values were considered as non-responders. Patients withdrawn from the study were counted as non-responders after withdrawal. Patients who received rescue treatment during Part B were considered non-responders from time of rescue use. For the Phase 3 OLE, an all-observed method was employed, regardless of rescue treatment use or if data were collected after withdrawal from treatment (no missing values imputed). Statistical Analysis Software (SAS) version 9.2 (SAS Institute, Inc) was used for all analyses.

Results—Adolescents (aged ≥12 to <18 years)

Figure 4A:
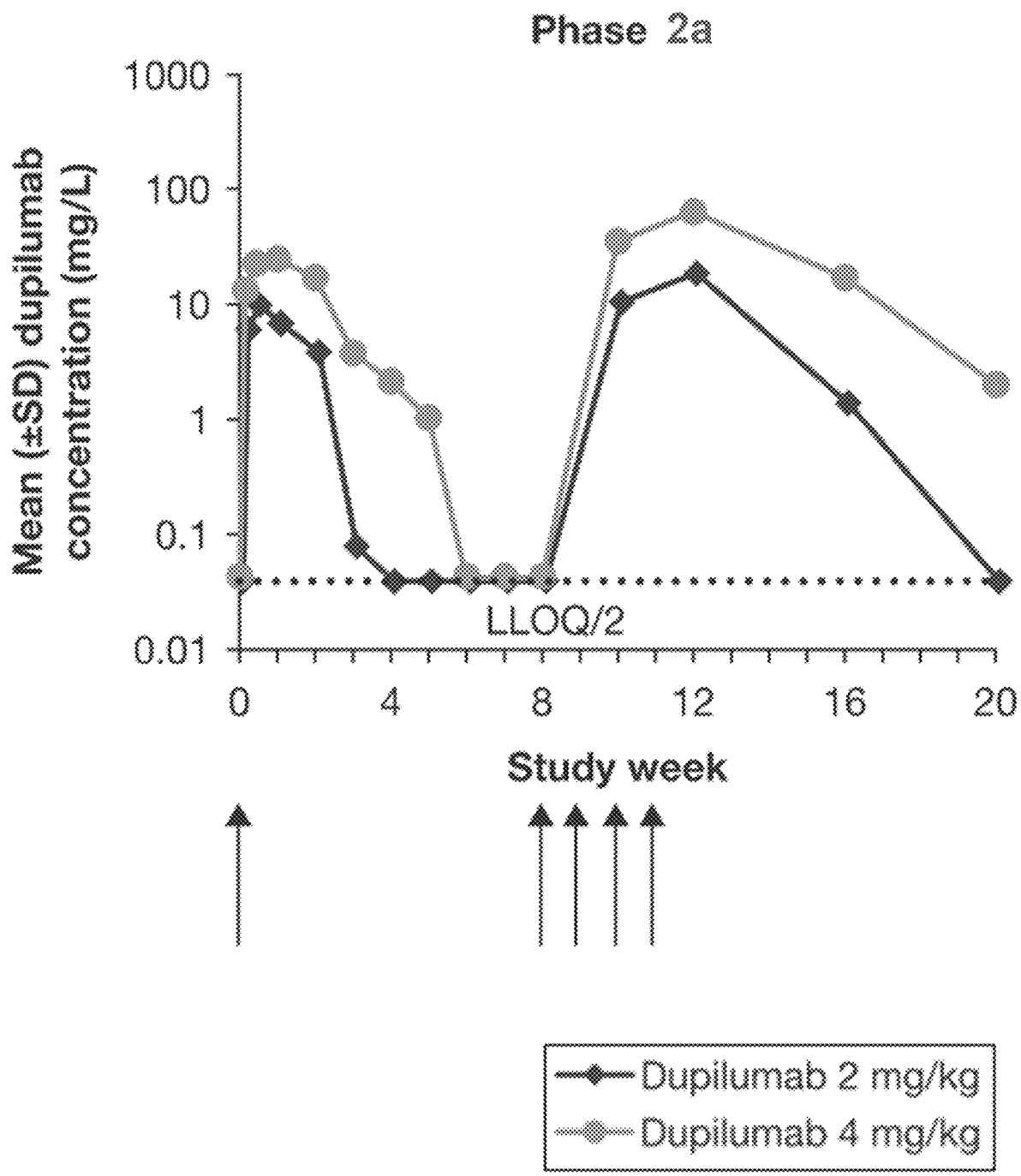
FIGS. 4A and 4B graphically depict the mean log-scaled concentrations of dupilumab in serum over nominal time.
Figure 4B:
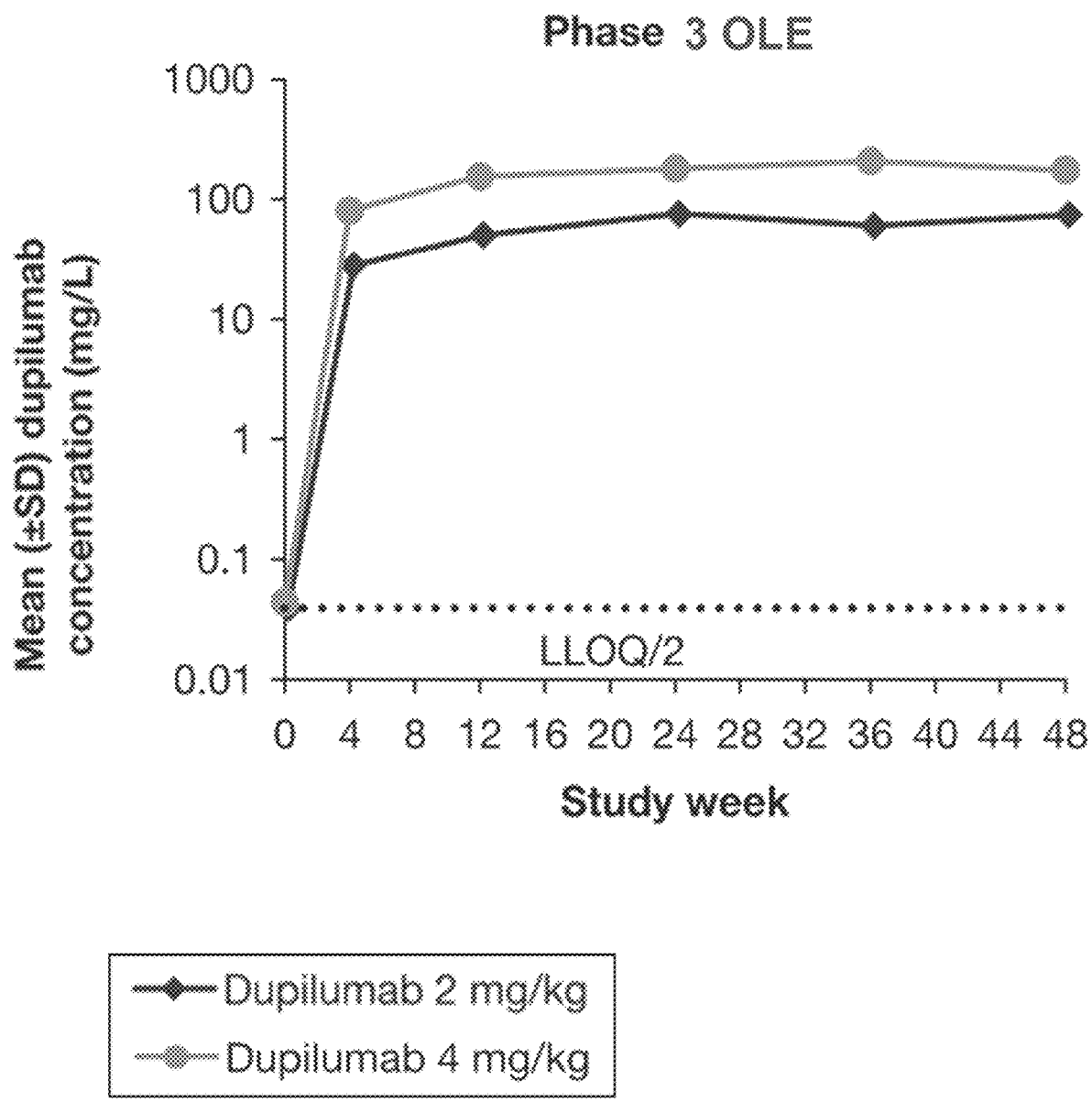

In adolescents with moderate-to-severe AD, the dupilumab pharmacokinetic profile was similar to that observed in adults. Dupilumab showed non-linear, target-mediated pharmacokinetics. After a single dose, $C_{max}$ (±SD) was 10 (±2) mg/L and 23 (9) mg/L for the 2 mg/kg and 4 mg/kg dose groups, respectively; $t_{max}$ was 4-8 days (FIG. 4A). In the OLE, dupilumab concentrations increased in a slightly greater-than-dose-proportional manner from baseline to Week 48 between the 2 mg/kg and 4 mg/kg regimens, achieving mean trough dupilumab concentrations (SD) in serum of 74 (±19) mg/L and 161 (60) mg/L, respectively (FIG. 4B).

Results—Children (Aged ≥6 to <12 Years)

Thirty-eight children (aged ≥6-<12 years) were enrolled in the Phase 2 study. One patient (3%) in the 4 mg/kg dose group was withdrawn from the study during Part A (withdrawal of consent because of fear of study injections). Thirty-seven children (97%) completed Part A and Part B. All 37 patients continued in the pediatric OLE; 4 turned 12 at the time of enrolment and are not included in this analysis.

The mean durations between the last dose in the Phase 2a study and the first dose in the OLE were 118 and 97 days for the 2 mg/kg and 4 mg/kg dose groups, respectively.

Baseline demographics and disease characteristics are shown in Table 11. The mean (±standard deviation [SD]) age was 8 (2) years and mean duration of AD was 7 (2) years in both dose groups. As shown in Table 11, disease characteristics at Phase 2a study baseline were consistent with severe AD. Mean (SD) EASI scores were 33 (16) and 39 (19); Peak Pruritus NRS scores were 6 (2) and 7 (2) and percentages of BSA affected were 59% (22) and 62% (30) in the 2 mg/kg and 4 mg/kg groups, respectively. Baseline disease severity was numerically higher in the 4 mg/kg vs. 2 mg/kg group in both the Phase 2a and OLE studies. 3 (17%, 2 mg/kg) and 7 patients (37%, 4 mg/kg) received non-steroidal immunosuppressants prior to baseline of the Phase 2a study, of whom 1 (6%) and 5 (26%), respectively, did not respond to this treatment. Most patients (78%, 2 mg/kg and 90%, 4 mg/kg) had other concomitant atopic/allergic diseases, including asthma, allergic rhinitis and food allergies.

TABLE 11

Baseline Demographics and Disease Characteristics

|  | Phase 2a study (N = 37) | | Phase 3 OLE study (N = 33) | |
| --- | --- | --- | --- | --- |
|  | 2 mg/kg (n = 18) | 4 mg/kg (n = 19) | 2 mg/kg (n = 17) | 4 mg/kg (n = 16) |
| Mean ± SD age (years) | 8 ± 2 | 8 ± 2 | 9 ± 2 | 8 ± 2 |
| Race, n (%) | | | | |
|   White | 17 (94) | 18 (95) | 16 (94) | 15 (94) |
|   Black or African American | 0 | 1 (5) | 0 | 1 (6) |
|   Other | 1 (6) | 0 | 1 (6) | 0 |
| Sex, male, n (%) | 9 (50) | 11 (58) | 8 (47) | 9 (56) |
| Mean ± SD weight (kg) | 30.8 ± 8.7 | 29.6 ± 9.8 | 30.9 ± 9.0 | 29.3 ± 8.6 |
| Mean ± SD BMI (kg/m$^2$) | 17.5 ± 2.8 | 16.8 ± 2.0 | 16.9 ± 3.0 | 17.0 ± 2.2 |
| Mean ± SD duration of AD (years) | 7 ± 2 | 7 ± 2 | 7 ± 3 | 8 ± 2 |
| Mean ± SD EASI score (scale 0-72) | 33 ± 16 | 39 ± 19 | 21 ± 18 | 32 ± 20 |
| IGA score, n (%) (scale 0-4) | | | | |
|   0 or 1 | N/A | N/A | 1 (6) | 0 |
|   2 | N/A | N/A | 3 (18) | 1 (6) |
|   3 | 1 (6)$^a$ | 0 | 9 (53) | 7 (44) |
|   4 | 17 (94) | 19 (100) | 4 (24) | 8 (50) |
| Mean ± SD Peak Pruritus NRS (scale 0-10) | 6 ± 2 | 7 ± 2 | 6 ± 3 | 6 ± 2 |
| Mean ± SD BSA affected by AD (%) | 59 ± 22 | 62 ± 30 | 37 ± 27 | 50 ± 31 |
| Mean ± SD SCORAD (scale 0-103) | 66 ± 13 | 73 ± 13 | 52 ± 17 | 67 ± 18 |
| Mean ± SD POEM (scale 0-28) | N/A | N/A | 17 ± 8 | 20 ± 5 |
| Mean ± SD CDLQI (scale 0-30) | N/A | N/A | 12 ± 8 | 12 ± 4 |
| Any previous non-steroidal systemic immunosuppressants, n (%) | 3 (17) | 7 (37) | N/A | N/A |
|   Azathioprine, n (%) | 0 | 2 (11) | N/A | N/A |
|   Cyclosporine A, n (%) | 3 (17) | 5 (26) | N/A | N/A |
|   No response to previous non-steroidal systemic immunosuppressants, n (%) | 1 (6) | 5 (26) | N/A | N/A |
| Patients with current history of atopic allergic conditions excluding AD, n (%) | 14 (78) | 17 (90) | N/A | N/A |
|   Allergic rhinitis | 9 (50) | 10 (53) | N/A | N/A |
|   Food allergy | 10 (56) | 14 (74) | N/A | N/A |
|   Asthma | 7 (39) | 9 (47) | N/A | N/A |
|   Allergic conjunctivitis | 3 (17) | 5 (26) | N/A | N/A |
|   Chronic rhinosinusitis | 0 | 1 (5) | N/A | N/A |
|   Urticaria | 1 (6) | 0 | N/A | N/A |
|   Other allergies | 12 (67) | 12 (63) | N/A | N/A |

AD, atopic dermatitis;
BMI, body mass index;
BSA, body surface area;
CDLQI, Children's Dermatology Life Quality Index;
EASI, Eczema Area and Severity Index;
IGA, Investigator's Global Assessment;
N/A, not applicable;
NRS, Numerical Rating Scale;
POEM, Patient-Oriented Eczema Measure;
SCORAD, SCORing, Atopic Dermatitis;
SD, standard deviation.

$^a$One patient from this age group enrolled in the study had a baseline disease severity of IGA = 3 but was still included in the analyses sets.

Figure 5A:
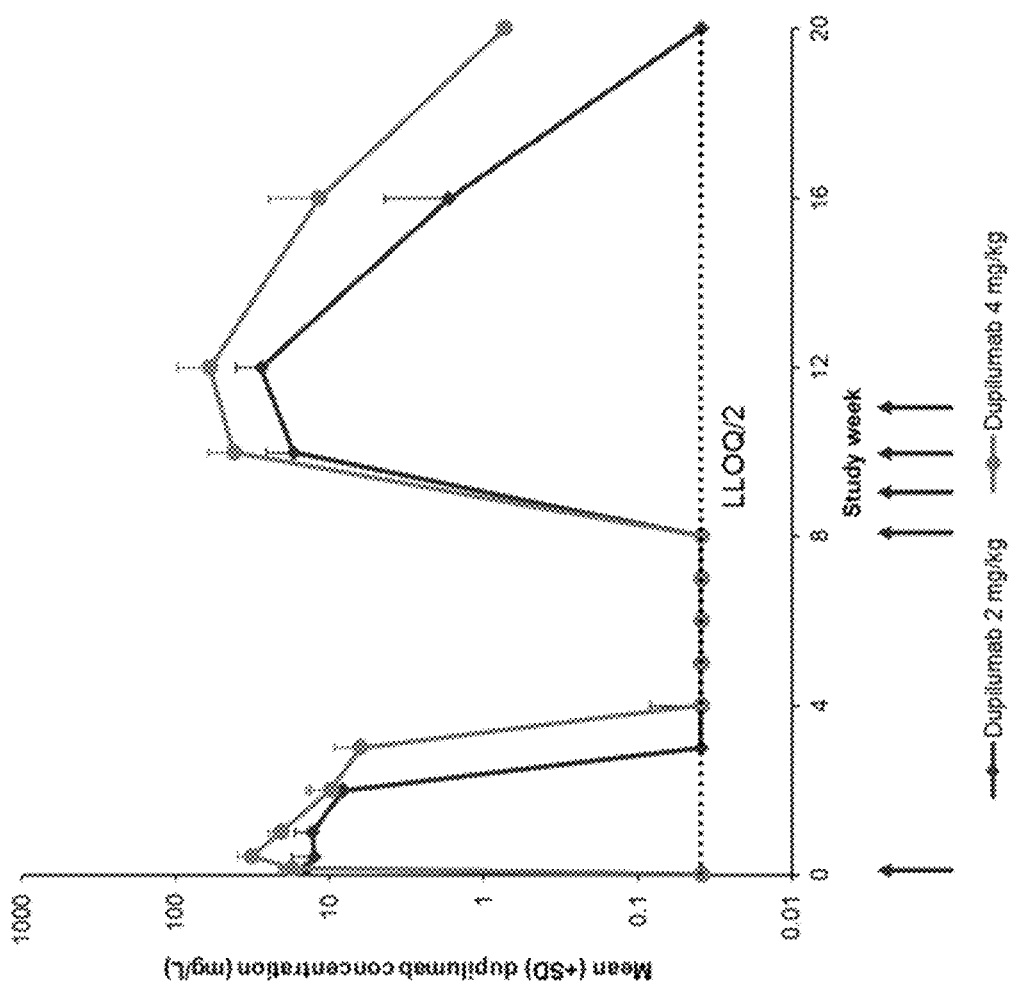
FIGS. 5A and 5B graphically depict the mean log-scaled concentrations of dupilumab in serum over nominal time.
Figure 5B:
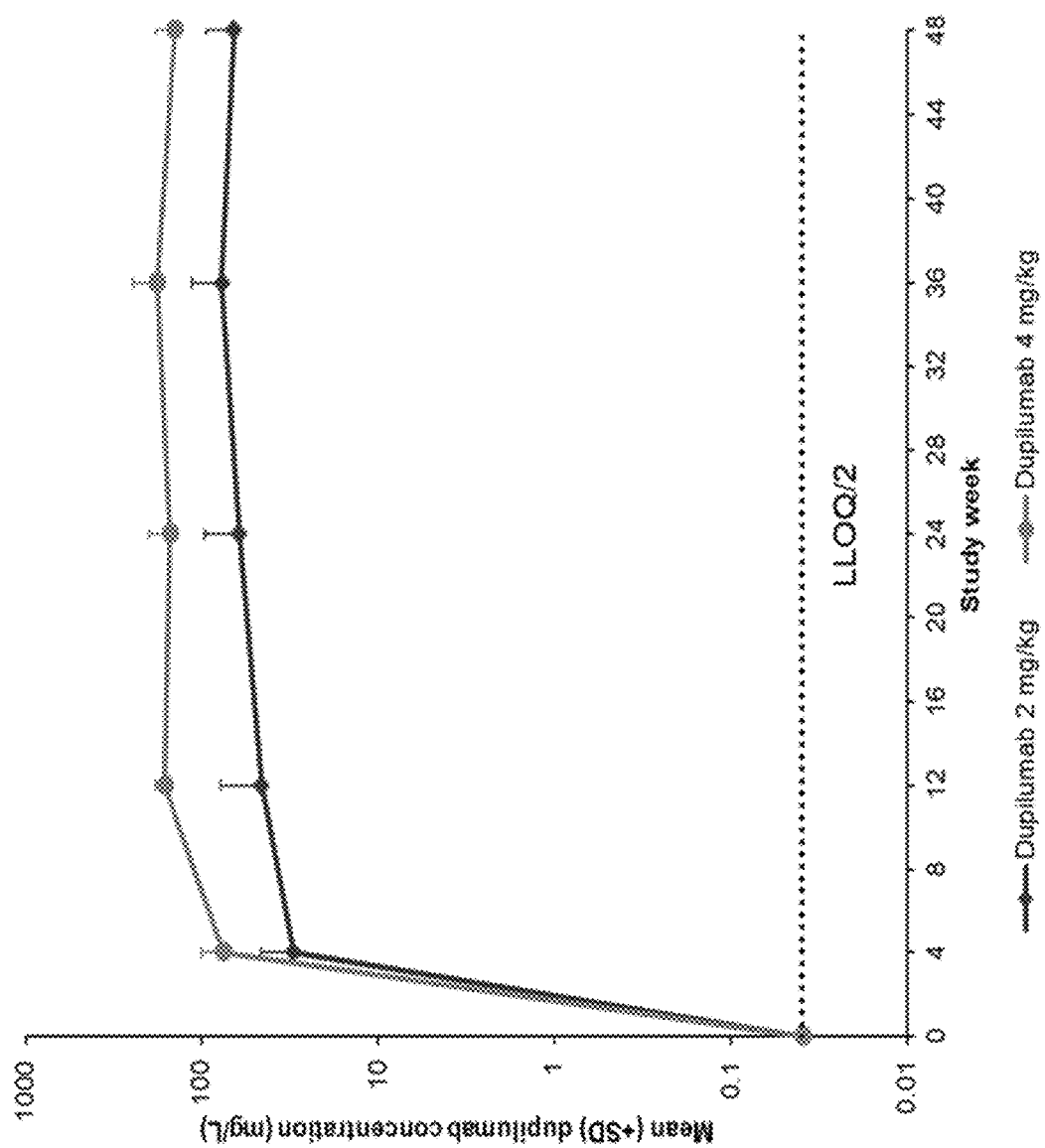

Following a single subcutaneous dose of dupilumab on day 1 of the Phase 2a study, $AUC_{last}$ calculated from the mean concentration-time profile in serum was 160 day*mg/L and 330 day*mg/L for the 2 mg/kg vs. 4 mg/kg groups, respectively. In the 2 mg/kg group, $t_{max}$ was observed at 2 days after dosing with a $C_{max}$ (±SD) of 14.3 mg/L (5.9). In the 4 mg/kg group, $t_{max}$ was observed 4 days after dosing with a $C_{max}$ (±SD) of 32.4 mg/L (7.0) (FIG. 5A). In the OLE, steady-state dupilumab trough mean (±SD) concentrations at weeks 24-48 ranged from 61.3 mg/L (35.0) to 76.8 mg/L (35.8) in the 2 mg/kg every week group, and 143 mg/L (40.3) to 181 mg/L (65.9) in the 4 mg/kg every week group (FIG. 5B).

As shown in Table 12, the majority of reported TEAEs in the Phase 2a were of mild or moderate severity (14% patients reported a severe TEAE). The overall incidence of serious TEAEs was low, with 2 patients (11%) experiencing a serious TEAE, both in the 4 mg/kg dose group in Part A of the study. Serious TEAEs included bacterial arthritis, infected dermatitis and AD exacerbation, which were deemed not related to treatment None of the events led to permanent treatment discontinuation. The most frequent TEAEs were nasopharyngitis and AD exacerbation. The proportion of patients with TEAEs was numerically higher in the 4 mg/kg dose cohort than in the 2 mg/kg dose cohort, which was driven by higher incidence of skin infections (High Level Term), cough (Preferred Term [PT]) and infected dermatitis (PT). Skin infections and AD exacerbation occurred mostly in patients not on dupilumab treatment at the time of TEAE onset (follow-up periods of Parts A or B). Injection-site reactions were mild, occurring only in the 4 mg/kg dose group. Three patients reported conjunctivitis events, all in the 4 mg/kg dose group (in both Parts A and B), none of which were severe or serious or led to treatment discontinuation; conjunctivitis resolved in 2 patients. One patient per dose group reported non-herpes viral infections in Part A of the study.

In the OLE, nearly all children reported ≥1 TEAE (Table 12). However, serious TEAEs were rare, with 2 (12%) and 3 (19%) patients experiencing 21 serious TEAE in the 2 mg/kg and 4 mg/kg dose group, respectively, none relating to treatment or leading to discontinuation of study drug. In the OLE, the most frequent TEAEs were nasopharyngitis and AD exacerbation. The proportions of patients with TEAEs, including skin infections, were comparable between the 4 mg/kg and 2 mg/kg dose group. However, there was a trend towards numerically higher TEAEs in the 4 mg/kg group vs. 2 mg/kg group when looking at exposure-adjusted incidence (nP/100PY). Two (12%) and 4 (25%) patients reported herpes viral infection. Injection-site reactions were mild and occurred in 3 patients across both dose groups. Seven patients reported conjunctivitis events: 2 (12%) and 5 (31%) in the 2 mg/kg and 4 mg/kg dose group, respectively, of whom conjunctivitis was reported as treatment related in 1 patient (6.3%) in the 4 mg/kg group; conjunctivitis resolved in all patients. No events were severe or serious or led to treatment discontinuation.

Efficacy outcomes for the Phase 2a and Phase 3 OLE studies are shown in Table 13. By week 2 of the Phase 2a study, EASI decreased with a mean (±SD) percentage change from baseline of −37 (34) and −33 (28) after a single dose of 2 mg/kg and 4 mg/kg of dupilumab, respectively; improvements in EASI were maintained up to week 52 in the OLE (−92 [14] and −84 [17] in 2 mg/kg and 4 mg/kg groups, respectively. The proportions of patients achieving EASI-75 or IGA 0 or 1 at week 12 in the Phase 2a study further increased until week 52 in the OLE. By week 12 of the Phase 2a study, 56% and 47% of patients receiving 2 mg/kg and 4 mg/kg, respectively, of dupilumab achieved EASI-75, with proportions increasing to 94% and 75%, respectively, at week 52 of OLE. Similarly, by week 12 of the Phase 2a, 17% and 21% achieved IGA 0 or 1, respectively, with proportions further increasing to 76% and 25% at week 52 of OLE. Peak Pruritus NRS scores decreased from baseline by a mean (±SD) percentage of −17% (46) and −20% (47) at week 2 of the Phase 2a study, after a single dose of 2 mg/kg and 4 mg/kg of dupilumab, respectively; improvements were maintained up to week 52 in the OLE (−70% [32] and −58% [33], 2 mg/kg and 4 mg/kg, respectively]. Further improvements in other pruritus outcomes (patients with 23 point or 24-point reduction from baseline in Peak Pruritus NRS) were seen until week 52 in the OLE. Sustained improvements were also seen in EASI-50, EASI-90, SCORAD and percentage BSA affected by AD in the Phase 2a and OLE study up to week 52. AD symptoms and QoL as assessed by POEM and CDLQI were also improved from baseline to week 48 of the OLE.

Overall, 89% and 95% of patients in the 2 mg/kg and 4 mg/kg dupilumab groups of the Phase 2a study, respectively, used topical treatment as concomitant medication; the most commonly used topical treatment in both treatment arms was potent TCS (group III). In the OLE, 82% (2 mg/kg) and 94% (4 mg/kg) of children used concomitant topical medication, with the majority (65% and 69%) using potent (group Ill) TCS.

TABLE 12

Safety Assessment

| | Phase 2a study (N = 37) | | | | Phase 3 OLE study (N = 33) | | | |
|---|---|---|---|---|---|---|---|---|
| | 2 mg/kg (n = 18) | | 4 mg/kg (n = 19) | | 2 mg/kg | 4 mg/kg | 2 mg/kg | 4 mg/kg |
| Number of TEAEs | Part A | Part B | Part A | Part B | (n = 17) | (n = 16) | (n = 17) | (n = 16) |
| | | | n | | | n | nE/100 PY | |
| Total TEAEs | 18 | 23 | 47 | 47 | 136 | 139 | 353 | 458 |
| Total serious TEAEs[a] | 0 | 0 | 3 | 0 | 2 | 5 | 5 | 16 |
| Total TEAEs related to treatment | 0 | 1 | 4 | 4 | 14 | 2 | 36 | 7 |
| Total serious TEAEs related to treatment | 0 | 0 | 0 | 0 | 0 | 0 | 0 | 0 |
| Total TEAEs resulting in permanent study drug discontinuation | 0 | 0 | 0 | 0 | 0 | 0 | 0 | 0 |

TABLE 12-continued

Safety Assessment

| Patients with TEAEs | n (%) | | | | n (%) | | nP/100 PY | |
|---|---|---|---|---|---|---|---|---|
| Any TEAE | 9 (50) | 10 (56) | 16 (84) | 17 (89) | 16 (94) | 16 (100) | 266 | 471 |
| Any serious TEAE | 0 | 0 | 2 (11) | 0 | 2 (12) | 3 (19) | 6 | 11 |
| Any TEAE related to treatment | 0 | 1 (6) | 3 (16) | 3 (16) | 4 (24) | 2 (13) | 13 | 7 |
| Any TEAE leading to treatment discontinuation | 0 | 0 | 0 | 0 | 0 | 0 | 0 | 0 |
| Patients with TEAE resulting in death | 0 | 0 | 0 | 0 | 0 | 0 | 0 | 0 |
| Any infection (SOC) | 6 (33) | 8 (44) | 10 (53) | 12 (63) | 12 (71) | 15 (94) | 98 | 209 |
| Skin infection (HLT) | 1 (6) | 1 (6) | 7 (37) | 5 (26) | 5 (29) | 6 (38) | 17 | 25 |
| Non-herpetic skin infections (adjudicated) | 1 (6) | 1 (6) | 6 (32) | 5 (26) | 4 (24) | 3 (19) | 12 | 11 |
| Herpes viral infections (HLT) | 1 (6) | 0 | 1 (5) | 0 | 2 (12) | 4 (25) | 6 | 15 |
| Injection-site reactions (HLT) | 0 | 0 | 1 (5) | 1 (5) | 2 (12) | 1 (6) | 5 | 3 |
| Conjunctivitis[b] | 0 | 0 | 1 (5) | 2 (11) | 2 (12) | 5 (31) | 5 | 21 |
| Most common TEAEs[c] | | | | | | | | |
| Nasopharyngitis | 3 (17) | 4 (22) | 6 (32) | 4 (21) | 8 (47) | 9 (56) | 35 | 37 |
| Dermatitis atopic | 4 (22) | 4 (22) | 5 (26) | 3 (16) | 5 (29) | 2 (13) | 16 | 7 |
| Cough | 0 | 1 (6) | 5 (26) | 3 (16) | 2 (12) | 5 (31) | 6 | 20 |
| Dermatitis infected | 1 (6) | 0 | 3 (16) | 2 (11) | 2 (12) | 0 | 5 | 0 |
| Headache | 0 | 1 (6) | 2 (11) | 1 (5) | 4 (24) | 2 (13) | 13 | 7 |
| Upper respiratory tract infection | 0 | 1 (6) | 0 | 1 (5) | 2 (12) | 4 (25) | 6 | 16 |
| Herpes simplex | 0 | 0 | 0 | 0 | 0 | 4 (25) | 0 | 15 |

[a]Serious TEAEs reported in the OLE included lymphadenopathy, anaphylactic reaction, pneumonia, allergy test, arthralgia, complex regional pain syndrome and dizziness postural.
[b]Includes PTs: conjunctivitis allergic, conjunctivitis bacterial, conjunctivitis viral, atopic keratoconjunctivitis.
[c]Includes all MedDRA PTs reported in 15% or 20%of patients in any treatment group of the Phase 2a study or Phase 3 OLE, respectively.
HLT, MedDRA High Level Term; MedDRA, Medical Dictionary for Regulatory Activities; nE, number of events; nP, number of patients; PT, MedDRA Preferred Term; PY, patient-years; SOC, MedDRA System Organ Class; TEAE, treatment-emergent adverse event.

TABLE 13

Efficacy Assessment

| | Dupilumab 2 mg/kg | | | | | Dupilumab 4 mg/kg | | | | |
|---|---|---|---|---|---|---|---|---|---|---|
| | Phase 2a study (n = 18) | | Phase 3 OLE (n = 17) | | | Phase 2a study (n = 19) | | Phase 3 OLE (n = 16) | | |
| | Week 2 | Week 12 | Week 0[a] | Week 16 | Week 52 | Week 2 | Week 12 | Week 0[a] | Week 16 | Week 52 |
| Mean ± SD EASI (n) | 23 ± 18 (18) | 9 ± 13 (16) | 21 ± 18 (17) | 9 ± 14 (17) | 2 ± 3 (17) | 26 ± 16 (18) | 16 ± 15 (19) | 32 ± 20 (16) | 7 ± 8 (15) | 5 ± 5 (16) |
| Mean ± SD % change in EASI from baseline of phase 2a study (N1) | −37 ± 34 (18) | −76 ± 25 (16) | −37 ± 37 17) | −73 ± 42 (170) | −92 ± 14 (17) | −33 ± 28 (18) | −63 ± 25 (19) | −20 ± 32 (16) | −84 ± 14 (15) | −84 ± 17 (16) |
| Patients achieving EASI-50 from baseline of phase 2a study, n/N (%) | 7/18 (39) | 14/18 (78) | 7/17 (41) | 16/17 (94) | 16/17 (94) | 5/19 (26) | 11/19 (58) | 3/16 (19) | 14/15 (93) | 15/16 (94) |
| Patients achieving EASI-75 from baseline of phase 2a study, n/N (%) | 3/18 (17) | 10/18 (56) | 4/17 (24) | 10/17 (59) | 16/17 (94) | 2/19 (11) | 9/19 (47) | 1/16 (6) | 11/15 (73) | 12/16 (75) |
| Patients with EASI-90 from baseline of phase 2a study, n/N (%) | 1/18 (6) | 6/18 (33) | 0/17 (0) | 7/17 (41) | 12/17 (71) | 0/19 (0) | 5/19 (26) | 0/16 (0) | 5/15 (33) | 7/16 (44) |
| Patients achieving IGA 0 or 1, n/N (%) | 1/18 (6) | 3/18 (17) | 1/17 (6) | 6/17 (35) | 13/17 (76) | 0/19 (0) | 4/19 (21) | 0/16 (0) | 6/15 (40) | 4/16 (25) |
| Mean ± SD Peak Pruritus NRS (N1) | 5 ± 3 (17) | 3 ± 2 (16) | 6 ± 3 (17) | 3 ± 2 (17) | 2 ± 2 (17) | 5 ± 3 (18) | 4 ± 2 (19) | 6 ± 2 (16) | 3 ± 2 (16) | 3 ± 2 (16) |
| Mean ± SD % change in Peak Pruritus NRS from baseline of phase 2a study (N1) | −17 ± 46 (17) | −42 ± 35 (16) | −9 ± 39 (17) | −50 ± 42 (17) | −70 ± 32 (17) | −20 ± 47 (18) | −40 ± 41 (19) | 5 ± 68 (16) | −51 ± 44 (16) | −58 ± 33 (16) |
| Patients with ≥3-point improvement in Peak Pruritus NRS from baseline of phase 2a study, n/N (%) | 4/18 (22) | 7/18 (39) | 4/17 (24) | 11/17 (65) | 14/17 (82) | 7/19 (37) | 10/19 (53) | 6/16 (38) | 11/16 (69) | 11/16 (69) |

TABLE 13-continued

Efficacy Assessment

| | Dupilumab 2 mg/kg | | | | | Dupilumab 4 mg/kg | | | | |
| | Phase 2a study (n = 18) | | Phase 3 OLE (n = 17) | | | Phase 2a study (n = 19) | | Phase 3 OLE (n = 16) | | |
| | Week 2 | Week 12 | Week 0[a] | Week 16 | Week 52 | Week 2 | Week 12 | Week 0[a] | Week 16 | Week 52 |
|---|---|---|---|---|---|---|---|---|---|---|
| Patients with ≥4-point improvement in Peak Pruritus NRS from baseline of phase 2a study, n/N (%) | 2/18 (11) | 5/18 (28) | 1/17 (6) | 9/17 (53) | 11/17 (65) | 5/19 (26) | 9/19 (47) | 3/16 (19) | 11/16 (69) | 11/16 (69) |
| Mean ± SD SCORAD (N1) | 51 ± 20 (17) | 28 ± 15 (16) | 52 ± 17 (17) | 26 ± 20 (17) | 14 ± 11 (17) | 52 ± 15 (18) | 38 ± 17 (19) | 67 ± 18 (16) | 29 ± 15 (15) | 24 ± 14 (16) |
| Mean ± SD % change in SCORAD from baseline of phase 2a study (N1) | −25 ± 21 (17) | −58 ± 23 (16) | −22 ± 20 (17) | −61 ± 31 (17) | −79 ± 16 (17) | −28 ± 19 (18) | −47 ± 24 (19) | −10 ± 23 (16) | −62 ± 18 (15) | −67 ± 19 (16) |

EASI, Eczema Area and Severity Index; EASI-50/75/90, 50/75/90% improvement from baseline in EASI; IGA, Investigator's Global Assessment;
N1, patients with available measurements at the particular timepoint; NRS, Numerical Rating Scale; OLE, open-label extension; SCORAD, SCORing Atopic Dermatitis; SD, standard deviation.
[a]The mean durations between the last dose in the Phase 2a study and the first dose in the Phase 3 OLE were 118 and 97 days for the 2 mg/kg and 4 mg/kg dose groups, respectively.

Discussion

In children aged ≥6-<12 years with severe AD, dupilumab up to 52 weeks was well tolerated with a favorable safety profile and no new safety concerns, consistent with studies in adolescent and adults with moderate-to-severe AD. No adverse events led to treatment discontinuation, and none of the reported serious TEAEs were considered related to dupilumab.

Although TEAE incidence was higher in the 4 mg/kg vs. 2 mg/kg dose group in the Phase 2a study, TEAE incidences were comparable in the OLE. No substantial differences in SAEs or TEAEs leading to treatment discontinuation were observed between the two dose regimens. Moreover, patients in this sequential cohort study were not randomized to dose regimens leading to differences in OLE baseline disease severity, and the number of patients in each dose regimen was small; a rigorous comparison between the dose regimens was therefore not possible. Although a higher incidence of skin infection was seen with 4 mg/kg vs. the 2 mg/kg dose in the Phase 2a study, rates were similar in the OLE. Skin infections occurred mostly in patients not being treated with dupilumab at the time of TEAE onset (patients were in the follow-up periods of Parts A or B). Many AD patients have skin colonization with *Staphylococcus aureus*, and AD patients are prone to developing skin infections. Dupilumab, by treating AD, should lead to a reduction in skin infections. Phase 3 trials in adults and adolescents with AD showed the incidence of skin infections was numerically lower in patients treated with dupilumab vs. placebo. See, Simpson et al., *JAMA Dermatol* 2020, 156:44-56.

AD signs and symptoms, including pruritus, showed rapid improvements with single-dose dupilumab in the Phase 2a study for both the 2 mg/kg and the 4 mg/kg doses. Improvements in clinical scores (EASI, SCORAD) and Peak Pruritus NRS were observed as early as week 2, with further improvement on continued treatment up to week 52 in the OLE. QoL was also improved with long-term treatment. The PK profile in children with severe AD was similar to that in adults and adolescents with moderate-to-severe AD and characterized by nonlinear, target-mediated kinetics. These safety and efficacy results support the use of dupilumab as continuous long-term treatment for children aged ≥6 to <12 years with severe AD.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for treating atopic dermatitis (AD) or improving an AD-associated parameter in a subject, the method comprising
    administering an interleukin-4 receptor (IL-4R) antagonist to a subject with moderate-to-severe or severe AD, wherein the subject is ≥6 years to <12 years of age, wherein the IL-4R antagonist is an anti-IL-4R antibody, or an antigen-binding fragment thereof, that comprises the heavy chain complementarity determining regions (HCDRs) of a heavy chain variable region (HCVR) comprising the amino acid sequence of SEQ ID NO:1 and the light chain complementarity determining regions (LCDRs) of a light chain variable region (LCVR) comprising the amino acid sequence of SEQ ID NO:2;
    wherein the IL-4R antagonist is subcutaneously administered at an initial dose followed by one or more secondary doses, wherein:
    (i) for a subject having a body weight of <30 kg, the IL-4R antagonist is administered at an initial dose of 600 mg followed by one or more secondary doses of 300 mg every four weeks (Q4W); or
    (ii) for a subject having a body weight of ≥30 kg to <60 kg, the IL-4R antagonist is administered at an initial dose of 400 mg followed by one or more secondary doses of 200 mg every two weeks (Q2W); or
    (iii) for a subject having a body weight of ≥60 kg, the IL-4R antagonist is administered at an initial dose of 600 mg followed by one or more secondary doses of 300 mg Q2W.

2. The method of claim 1, wherein the subject has a body weight of <30 kg and the IL-4R antagonist is administered at an initial dose of 600 mg followed by one or more secondary doses of 300 mg Q4W.

3. The method of claim 2, wherein the subject has a body weight of ≥15 kg to <30 kg.

4. The method of claim 1, wherein the subject has a body weight of ≥30 kg to <60 kg and the IL-4R antagonist is administered at an initial dose of 400 mg followed by one or more secondary doses of 200 mg Q2W.

5. The method of claim 1, wherein the subject has a body weight of ≥60 kg and the IL-4R antagonist is administered at an initial dose of 600 mg followed by one or more secondary doses of 300 mg Q2W.

6. The method of claim 1, wherein the subject is a subject with severe AD that cannot be adequately controlled with topical AD medications or for whom topical treatment is medically inadvisable.

7. The method of claim 6, wherein the subject is inadequately responsive to treatment with a topical corticosteroid (TCS).

8. The method of claim 1, wherein the subject is a subject with severe AD who is a candidate for systemic therapy.

9. The method of claim 1, wherein the subject:
    (i) has a baseline Investigator's Global Assessment (IGA) score=4;
    (ii) has a baseline Eczema Area and Severity Index (EASI) score ≥21;
    (iii) has a baseline Body Surface Area (BSA) affected by AD ≥15%; and/or
    (iv) has chronic AD diagnosed at least one year prior to the onset of treatment.

10. The method of claim 1, wherein the subject has a concurrent allergic condition selected from the group consisting of allergic rhinitis, asthma, food allergy, allergic conjunctivitis, hives, chronic rhinosinusitis, nasal polyps, and eosinophilic esophagitis.

11. The method of claim 1, wherein the IL-4R antagonist is administered in combination with a TCS.

12. The method of claim 11, wherein the TCS is a medium-potency TCS.

13. The method of claim 11, wherein the TCS is a low-potency TCS.

14. The method of claim 11, wherein treatment with the IL-4R antagonist reduces the amount of TCS that is administered to the subject relative to baseline.

15. The method of claim 1, wherein treatment with the IL-4R antagonist results in an improvement of an AD-associated parameter that is selected from:
    (i) a reduction from baseline in IGA score to achieve an IGA score of 0 or 1 by week 16 after administration of the first dose of the IL-4R antagonist; and
    (ii) a reduction of at least 75% from baseline in an EASI score (EASI-75) by week 16 after administration of the first dose of the IL-4R antagonist.

16. The method of claim 1, wherein the anti-IL-4R antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO:3; the HCDR2 comprises the amino acid sequence of SEQ ID NO:4; the HCDR3 comprises the amino acid sequence of SEQ ID NO:5; the LCDR1 comprises the amino acid sequence of SEQ ID NO:6; the LCDR2 comprises the amino acid sequence of SEQ ID NO:7; and the LCDR3 comprises the amino acid sequence of SEQ ID NO:8.

17. The method of claim 1, wherein the anti-IL-4R antibody or antigen-binding fragment thereof comprises a HCVR comprising the amino acid sequence of SEQ ID NO:1 and comprises a LCVR comprising the amino acid sequence of SEQ ID NO:2.

18. The method of claim 1, wherein the anti-IL-4R antibody comprises a heavy chain comprising the amino acid sequence of SEQ ID NO:9 and a light chain comprising the amino acid sequence of SEQ ID NO:10.

19. The method of claim 1, wherein the IL-4R antagonist is dupilumab or a bioequivalent thereof.

20. The method of claim 1, wherein the IL-4R antagonist is contained in a container selected from the group consisting of a glass vial, a syringe, a pre-filled syringe, a pen delivery device, and an autoinjector.

21. The method of claim 20, wherein the IL-4R antagonist is contained in a pre-filled syringe.

22. The method of claim 21, wherein the pre-filled syringe is a single-dose pre-filled syringe.

23. The method of claim 20, wherein the IL-4R antagonist is contained in an autoinjector.

24. The method of claim 20, wherein the IL-4R antagonist is contained in a pen delivery device.

* * * * *

SEQUENCE LISTING

```
<160> NUMBER OF SEQ ID NOS: 11

<210> SEQ ID NO 1
<211> LENGTH: 124
<212> TYPE: PRT
<213> ORGANISM: Artificial Sequence
<220> FEATURE:
<223> OTHER INFORMATION: HCVR

<400> SEQUENCE: 1

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
```

```
                35                  40                  45
Ser Ser Ile Ser Gly Ser Gly Gly Asn Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
            115                 120

<210> SEQ ID NO 2
<211> LENGTH: 112
<212> TYPE: PRT
<213> ORGANISM: Artificial Sequence
<220> FEATURE:
<223> OTHER INFORMATION: LCVR

<400> SEQUENCE: 2

Asp Ile Val Met Thr Gln Ser Pro Leu Ser Leu Pro Val Thr Pro Gly
 1                5                  10                  15

Glu Pro Ala Ser Ile Ser Cys Arg Ser Ser Gln Ser Leu Leu Tyr Ser
                20                  25                  30

Ile Gly Tyr Asn Tyr Leu Asp Trp Tyr Leu Gln Lys Ser Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 3
<211> LENGTH: 8
<212> TYPE: PRT
<213> ORGANISM: Artificial Sequence
<220> FEATURE:
<223> OTHER INFORMATION: HCDR1

<400> SEQUENCE: 3

Gly Phe Thr Phe Arg Asp Tyr Ala
 1                5

<210> SEQ ID NO 4
<211> LENGTH: 8
<212> TYPE: PRT
<213> ORGANISM: Artificial Sequence
<220> FEATURE:
<223> OTHER INFORMATION: HCDR2

<400> SEQUENCE: 4

Ile Ser Gly Ser Gly Gly Asn Thr
 1                5

<210> SEQ ID NO 5
<211> LENGTH: 18
<212> TYPE: PRT
<213> ORGANISM: Artificial Sequence
```

```
<220> FEATURE:
<223> OTHER INFORMATION: HCDR3

<400> SEQUENCE: 5

Ala Lys Asp Arg Leu Ser Ile Thr Ile Arg Pro Arg Tyr Tyr Gly Leu
1               5                   10                  15

Asp Val

<210> SEQ ID NO 6
<211> LENGTH: 11
<212> TYPE: PRT
<213> ORGANISM: Artificial Sequence
<220> FEATURE:
<223> OTHER INFORMATION: LCDR1

<400> SEQUENCE: 6

Gln Ser Leu Leu Tyr Ser Ile Gly Tyr Asn Tyr
1               5                   10

<210> SEQ ID NO 7
<211> LENGTH: 3
<212> TYPE: PRT
<213> ORGANISM: Artificial Sequence
<220> FEATURE:
<223> OTHER INFORMATION: LCDR2

<400> SEQUENCE: 7

Leu Gly Ser
1

<210> SEQ ID NO 8
<211> LENGTH: 9
<212> TYPE: PRT
<213> ORGANISM: Artificial Sequence
<220> FEATURE:
<223> OTHER INFORMATION: LCDR3

<400> SEQUENCE: 8

Met Gln Ala Leu Gln Thr Pro Tyr Thr
1               5

<210> SEQ ID NO 9
<211> LENGTH: 451
<212> TYPE: PRT
<213> ORGANISM: Artificial Sequence
<220> FEATURE:
<223> OTHER INFORMATION: HC

<400> SEQUENCE: 9

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110
```

Asp Val Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Leu Gly Thr Lys Thr Tyr Thr Cys
            195                 200                 205

Asn Val Asp His Lys Pro Ser Asn Thr Lys Val Asp Lys Arg Val Glu
            210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly
    450

<210> SEQ ID NO 10
<211> LENGTH: 219
<212> TYPE: PRT
<213> ORGANISM: Artificial Sequence
<220> FEATURE:
<223> OTHER INFORMATION: LC

<400> SEQUENCE: 10

Asp Ile Val Met Thr Gln Ser Pro Leu Ser Leu Pro Val Thr Pro Gly
1               5                   10                  15

```
Glu Pro Ala Ser Ile Ser Cys Arg Ser Ser Gln Ser Leu Leu Tyr Ser
                20                  25                  30

Ile Gly Tyr Asn Tyr Leu Asp Trp Tyr Leu Gln Lys Ser Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
                150                 155                 160
145

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 11
<211> LENGTH: 207
<212> TYPE: PRT
<213> ORGANISM: Artificial Sequence
<220> FEATURE:
<223> OTHER INFORMATION: hIL-4Ralpha

<400> SEQUENCE: 11

Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
                20                  25                  30

Leu Arg Leu Leu Tyr Gln Leu Val Phe Leu Leu Ser Glu Ala His Thr
            35                  40                  45

Cys Ile Pro Glu Asn Asn Gly Gly Ala Gly Cys Val Cys His Leu Leu
        50                  55                  60

Met Asp Asp Val Val Ser Ala Asp Asn Tyr Thr Leu Asp Leu Trp Ala
65                  70                  75                  80

Gly Gln Gln Leu Leu Trp Lys Gly Ser Phe Lys Pro Ser Glu His Val
                85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
        115                 120                 125

Tyr Asn His Leu Thr Tyr Ala Val Asn Ile Trp Ser Glu Asn Asp Pro
130                 135                 140

Ala Asp Phe Arg Ile Tyr Asn Val Thr Tyr Leu Glu Pro Ser Leu Arg
145                 150                 155                 160
```

```
Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
        195                 200                 205
```